(12) United States Patent
Myers et al.

(10) Patent No.: US 7,241,449 B1
(45) Date of Patent: Jul. 10, 2007

(54) TRANSFERRIN RECEPTOR GENES OF MORAXELLA

(75) Inventors: Lisa E. Myers, Rockwood (CA);
Anthony B. Schryvers, Calgary (CA);
Robin E. Harkness, Willowdale (CA);
Sheena M. Loosmore, Aurora (CA);
Run-Pan Du, Thornhill (CA);
Yan-Ping Yang, Willowdale (CA);
Michel H. Klein, Toronto (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/673,133

(22) PCT Filed: Apr. 12, 1999

(86) PCT No.: PCT/CA99/00307

§ 371 (c)(1),
(2), (4) Date: Jun. 11, 2002

(87) PCT Pub. No.: WO99/52947

PCT Pub. Date: Oct. 21, 1999

(51) Int. Cl.
*A61K 39/02* (2006.01)
*A61K 38/00* (2006.01)
*C07K 17/00* (2006.01)
*C07K 14/195* (2006.01)

(52) U.S. Cl. .............................. 424/251.1; 424/184.1; 424/190.1; 424/234.1; 530/350; 530/400; 530/412; 514/2

(58) Field of Classification Search .................... None
See application file for complete search history.

(56) References Cited

U.S. PATENT DOCUMENTS

| 4,258,029 A | 3/1981 | Moloney et al. |
| 4,855,283 A | 8/1989 | Lockhoff et al. |
| 5,194,254 A | 3/1993 | Barber et al. |
| 5,292,869 A | 3/1994 | Schryvers ................... 530/413 |
| 5,708,149 A | 1/1998 | Loosmore et al. |

FOREIGN PATENT DOCUMENTS

| WO | WO 90/12591 | 11/1990 |
| WO | WO 92/17167 | 10/1992 |
| WO | WO 93/08283 | 4/1993 |
| WO | WO 94/12641 | 6/1994 |
| WO | WO 95/33049 | 12/1995 |
| WO | WO 95/34308 | 12/1995 |
| WO | WO 97/13785 | 4/1997 |
| WO | WO 97/32380 | 9/1997 |
| WO | WO 97/32980 | 9/1997 |

OTHER PUBLICATIONS

Brorson, J-E., A. Axelsson, and S.E. Holm. 1976. Studies on *Branhamella catarrhalis* (*Neisseria catarrhalis*) with special reference to maxillary sinusitis. Scan. J. Infect. Dis. 8:151-155.

Catlin, B.W., 1990. *Branhamella catarrhalis*: an organism gaining respect as a pathogen. Clin. Microbiol. Rev. 3: 293-320.

Hager, H., A. Verghese, S. Alvarez, and S.L. Berk. 1987. *Branhamella catarrhalis* respiratory infections. Rev. Infect. Dis. 9:1140-1149.

McLeod, D.T., F. Ahmad, M.J. Croughan, and M.A. Calder. 1986. Bronchopulmonary infection due to *M. catarrhalis*. Clinical features and therapeutic response. Drugs 31(Suppl.3):109-112.

Nicotra, B., M. Rivera, J.I. Luman, and R.J. Wallace. 1986. *Branhamella catarrhalis* as a lower respiratory tract pathogen in patients with chronic lung disease. Arch.Intern.Med. 146:890-893.

Ninane, G., J. Joly, and M. Kraytman. 1978. Bronchopulmonary infection due to *Branhamella catarrhalis* 11 cases assessed by transtracheal puncture. Br.Med.Jr. 1:276-278.

Srinivasan, G., M.J. Raff, W.C. Templeton, S.J. Givens, R.C. Graves, and J.C. Mel. 1981. *Branhamella catarrhalis* pneumonia. Report of two cases and review of the literature. Am.Rev. Respir. Dis. 123:553-555.

West, M., S.L. Berk, and J.K. Smith. 1982. *Branhamella catarrhalis* pneumonia. South.Med. J. 75:1021-1023.

Christensen, J.J., and B. Bruun. 1985. Bacteremia caused by a beta-lactamase producing strain of *Branhamella catarrhalis*. Acta. Pathol. Microbiol. Immunol. Scand. Sect.B 93:273-275.

Craig, D.B., and P.A. Wehrle. 1983. *Branhamella catarrhalis* septic arthritis. J. Rheumatol. 10:985-986.

Guthrie, R., K. Bakenhaster, R.Nelson, and R. Woskobnick. 1988. *Branhamella catarrhalis* sepsis: a case report and review of the literature. J.Infect.Dis. 158:907-908.

Hiroshi, Saito, E.J. Anaissie, N.Khardori, and G.P. Bodey. 1988. *Branhamella catarrhalis* septicemia in patients Cancer 61:2315-2317.

O'Neill, J.H., and P.W. Mathieson. 1987. Meningitis due to *Branhamella catarrhalis*. Aust. N.Z. J. Med. 17:241-242.

Murphy, T.F. 1989. The surface of *Branhamella catarrhalis*: a systematic approach to the surface antigens of an emerging pathogen. Pediatr. Infect. Dis. J. 8:S75-S77.

Van Hare, G.F., P.A. Shurin, C.D. Marchant, N.A. Cartelli, C.E. Johnson, D. Fulton, S. Carlin, and C.H. Kim. Acute otitis media caused by *Branhamella catarrhalis*: biology and therapy. Rev. Infect. Dis. 9:16-27.

Jorgensen, J.H., Doem, G.V., Maher, L.A., Howell, A.W., and Redding, J.S., 1990 Antimicrobial resistance among respiratory isolates of *Haemophilus influenza*, *Moraxella catarrhalis*, and *Streptococcus* pneumoniae in the United States. Antibicrob. Agents Chemother. 34: 2075-2080.

Schryvers, A.B. and Morris, L.J. 1988 Identification and Characterization of the transferrin receptor from *Neisseria meningitidis*. Mol. Microbiol. 2:281-288.

(Continued)

*Primary Examiner*—Michael Pak
(74) *Attorney, Agent, or Firm*—Sanofi Pasteur Inc.

(57) ABSTRACT

Purified and isolated nucleic acid molecules are provided which encode Tbp2 proteins of *M. catarrhalis* strains M35, 3 and LES1. The nucleic acid sequence may be used to produce recombinant Tbp2 proteins of the strain of *Moraxella* free of other proteins of the *Moraxella* strain for purposes of diagnostics and medical treatment. Furthermore, the nucleic acid molecules may be used in the diagnosis of infection.

4 Claims, 73 Drawing Sheets

OTHER PUBLICATIONS

Lee, B.C., Schryvers, A.B. Specificity of the lactoferrin and transferrin receptors in *Neisseria gonorrhoeae*. Mol. Microbiol. 1988: 2-827-9.

Schryvers, A.B. Characterization of the human transferrin and lactoferrin receptors in *Haemophilus influenzae*. Mol. Microbiol. 1988; 2: 467-72.

Yu, R. and Schryvers, A.B., 1993. The interaction between human transferrin and transferrin binding protein 2 from *Moraxella* (*Branhamella*) *catarrhalis* differs from that of other human pathogens. Microbiol. Pathogenesis, 15:433-445.

O'Hagan, 1992. Clin. Pharmokinet. 22:1.

Ulmer et al., 1993. Curr. Opinion Invest. Drugs 2: 983-989.

Lockhoff, O., 1991. Glycolipds as immunomoclutators: Synthesis and properits. Chem. Int. Ed. Engl. 30: 1611-1620.

Nixon-George, 1990. J. Immunol. 14: 4798-4802.

Wallace, R.J. Jr., Nash, D.R., and Steingrube, V.A. 1990. Antibiotic susceptibilites and drug resistance in *Moraxella* (*Branhaemella*) *catarrhalis*. Am. J. Med. 88 (5A): 456-50S.

F.M. Ausubel et al., Short protocols in Molecular Biology, Greene Publishing Associates and John Wiley and Sons.

Schryvers, A.B., Lee, B.C. 1989. Comparative analysis of the transferrin and lactoferrin binding proteins in the family *Neisseriaceae*. Can. J. Microbiol. 35: 409-415.

Legrain, M., V. Mazarin, S.W. Irwin, B. Bouchon, M-J. Quentin-Millet, E. Jacobs, and A.B. Schryvers. 1993, Cloning and characterization of Neisseria meningitidis genes encoding the transferrin-binding proteins Tbp1 and Tbp2. Gene 130: 73-80.

Ogunnariwo, J.W., Woo, T.K.W., Lo, R.Y.C., Gonzalez, G.C., and Schryvers, A.B. Characterization of the Pasteurella haemolytica transferrin receptor genes and the recombinant receptor proteins. Microb. Pathog. 23:273-284 (1997).

Yang, Y.P., Myers, L.E., McGuinness, U., Chong, P., Kwok, Y., Klein, M.H. and Harkness R.E. The major outer membrane protein, C,D, extracted from *Moraxella* (*Branhamella*) *catarrhalis* is a potential vaccine antigen that induces bactericidal antibodies. FEMS Immun. Med. Microbiol. 17:187-199 (1997).

Needleman, S.B., and Wunsch, C.D. 1970, J. Mol Biol. 48:443-453.

Sellers, P.J. 1974 On the theory and computation of evolutionary distances, J. Appl. Math (Siam) 26:787-793.

Waterman, M.S., Smith, T.F., and Beyer, W.A. 1976. Advan. Math. 20:367-387.

Gerlach et al (1992) Infection and Immunity 60: 3253-3261.

Anderson et al (1994) J. Bacteriology 176: 3162-3170.

Gray-Owen et al (1995) Infection and Immunity 63: 1201-1210.

Bowie et al (1990) Science 247: 1306-1310.

Regenmortel (1986) TIBS 11: 36-39.

George et al (1988) Macromolecular Sequencing and Synthesis (Ed. By D. H. Schlesinger) Alan R. Liss, Inc., New York, pp. 127-129.

Smith, T.F., and Waterman, M.S. 1981 Identification of common molecular subsequences. J. Mol. Biol. 147:195-197.

Jimenez-Montano, M. and Zamora-Cortina, L. 1981 Evolutionary model for the generation of amino acid sequences and its application to the study of mammal alpha-hemoglobin chains. Proc. VII Int. Biophysics Congress, Mexico City.

Sobel, E. and Martinez, H.M. 1985 A Multiple Sequence Alignment Program. Nucleic Acid Res. 14:363-374.

Myers, L.E. et al, 1998, The transferrin binding protein B of *Moraxella catarrhalis* elicits bactericidal antibodies and is a potential vaccine antigen. Infect. And Immunity, vol. 66, No. 9,pp. 4183-4192.

FIG.2A

*M. catarrhalis* strain M35 *tbpB* sequence

```
MET LYS HIS ILE PRO LEU THR THR LEU CYS    VAL ALA ILE SER ALA VAL LEU LEU THR ALA
ATGAAACACATTCCTTTAACCACACTGTGT...........GTGGCAATCTCTGCCGTCTTATTAACCGCT
              10              20              30              40              50              60

CYS GLY GLY SER GLY GLY VAL SER ASN PRO PRO    ALA PRO THR PRO ILE PRO ASN ALA SER GLY
TGTGGTGGCAGTGGTGGTTCAAATCCACCT...........GCTCCTACGCCCATTCCAAATGCTAGCGGT
              70              80              90              100             110             120

SER GLY ASN THR GLY ASN THR GLY ASN ALA    GLY GLY THR ASP ASN THR ALA ASN ALA GLY
TCAGGTAATACTGGCAACACTGGTAATGCT...........GGCGGTACTGATAATACAGCCAATGCAGGT
              130             140             150             160             170             180

ASN THR GLY GLY THR ASN SER GLY THR GLY    SER ALA ASN THR PRO GLU PRO LYS TYR LYS
AATACAGGCGGTACAAACTCTGGTACAGGC...........AGTGCCAACACCAGAACCAAAATATAAAA
              190             200             210             220             230             240
```

FIG.2B

```
ASP VAL PRO THR ASP GLU ASN LYS LYS ASP....      ASP....
GATGTGCCAACCGATGAAAATAAAAAAGAT...                 ...GAAGTGTCAGGCATTCAAGAACCTGCCATG
         250              260           270...       280           290           300

GLY TYR GLY MET ALA LEU SER LYS MET ASN....
GGTTATGGCATGGCTTTGAGTAAAATGAAT...                 ...CTACACAACAAGACACGCCATTAGAT
         310              320           330...       340           350           360

GLU LYS ASP ILE ILE THR LEU ASP GLY LYS....
GAAAAAGATATCATTACCTTAGACGGTAAA...                 ...AAACAAGTTGCAAAAGGTGAAAATCGCCA
         370              380           390...       400           410           420

LEU PRO PHE SER LEU ASP VAL GLU ASN LYS....
TTGCCATTTTCGTTGGATGTAGAAAATAAA...                 ...TTGCTTGATGGCTATATAGCAAAATGAAT
         430              440           450...       460           470           480
```

Line 1 continued: GLU VAL SER GLY ILE GLN GLU PRO ALA MET
Line 2 continued: LEU HIS LYS GLN GLN ASP THR PRO LEU ASP
Line 3 continued: LYS GLN VAL ALA LYS GLY GLU LYS SER PRO
Line 4 continued: LEU LEU ASP GLY TYR ILE ALA LYS MET ASN

FIG.2C

```
GLU ALA ASP LYS ASN ALA    ILE GLY ASP ARG...                                                     SER LYS SER LEU
GAAGCGGATAAAAATGCC         ATTGGTGACAGA...   ...ILE LYS LYS ASP ASN LYS ASP LYS       ...AAGTCATTA
        490                     510          ...ATTAAGAAAGATAATAAAGACAAGTCATTA              540
                                                         520              530

SER LYS ALA GLU LEU ALA    LYS GLN ILE LYS...                                                     HIS GLU PHE GLN
TCTAAAGCAGAGCTTGCC         AAACAAATCAAA...    ...GLU ASP VAL ARG LYS SER       ...CCATGAGTTTCAG
        550                     570          ...GAAGATGTGCGTAAAAGCCATGAGTTTCAG            600
                                                         580              590

GLN VAL LEU SER SER LEU    LYS ASN LYS ILE...                                                     ASP GLY THR THR LYS ALA
CAAGTATTATCATCACTG         AAAAACAAAATT...    ...PHE HIS SER ASN       ...GATGGAACAACCAAAGCA
        610                     630          ...TTTCATTCAAATGATGGAACAACCAAAGCA            660
                                                         640              650

THR THR ARG ASP LEU GLN    TYR VAL ASP TYR...                                                     VAL ASN ASP GLY ASN TYR
ACCACGAGATTTACAA           TATGTTGATTAT...    ...GLY TYR TYR LEU       ...GTGAATGGCAATTAT
        670                     690          ...GGTTACTACTTGGTGAATGGCAATTAT             720
                                                         700              710
```

FIG.2D

```
LEU THR VAL LYS THR ASP GLU LEU TRP ASN ....
CT.ACCGTCAAAACAGACGAACTTTGGAAT
            730           740           750
                                              ...LEU GLY PRO VAL GLY GLY VAL PHE TYR ASN
                                              ...TTAGGCCCTGTGGGCGGTGTGTTTTATAAT
                                                       760           770           780

GLY THR THR ALA LYS GLU LEU PRO THR....
GGCACAACGACCGCCAAAGAGCTACCACA
            790           800           810
                                              ...GLN ASP ALA VAL LYS TYR LYS GLY HIS TRP
                                              ...CAAGATGCGGTCAAATATAAAGGACATTGG
                                                       820           830           840

ASP PHE MET THR ASP VAL ALA LYS GLN ARG....
GACTTTATGACCGATGTTGCCAAACAAAGA
            850           860           870
                                              ...ASN ARG PHE SER GLU VAL LYS GLU ASN LEU
                                              ...AACCGATTTAGCGAAGTGAAAGAAAACCTT
                                                       880           890           900

GLN ALA GLY ARG TYR TYR GLY ALA SER SER....
CAAGCAGGTCGGTATTATGGAGCATCTTCA
            910           920           930
                                              ...LYS ASP GLU TYR ASN ARG LEU LEU THR ASP
                                              ...AAAGATGAATACAACCGCTTATTAACTGAT
                                                       940           950           960
```

FIG.2E

```
GLU LYS ASN LYS PRO GLU ARG TYR ASN GLY...      GLU TYR GLY HIS SER SER GLU PHE THR VAL
GAGAAAAACAAACCAGAGCGTTATAACGGT...       ...GAATATGGTCATAGCAGTGAGTTTACTGTT
                   970               980                 990                 1000                1010                1020

ASN PHE LYS ASP LYS LYS LEU THR GLY GLU...      LEU PHE SER ASN LEU GLN ASP SER ARG LYS
AATTTTAAGGACAAAAAATTAACAGGTGAG...       ...CTGTTTAGTAACCTACAAGACAGCCGTAAG
                   1030              1040                1050                1060                1070                1080

GLY ASN VAL THR LYS THR LYS ARG TYR ASP....     ILE ASP ALA ASN ILE TYR GLY ASN ARG PHE
GGCAATGTTACGAAAACCAAACGCTATGAC...       ...ATCGATGCCAATATCTACGGCAACCGCTTC
                   1090              1100                1110                1120                1130                1140

ARG GLY SER ALA THR ALA SER ASP LYS ALA....     GLU ALA SER LYS THR LYS HIS PRO PHE THR
CGTGGCAGTGCCACCGCAAGCGATAAAGCA...       ...GAAGCAAGCAAAACCAAACACCCCTTTACC
                   1150              1160                1170                1180                1190                1200
```

FIG.2F

```
SER ASP ALA LYS ASN SER LEU GLU GLY GLY ....
AGCGATGCCAAAAATAGCCTAGAAGGCGGT...                            PHE TYR GLY PRO ASN ALA GLU GLU LEU ALA
       1210                    1220                   1230...TTTTATGGACCAAACGCCGAGGAGCTGGCA
                                                              ...                                   1260
                                                                     1240           1250

GLY LYS PHE LEU THR ASN ASP ASN LYS LEU ....
GGTAAATTCCTAACCAATGACAACAAACTC...                            PHE GLY VAL PHE GLY ALA LYS ARG GLU SER
       1270                    1280                   1290...TTTGGCGTCTTTGGTGCTAAACGAGAGAGT
                                                              ...                                   1320
                                                                     1300           1310

LYS ALA GLY GLU LYS THR GLU ALA ILE LEU ....
AAAGCTGGGGAAAAAACCGAAGCCATCTTA...                            ASP ALA TYR ALA LEU GLY THR PHE ASN LYS
       1330                    1340                   1350...GATGCCTATGCACTTGGGACATTTAACAAA
                                                              ...                                   1380
                                                                     1360           1370

ASN ASN ALA THR THR PHE THR PRO PHE THR ....
AATAACGCAACCACCACATTCACCCCATTTACC...                         LYS LYS GLN LEU ASP ASN PHE GLY ASN ALA
       1390                    1400                   1410...AAAAACAACTGGATAACTTTGGCAATGCC
                                                              ...                                   1440
                                                                     1420           1430
```

FIG.2G

```
LYS LYS LEU VAL LEU GLY SER THR VAL ILE....
A A A A A G T T G G T C T T G G G T T C T A C C G T C A T T...
              1450                  1460                  1470
                    ... ASP LEU VAL PRO THR GLY VAL THR LYS ASP
                    ... G A T T T G G T G C C T A C C G G T G T C A C C A A A G A T
                             1480                  1490                  1500

VAL ASN GLU PHE THR LYS ASN LYS PRO ASP....
G T C A A T G A A T T C A C C A A A A A C A A G C C A G A T...
              1510                  1520                  1530
                    ... SER ALA THR ASN LYS ALA GLY GLU THR LEU
                    ... T C T G C C A C A A A C A A A G C G G G C G A G A C T T T G
                             1540                  1550                  1560

MET VAL ASN ASP LYS VAL SER VAL LYS THR....
A T G G T G A A T G A T A A A G T T A G C G T C A A A A C C...
              1570                  1580                  1590
                    ... TYR GLY TYR GLY ARG ASN PHE GLU TYR LEU
                    ... T A T G G C T A T G G C A G A A A C T T T G A A T A C C T A
                             1600                  1610                  1620

LYS PHE GLY GLU LEU SER VAL GLY THR SER....
A A A T T T G G T G A G C T C A G T G T C G G C A C A A G C...
              1630                  1640                  1650
                    ... ASN SER VAL PHE LEU GLN GLY ARG THR
                    ... A A C A G C G T C T T T T T A C A A G G C G A A C G C A C C
                             1660                  1670                  1680
```

FIG.2H

```
ALA THR GLY GLU LYS ALA VAL PRO THR ...                                        ALA THR ...
GCTACCACAGGCGAGAAAGCCGTACCAACC...
                1690                                  1700                              1710...
                                            ...  LYS GLY THR ALA LYS TYR LEU GLY ASN TRP
                                            ... AAAGGCACAGCCAAATATTTGGGGAACTGG
                                                        1720                         1730                        1740
                                                ...

VAL GLY TYR ILE THR GLY LYS ASP SER SER ...
GTAGGATACATCACAGGAAAGGACTCATCA...
                1750                                   1760                             1770...
                                            ... LYS SER PHE GLU ASN GLU ALA GLN ASP VAL ALA
                                            ... AAAAGCTTTGAGAATGAGGCCCAAGATGTTGCT
                                                        1780                         1790                        1800
                                                ...

ASP PHE ASP ILE ASP PHE GLU LYS LYS SER ...
GATTTTGACATTGACTTTGAGAAAAAATCA...
                1810                                   1820                             1830...
                                            ... VAL LYS GLY LYS GLN LEU THR THR LYS ASP ARG
                                            ... GTTAAAGGCAAACTGACCACCAAAGACCGC
                                                        1840                         1850                        1860
                                                ...

GLN ASP PRO VAL PHE ASN ILE THR GLY ASP ...
CAAGACCCCTGTATTTAACATCACAGGTGAC...
                1870                                   1880                             1890...
                                            ... ILE ALA GLY ASN GLY TRP THR GLY LYS ALA
                                            ... ATCGCAGGCAATGGCTGGACAGGCAAAGCC
                                                        1900                         1910                        1920
                                                ...
```

FIG.2I

```
SER THR LYS ALA ASP ALA GLY GLY TYR ....
AGCACCAAAGCGGACGCAGGGGGCTAC....
         1930              1940              1950....
                                      ....  LYS ILE ASP SER SER THR GLY LYS SER
                                      ....  AAGATAGATTCTAGCAGTACAGGCAAATCC
                                              1960           1970           1980

ILE VAL ILE LYS ASP ALA GLU VAL THR GLY ....
ATCGTCATCAAAGATGCCGAGGTTACAGGG....
         1990              2000              2010....
                                      ....  GLY PHE TYR GLY PRO ASN ALA ASN GLU MET
                                      ....  GGCTTTTATGGTCCAAATGCAAACGAGATG
                                              2020           2030           2040

GLY GLY SER PHE THR HIS ASN THR ASP ASP ....
GGCGGGTCATTTACACACAACACCGATGAC....
         2050              2060              2070....
                                      ....  SER LYS ALA SER VAL VAL PHE GLY THR LYS
                                      ....  AGTAAAGCCTCTGTGGTCTTTGGCACAAAA
                                              2080           2090           2100

ARG GLN GLU. GLU VAL LYS ***
AGACAAGAAGAAGTTAAGTAG
         2110              2120
```

FIG.4A

M. catarrhalis strain 3 tbpB sequence

```
MET LYS HIS ILE PRO LEU THR THR LEU CYS ....
ATGAAACACATTCCTTTAACCACACTGT...
                10              20              30
        ...VAL ALA ILE SER ALA VAL LEU LEU THR ALA
        ...GTGGCAATCTCTGCCGTCTTATTAACCGCT
                        40              50              60

CYS GLY SER GLY GLY SER ASN PRO PRO ....
TGTGGTGGCAGTGGTTCAAATCCACCT...
                70              80              90
        ...ALA PRO THR PRO ILE PRO ASN ALA GLY GLY
        ...GCTCCTACGCCCATTCCAAATGCAGGCGGT
                        100             110             120

ALA GLY ASN ALA GLY SER GLY THR GLY GLY ....
GCAGGTAATGCTGGCGGTAGCGGTACTGGCGGT...
                130             140             150
        ...ALA GLY SER THR ASP ASN ALA ALA ASN ALA
        ...GCAGGTAGCACTGATAATGCAGCCAATGCA
                        160             170             180

GLY SER THR GLY GLY ALA SER SER GLY THR ....
GGCAGTACAGGCGGTGCAAGCTCTGGTACA...
                190             200             210
        ...GLY SER ALA SER THR GLN LYS PRO LYS TYR
        ...GGCAGTGCCAGCACACAAAAACCAAAATAT
                        220             230             240
```

FIG.4B

```
GLN ASP VAL PRO THR ASP LYS ASN LYS LYS....
CAAGATGTGCCAACCGATAAAAATAAAAAA...
              250                    260              270....
                                  ...ASP GLU VAL SER GLY ILE GLN GLU PRO ALA
                                  ...GATGAAGTGTCAGGCATTCAAGAACCTGCC
                                                280             290           300

MET GLY TYR GLY VAL GLU LEU LYS LEU ARG....
ATGGGTTATGGCGTGGAATTAAAGCTTCGT...
              310                    320              330....
                                  ...ASN TRP ILE ASP PRO GLN GLU GLU HIS
                                  ...AACTGGATACCACAAGAAGAACAT
                                                340             350           360

ALA LYS ILE ASN THR ASN ASP VAL VAL LYS....
GCCAAAATCAATACAAATGATGTTGTAAAA...
              370                    380              390....
                                  ...LEU GLU GLY ASP     LEU LYS HIS ASN PRO PHE
                                  ...CTTGAAGGTGACTTGAAGCATAATCCATTT
                                                400             410           420

ASP ASN SER ILE TRP GLN ASN ILE LYS ASN....
GACAACTCTATTTGGCAAAACATCAAAAAT...
              430                    440              450....
                                  ...SER LYS GLU VAL GLN THR VAL TYR ASN GLN
                                  ...AGCAAAGAAGTACAAACTGTTTACAACCAA
                                                460             470           480
```

FIG.4C

```
GLU LYS GLN ASN ILE GLU ASN GLN ILE LYS ...
GAGAAGCAAAACATTGAAAATCAAATCAAAA...
            490              500             510
                         ... LYS GLU ASN LYS GLU LEU ASP LYS THR ALA
                         ...AAAGAAAATAAAGAACTTGATAAAACGGCA
                               520             530            540

LEU LYS ALA LEU ILE GLU LYS VAL LEU ASP ...
CTAAAAGCTCTTATTGAAAAAGTTCTTGAT...
            550             560             570
                        ... ASP TYR LEU THR SER LEU ALA LYS PRO ILE
                        ...GACTATCTAACAAGTCTTGCTAAACCCATT
                               580            590             600

TYR GLU LYS ASN ILE ASN ASP SER HIS ASP ...
TATGAAAAAAATATTAATGATTCACATGAT...
            610             620             630
                        ... LYS GLN ASN LYS ALA ARG THR ARG ASP LEU
                        ...AAGCAGAATAAAGCACGCACTCGTGATTTG
                               640            650             660

LYS TYR VAL ARG SER GLY TYR ILE TYR ARG ...
AAGTATGTGCGTTCTGGTTATATTTATCGC...
            670             680             690
                        ... SER GLY TYR LEU SER ASN ILE ASP ILE GLN LYS
                        ...TCAGGTTATTCTAATATCGACATTCAAAAG
                               700            710             720
```

FIG.4D

```
LYS ILE ALA LYS THR GLY PHE ASP GLY ALA....
AAAATAGCTAAAACTGGTTTTGATGGTGCT...
              730              740           750...
                    LEU PHE TYR LYS GLY THR GLN THR ALA LYS
                 ...TTATTTTATAAAGGTACACAAACTGCTAAA
                       760              770              780

GLN LEU PRO VAL SER GLU VAL LYS TYR LYS....
CAATTGCCTGTATCTGAGGTTAAGTATAAA....
              790              800           810...
                    GLY THR TRP ASP PHE MET ASP ALA LYS
                 ...GGCACTTGGGATTTTATGACCGATGCCAAA
                       820              830              840

LYS GLY GLN SER SER PHE SER PHE GLU ARG....
AAAGGACAAATCATTTAGCAGTTTTGAAAGA....
              850              860           870...
                    ARG ALA GLY ASP ARG TYR SER ALA MET SER
                 ...CGAGCTGGTGATCGCTATAGTGCAATGTCT
                       880              890              900

SER HIS GLU TYR PRO SER LEU LEU THR ASP....
TCCCATGAGTACCCATCTTTATTAACTGAT....
              910              920           930...
                    ASP LYS ASN LYS PRO ASP ASN TYR ASN ASP
                 ...GATAAAAACAAACCAGATAATTATAACGAT
                       940              950              960
```

FIG.4E

```
GLU TYR GLY HIS SER SER GLU PHE THR VAL....
GAATATGGTCATAGCAGTGAGTTTACGGTA....
         970                 980              990...
                                  ...GATTTTAGTAAAAAGAGCCTAACAGGTGGG
                                            ASP PHE SER LYS LYS SER LEU THR GLY GLY
                                                 1000          1010              1020

LEU PHE SER ASN LEU GLN ASP HIS HIS LYS....
CTGTTTTAGTAACCTACAAGACCACCATAAG....
         1030                1040             1050...
                                  ...GGCAAGGTTACGAAAACCAAACGCTATGAC
                                            GLY LYS VAL THR LYS THR LYS ARG TYR ASP
                                                 1060          1070              1080

ILE ASN ALA ARG ILE HIS GLY ASN ARG PHE....
ATCAATGCCCGTATCCACGGTAACCGCTTC....
         1090                1100             1110...
                                  ...CGTGGCAGTGCCACCGCAATCAATAAAGAT
                                            ARG GLY SER ALA THR ALA ILE ASN LYS ASP
                                                 1120          1130              1140

ASN GLU SER LYS ALA LYS HIS PRO PHE THR....
AATGAAAGCAAAGCCAAACACCCCTTTACC....
         1150                1160             1170...
                                  ...AGCGATGCCGACAATAGGCTAGAAGGCGGT
                                            SER ASP ALA ASP ASN ARG LEU GLU GLY GLY
                                                 1180          1190              1200
```

FIG.4F

```
PHE TYR GLY PRO ASN ALA GLU GLU LEU ALA...        ...GLY LYS PHE LEU THR ASP ASP ASN LYS LEU
TTTTATGGACCAAACGCCGAGGAGCTGCA...              ...GGTAAATTCCTAACCGATGACAACAAACTC
              1210              1220        1230...           1240                  1250              1260

PHE GLY VAL PHE GLY ALA LYS GLN GLU SER....       ...GLU ALA LYS THR GLU ALA ILE LEU ASP
TTTGGTGTCTTTGGTGCTAAACAAGAGAGT....           ...GAAGCTAAGGAAACCGAAGCCATCTTAGAT
              1270              1280        1290....          1300                  1310              1320

ALA TYR ALA LEU GLY THR PHE ASN LYS SER....       ...GLY THR THR ASN PRO ALA PHE THR ALA ASN
GCTTATGCACTTGGGACATTTAATAAATCT....           ...GGTACGACCAATCCTGCCTTTACCGCCAAT
              1330              1340        1350....          1360                  1370              1380

SER LYS LYS GLU LEU ASP ASN PHE GLY ASN....       ...ILE ASN LYS LEU VAL LEU GLY SER THR VAL
AGTAAAAAAGAACTGGATAACTTTGGGAAT....           ...ATTAATAAATTGGTCTTGGGTTCTACTGTG
              1390              1400        1410....          1420                  1430              1440
```

FIG.4G

ILE  ASP  LEU  THR  GLN  GLY  ASN  ASP  PHE  VAL ...
ATAGACCTTACTCAAGGTAATGATTTTGTA...  LYS  THR  ILE  ASP  LYS  GLU  LYS  PRO  ALA  THR
            1450                    1460            ...AAAACCATTGATAAAGAAAAGCCAGCCACC
                                                          1480         1490         1500
                                    ...
                                                          1470

THR  THR  ASN  GLN  ALA  GLY  GLU  PRO  LEU  THR ...
ACTACCAATCAAGCAGGCGAGCCTTTGACG...  VAL  ASN  ASP  LYS  VAL  ARG  VAL  GLN  VAL  CYS
            1510                    1520             ...GTGAATGATAAGGTTCGGGTACAAGTTTGT
                                                          1540         1550         1560
                                    ...
                                                          1530

CYS  SER  ASN  LEU  GLU  HIS  LEU  LYS  PHE  GLY ...
TGTAGCAATCTTGAGCATCTAAAATTTGGC...  SER  LEU  SER  ILE  GLY  ASP  SER  ASN  SER  VAL
            1570                    1580             ...TCACTGAGTATCGGTGATAGTAATAGCGTC
                                                          1600         1610         1620
                                    ...
                                                          1590

PHE  LEU  GLN  GLY  GLU  ARG  THR  ALA  THR  LYS ...
TTTTTACAAGGTGAACGCACCGCTACCAAA...  GLY  ASP  LYS  ASP  LYS  ALA  MET  PRO  VAL  ALA
            1630                    1640             ...GGTGATAAAGATAAAGCCATGCCAGTTGCA
                                                          1660         1670         1680
                                    ...
                                                          1650

FIG. 4H

GLY ASN ALA LYS TYR ARG GLY THR TRP ALA....
G G A A A T G C T A A A T A C C G T G G T A C A T G G G C A...
                    1690                1700              1710....

... GLY TYR VAL ALA GLY SER GLY ASN THR SER
           ... G G C T A T G T T G C A G G C T C T G G C A A T A C C A G C
                   1720                1730              1740

LYS ALA TYR GLU ALA GLN GLN PHE ALA ASP ....
A A A G C C T A T G A A G C C C A A C A A T T T G C T G A C....
                    1750                1760              1770....

... ASN ALA ASN ARG ALA GLU PHE ASP VAL ASP
           ... A A T G C C A A C C G T G C C G A G T T T G A T G T A G A C
                   1780                1790              1800

PHE ALA ASN LYS SER LEU THR GLY LYS LEU ....
T T T G C T A A C A A A A G C C T A A C T G G T A A G C T T....
                    1810                1820              1830....

... ILE PRO ASN THR SER SER ASP GLY LYS SER
           ... A T T C C A A A T A C G A G C A G T G A T G G T A A A T C T
                   1840                1850              1860

ALA PHE ASP ILE THR ALA THR ILE ASP GLY ....
G C T T T T G A T A T T A C T G C T A C A A T T G A T G G C....
                    1870                1880              1890....

... ASN GLY PHE SER GLY LYS ALA ASN THR PRO
           ... A A T G G T T T T A G T G G T A A A G C C A A T A C A C C A
                   1900                1910              1920

FIG. 4I

```
ASP ILE GLU THR GLY GLY LEU LYS ILE ASP...
GATATTGAAACAGGTGGGTTAAAAGATTGAC...
          1930           1940          1950
                                              ...SER LYS ASN SER GLU SER GLY ARG VAL ILE
                                              ...AGTAAAGAACAGTGAAAGCGGCCGAGTAATT
                                                   1960           1970           1980

VAL LYS ASP ALA ILE VAL ILE GLY GLY PHE...
GTGAAAGATGCTATAGTTATAGGTGGCTTT...
          1990           2000          2010
                                              ...TYR GLY PRO GLN ALA ASN GLU LEU GLY GLY
                                              ...TATGGTCCACAAGCTAATGAACTGGGTGGC
                                                   2020           2030           2040

SER PHE THR TYR LYS SER ASN ASP ALA GLY...
TCATTTACCTACAAGAGCAATGATGCTGGA...
          2050           2060          2070
                                              ...ASN GLN ASP LYS ASP SER SER ALA SER VAL
                                              ...AATCAAGACAAAGACAGTAGTGCATCTGTG
                                                   2080           2090           2100

VAL PHE GLY ALA ARG LYS GLN GLN GLU VAL...
GTCTTTGGTGCAAGAAAACAACAAGAAGTC...
          2110           2120          2130
                                              ...LYS PRO ***
                                              ...AAACCATGA
```

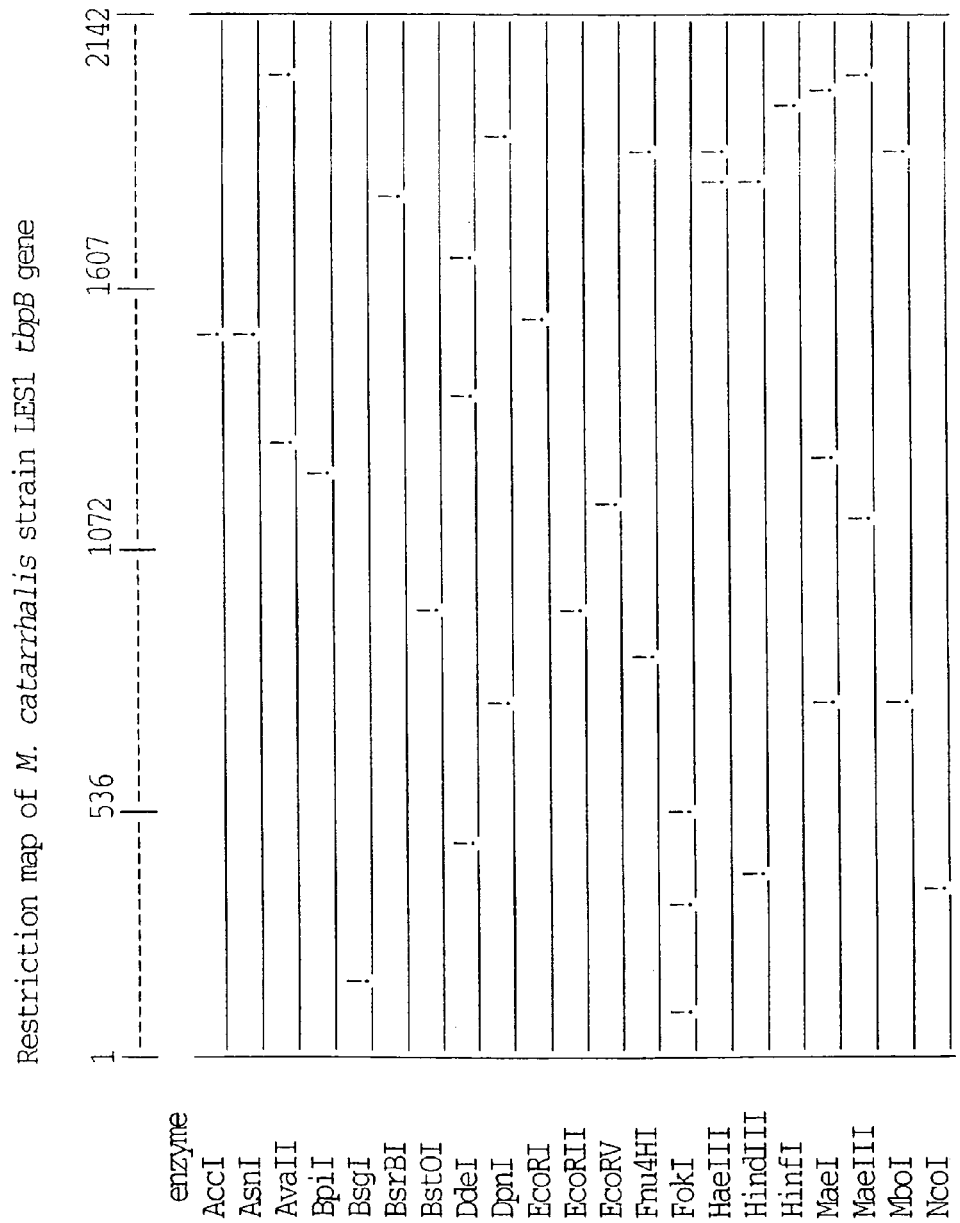
FIG.5A Restriction map of *M. catarrhalis* strain LES1 *tbpB* gene

FIG.6A

*M. catarrhalis* strain LES1 *tbpB* sequence

```
MET LYS HIS ILE PRO LEU THR THR LEU CYS ... VAL ALA ILE SER ALA VAL LEU LEU THR ALA
ATGAAACACATTCCTTTAACCACACTGT...GTGGCAATCTCTGCCGTCTTATTAACCGCT
         10                 30....40                 50                 60

CYS GLY SER GLY GLY GLY VAL SER ASN PRO PRO ... ALA PRO THR PRO ILE PRO ASN ALA GLY SER
TGTGGTGGCAGTGGTGGGTTCAAATCCACCT...GCTCCCTACGCCCATCCCAAATGCAGGCAGT
         70                 90....100                110                120

ALA GLY ASN ALA GLY GLY THR GLY ASN THR ... GLY GLY THR GLY SER THR ASP ASN VAL GLY
GCAGGTAATGCTGGCGGTACAGGAAATACA...GGCGGGTACTGGCAGTACTGATAATGTAGGC
         130                150....160                170                180

ASN ALA GLY GLY ALA ASN SER GLY THR GLY ... ASN ALA GLY ASN SER GLY ASN ALA ASN SER
AATGCTGGCGGTGCAAACTCTGGTACAGGC...AATGCAGGTAATTCAGGTAATGCAAACTCT
         190                210....220                230                240
```

FIG.6B

```
GLY THR GLY SER ALA ASN THR PRO GLU PRO ...
GGTACAGGCAGTGCCAACACACCAGAACCA...
         250              270...
                                       ... LYS TYR GLN ASP VAL PRO THR ASP LYS ASN
                                       ...AAATATCAAGATGTGCCAACCGATAAAAT
                                              280              290              300
                                       ...

GLU LYS GLU GLN VAL SER SER ILE GLN GLU ...
GAAAAAGAACAAGTTTCATCCATTCAAGAA...
         310              330...
                                       ... PRO ALA MET GLY TYR ALA MET GLU LEU LYS
                                       ...CCTGCCATGGGTTATGCAATGGAATTAAAG
                                                    340              350              360
                                       ...

LEU ARG ASN ALA HIS PRO LEU ASN PRO ASN ...
CTTCGTAATGCTCACCCTCTTAACCCCAAAT...
         370              390...
                                       ... LYS ASN LYS ARG GLU LYS ALA GLU LYS ARG ILE ALA
                                       ...AAAAATAAAGAGGCTGAAAAACGCATTGCC
                                              400              410              420
                                       ...

LEU ASP GLN LYS ASP LEU VAL ALA VAL GLU ...
TTAGACCAAAAAGATTTGGTGGCAGTAGAG...
         430              450...
                                       ... GLY ASP LEU THR ASN ILE PRO PHE ASP LYS
                                       ...GGCGACCTAACCAACATTCCTTTTGATAAA
                                              460              470              480
                                       ...
```

FIG. 6C

```
ASN LEU ILE GLU TYR LEU LYS LYS SER SER ....        GLU VAL VAL SER LYS PHE GLU ALA GLN LYS
AATCTTATTGAATACCTTAAAAAATCATCC...    ...GAGGTTGTAAGTAAATTTGAAGCACAAAAA
         490              500      510...         520              530              540

GLY GLY ILE GLU ASN THR ARG LEU THR ....        HIS LYS ASP LEU ASP ASN ALA ....        SER SER GLU GLN LYS GLU
GGCGGTATTGAAAATAACAAGACTGACA...      ...CACAAAGATTTATCATCAGAGCAAAAAGAA
         550              560      570...         580              590              600

ALA LYS VAL LYS GLU ALA LEU ASP ASN ALA ....        LEU THR GLN PHE ALA GLN GLU LYS TYR LYS
GCAAAAGTCAAAGAAGCGTTGGACAATGCT...    ...TTAACTCAATTTGCCCAAGAAAAATACAAG
         610              620      630...         640              650              660

GLU LEU ILE GLU ASN ALA HIS ASP LYS LYS ....        SER ASP ALA ARG ASN ARG ASP LEU GLU TYR
GAGCTAATTGAGAACGCCCATGATAAAAAA...    ...TCTGACGCACGCAACCGTGATCTAGAATAT
         670              680      690...         700              710              720
```

FIG.6D

```
VAL LYS SER GLY PHE ASN TYR LEU SER GLY....
GTCAAGTCTGGTTTTAACTATCTTTCTGGA...
            730              740          750....

ASN TYR ARG GLY TYR TYR GLY ALA LEU TYR...      TYR THR ALA THR ASP HIS ASP LYS LYS THR
AATTATCGTGGCTATTATGGTGCGTTGTAT...          ...TATACCGCCACCGACCACGACAAAAAACC
            790              800          810....       760              770              780

TYR LYS GLY SER GLU THR ALA LYS GLU LEU
                                               ...TATAAAGGCAGCGAAACCGCCAAAGAGCTA
                                                           820              830          840

PRO GLN THR SER ALA LYS TYR LYS GLY TYR...       TRP ASP PHE MET THR ASP ALA THR LEU ASP
CCACAAACAAGTGCAAAATATAAAGGTTAT...          ...TGGGACTTTATGACAGATGCCACACTTGAT
            850              860          870....       880              890              900

ASN LYS TYR THR ASP LEU PRO GLY ILE ALA....      ARG GLN THR GLN TRP ARG SER LEU VAL SER
AACAAATACACGGATTTGCCAGGTATCGCC...          ...AGACAAACCCAGTGGCGTAGTCTTGTTTCT
            910              920          930....       940              950              960
```

FIG.6E

```
THR ASP GLU TYR ALA THR LEU LEU THR ASP....
ACTGATGAGTATGCAACGCTCTTGACAGAC...
            970              980            990

...LYS ASN ASN LYS PRO SER ASP TYR ASN GLY
                ...AAAAATAACAAGCCCAGTGATTACAATGGT
                        1000           1010           1020

ALA TYR GLY HIS SER SER GLU PHE ASP VAL....
GCATATGGTCATAGCAGTGAATTTGATGTT...
           1030            1040           1050

...ASN PHE ALA ASP LYS LYS ILE LYS GLY LYS
                ...AATTTTGCTGATAAAAAATTAAAGGCAAA
                        1060           1070           1080

LEU ILE SER ASN GLN LEU SER GLY THR ALA....
CTTATCAGTAATCAGTTATCAGGCACAGCT...
           1090            1100           1110

...VAL THR ALA LYS GLU ARG TYR LYS ILE GLU
                ...GTAACCGCCAAAGAGCGTTATAAAATAGAA
                        1120           1130           1140

ALA ASP ILE HIS GLY ASN ARG PHE ARG GLY....
GCTGATATCCACGGCAACCGCTTCCGTGGC...
           1150            1160           1170

...SER ALA THR ALA SER ASP LYS ALA GLU ASP
                ...AGTGCCACCGCAAGCGATAAAGCAGAAGAC
                        1180           1190           1200
```

FIG.6F

```
SER LYS THR GLN HIS PRO PHE THR SER ASP ....
AGCAAAACCCAACACACCCCTTTACCAGCGAT...
        1210                  1220        1230...
          ... ALA THR ASN LYS LEU GLU GLY GLY PHE TYR
          ...GCTACAAAACAAGCTAGAAGGTGGTTTTTAT
                   1240             1250             1260

GLY PRO LYS GLY GLU GLU LEU ALA GLY LYS ....
GGACCAAAAGGCGAGGAGCTGGCAGGTAAA...
        1270                 1280        1290...
          ... PHE LEU THR ASP ASP ASN LYS LEU PHE GLY
          ...TTCTTAACCGATGACAACAAACTCTTTGGG
                   1300             1310             1320

VAL PHE GLY ALA LYS ARG ASP LYS VAL GLU ....
GTCTTTGGTGCTAAACGAGATAAAGTAGAA...
        1330                 1340        1350...
          ... LYS THR GLU ALA ILE LEU ASP ALA TYR ALA
          ...AAAACCGAAGCCATCTTAGATGCCTATGCA
                   1360             1370             1380

LEU GLY THR PHE ASN ASN THR ASN LYS ALA ....
CTTGGGACATTTAATAATACAAATAAAGCA...
        1390                 1400        1410...
          ... THR THR PHE PRO PHE THR LYS LYS GLN
          ...ACCACATTCACCCCATTTACCAAAAAACAA
                   1420             1430             1440
```

FIG.6G

```
LEU ASP ASN PHE GLY ASN ALA LYS LYS LEU                 VAL ILE ASN LEU VAL
CTGGATAACTTTGGCAATGCCAAAAAGTTG...        ...GTCTTGGGTTCTACCGTCATTAATTTGGTG
            1450              1460           1470         1480              1490              1500

SER THR ASP ALA THR LYS ASN GLU PHE THR....              LYS PHE THR LYS ASP LYS PRO THR SER
TCTACCGATGCCACCAAAAATGAATTCACC...        ...AAAAAATTCACCAAAGACAAGCCAACTTCT
            1510              1520              1530              1540             1550              1560

ALA THR ASN LYS ALA GLY GLU THR LEU MET....              VAL ASN ASP GLU VAL ILE LYS THR TYR
GCCACAAACAAAGCGGGCGAGACTTTGATG...        ...GTGAATGATGAAGTTATCGTCAAAACCTAT
            1570              1580              1590             1600              1610              1620

GLY LYS ASN PHE GLU TYR LEU LYS PHE GLY....              GLU LEU SER VAL GLY ASP SER HIS SER VAL
GGCAAAAACTTTGAATACCTAAAATTTGGT...        ...GAGCTTAGTGTCGGTGATAGCCATAGCGTC
            1630              1640              1650              1660             1670              1680
```

FIG.6H

PHE LEU GLN GLY GLU ARG THR ALA THR THR....
TTTTTACAAGGCGAACGCACCGCTACCACA...
         1690              1700             1710....

....GLY GLU LYS ALA VAL PRO THR THR GLY LYS
              ....GGCGAGAAAGCCGTACCAACCACAGGCAAA
                      1720            1730             1740

ALA LYS TYR LEU GLY ASN TRP VAL GLY TYR....
GCCAAATATCTGGGGAACTGGGTAGGATAC...
         1750             1760              1770....

....ILE THR GLY ALA GLY THR GLY LYS SER PHE
              ....ATCACAGGAGCGGGCACAGGAAAAAGCTTT
                      1780              1790             1800

ASN GLU ALA GLN ASP ILE ALA ASP PHE ASP....
AATGAGGCCCAAGATATTGCTGATTTTGAC...
         1810              1820             1830....

....ILE ASP PHE GLU ARG LYS SER VAL LYS GLY
              ....ATTGACTTTGAGAGAAAATCAGTTAAAGGC
                      1840             1850              1860

LYS LEU THR THR GLN GLY ARG THR ASP PRO....
AAACTGACCACCCAAGGCCGCACAGATCCT...
         1870             1880              1890....

....VAL PHE ASN ILE LYS GLY GLU ILE ALA GLY
              ....GTCTTTAACATCAAAGGTGAAATTGCAGGC
                      1900             1910              1920

FIG. 6I

```
ASN GLY TRP THR GLY LYS ALA SER THR THR...
AATGGCTGGACAGGCAAAGCCAGCACCACC...
              1930              1940         1950

...LYS ALA ASP ALA GLY GLY TYR LYS ILE ASP
         ...AAAGCGGACGCAGGAGGCTACAAGATAGAT
              1960              1970              1980

SER SER THR GLY LYS SER ILE VAL ILE...
TCTAGCAGTACAGGCAAATCCATCGTCATC...
              1990              2000         2010

...GLU ASN ALA GLU VAL THR GLY GLY PHE TYR
         ...GAAAATGCCGAAGTTACTGGGGGCTTTTAT
              2020              2030              2040

GLY PRO ASN ALA ASN GLU MET GLY GLY SER...
GGTCCAAATGCAAACGAGATGGGCGGGTCA...
              2050              2060         2070

...PHE THR HIS ASP THR ASP ASP SER LYS ALA
         ...TTTACACACGATACCGATGACAGTAAAGCC
              2080              2090              2100

SER VAL VAL PHE GLY THR LYS ARG GLN GLN...
TCTGTGGTCTTTGGCACAAAAAGACAACAA...
              2110              2120         2130

...GLU VAL LYS ***
         ...GAAGTTAAGTAG
              2140
```

FIG. 7A  Alignment of *M. catarrhalis* TbpB protein sequences

FIG.7B

```
          210       220       230       240       250
LSSLENKIFHSNDGTTKATTRDLKYVDYGYYLANDGNVLTVKTD--KLMNLGPVGGVFY        4223
...IKA.T...K.................V.A......NP...S...........          R1
...K..................Q.................V.......-E........        M35
QEKYKEL.ENAH.KKSD.RN...E..KS.FNYLSGYTATDHDK---.TNYR.YY.ALY.        LES1
KPIY.KN.NY.H.KQN..R......RS..IYRSGYSNIIP.----..IAKT.FD.AL..        Q8
KPIY.KN.ND.H.KQN..R......RS..IYRSGYSNIDIQK---..IAKT.FD.AL..        3
          260       270       280       290       300
NGTTTAKELPTQDAVKKGHWDFMTDVANRRNRFSEVKENSQA                        4223
.....................S....................KK........TY...        R1
...........................................KQ.........L..        M35
.....................K.SE....QTS.-....Y......ATLDNKYTDLPGIAR.T    LES1
..................Q..Q....Q..VSQ-........T......AKKGQSFS.FGTSQRL. Q8
..................K..Q....Q..VSE-........T......AKKGQSFS.FERRAGDR 3
          310       320       330       340       350
GMYYGASSKDEYNRLLIKEDSAPDGHSGEYCHSSEFTVNFKEKKLTGKLFSNIQDRH         4223
.W..........A.A...NY.................................E....S.     R1
.R.........D.KNK.ERYN................D.................E.....SR  M35
Q.-RSLV.T...AT...DKNNK.SDYN.A........D...AD..IK...I.QLSG-        LES1
.DR.S.M.YH..PS...D.KNK..NYN.................D.SK.S.K.E.S..I..G.   Q8
---SAM.H--..PS...DDKNK..NYND.................D.SK.S...G......H.   3
          360       370       380       390       400
KGNVTKTERYDIDANIHGNRFRGSATASNKNDTSK--HPFTSDAN                     4223
.QK....K....K.D...................D.AED..SK.........K            R1
........K........Y................D.AEA..TK.........K            M35
-TA..AK..K.E.D....................D.AED..TQ.........T            LES1
..S.N..K.........Y................DITTEA..SK.........K           Q8
..K....K......N.R.................I..DNE..AK.........D           3
```

FIG. 7C

```
         410       420       430       440       450
NRLEGGFYGPKGEEIAGKFLINDNKLFGVFGAKRESKAEEKTEAILDAYALGTFNISN
DK.........D..................Q.GNV-...........KPG         4223
.S........NA..................G................KNN         R1
.K.........D................D-V-................NT.        M35
.S........NA..................E.K...............KPG        LES1
...........D..................Q.E.K-............KSG        Q8
                                                            3

460       470       480       490       500
-ATT--FTPFTEKQLDNFGNAKKLVLGSTVIDLVPTDATK--NEFTK----         4223
-T.NPA..ANSK.E.....................DV....-----             R1
--...........K.....................GV..DV........          M35
K.--.....K.................N..S...-...........KFTK         LES1
-T.NPA..ANSK.E.....................G..DV...-----           Q8
-----.........IN...........TQG------D.V.TIDK                3

510       520       530       540       550
DKPESATNEAGETLMVNDEVSVKTYG--KNFEYLKFGELSIGGSHSVFLQGERTATTG
E..K...K..................................V..........     4223
N..D...K..........K.......YGR..............V.T.N......     R1
...T...K........I...........--..............V.D.......    M35
E..K...K..........I.......YGR..........................   LES1
E..ATT.Q...P.T...K.R.QVCC--S.L.H....S....D.N..........K.   Q8
                                                            3

560       570       580       590       600
E--KAVPTIGTAKYLGNWGYITGKDTGTGT--GKSFTDAQDVADEDI             4223
--................K............A.SSK.STD.G...K.I......    R1
--.................................S-----S...NE........   M35
--..................................-----A..-....NE...I.. LES1
--................K.................S-----......NE...I..  Q8
D.D..M.VA.N......R.T.A...VA.SGNTSKAYEAQQ.A.NANR.E..V       3
```

FIG.7D

```
        610       620       630       640       650
DFGNKSVSGKLITKGRQDPV--FSITGQIAGNGMTGTASTTKADAGGYKIDSSSTGKS
..EK...N...T..D......--....N..E.......K..AE.N............
..EK...K...T..D......--....N..D.......K..................
..ER...K...T.Q.T.....--..N.K.E.......K....................
..ER...K...T.Q.......--....N...........A..NV..............
..A....LT....PNTSS.GKSA.D..AT.D..FS.K.N.PDIET..L...KNSESG 660       670       680       690       700
-IVIKDANVTGGFYGPNANEMGGSFTHNA------DDSKASVVFGTKRQQEVK--*    4223
-........V..........T.......S----GN.G.V......K.-...K*      R1
-.............E.....T.......T----......E...-.*             M35
-....EN.E...........DT......-----------.E...-.*            LES1
-....EN.K...........DT-----------......                    Q8
RVIV...I.I.....Q..L...YKSNDAGNQDK..S......ARK......P*      3
```

FIG. 8A

*M. catarrhalis* strain 4223 *tbpA* - *orf3* - *tbpB* locus gene sequences

```
                                                        ...TCGGTGTATCAAAGTGCAAAAGCCAACAGG
GATGCCTGCCTTGTGATTGGTGGGTGTA...                                    50              60
         10          20          30
                                 40 tbpA
MET ASN GLN SER LYS GLN ASN....    ASN LYS SER LYS LYS SER LYS GLN VAL LEU....
...ACAAATCAAAACAAAAC...            ...AACAAATCCAAAACAAGTATTA...
             80                             100         110         120
   70                                                              
                              90

LYS LEU SER ALA LEU SER LEU GLY LEU LEU....    ASN ILE THR GLN VAL ALA LEU ALA ASN THR
AAACTTAGTGCCCTTGTCTTTGGGTCTGCTT...             ...AACATCACGCAGGTGGCACTGGCAAACACA
         130         140                                160         170         180
                              150

THR ALA ASP LYS ALA GLU ALA THR ASP LYS....    THR ASN LEU VAL VAL LEU ASP GLU THR
ACGGCCGATAAGGCGGAGGCAACAGATAAG...              ACAAACCTTGTTGTCTTGGATGAAACT
         190         200         210                   220         230         240
```

FIG.8B

```
VAL VAL THR ALA LYS LYS ASN ALA ARG LYS ....
GTTGTAACAGCGAAGAAAAACGCCCGTAAA...
         250              260           270...
                                    ... ALA ASN GLU VAL THR GLY LEU GLY LYS VAL
                                    ...GCCAACGAAGTTACAGGGCTTGGTAAGGTG
                                             280           290           300

VAL LYS THR ALA GLU THR ILE ASN LYS GLU ....
GTCAAAACTGCCGAGACCATCAATAAAGAA...
         310              320           330...
                                    ... GLN VAL LEU ASN ILE ARG ASP LEU THR ARG
                                    ...CAAGTGCTAAACATTCGAGACTTAACACGC
                                             340           350           360

TYR ASP PRO GLY ILE ALA VAL VAL GLU GLN ....
TATGACCCCTGGCATTGCTGTGGTTGAGCAA...
         370              380           390...
                                    ... GLY ARG GLY ALA SER SER GLY TYR SER ILE
                                    ...GGTCGTGGGGCAAGCTCAGGCTATTCTATT
                                             400           410           420

ARG GLY MET ASP LYS ASN ARG VAL ALA VAL ....
CGTGGTATGGATAAAAATCGTGTGGCGGTA...
         430              440           450...
                                    ... LEU VAL ASP GLY ILE ASN GLN ALA GLN HIS
                                    ...TTGGTTGATGGCATCAATCAAGCCCAGCAC
                                             460           470           480
```

FIG. 8C

```
TYR ALA LEU GLN GLY PRO VAL ALA GLY LYS ....              ASN TYR ALA ALA GLY GLY ALA ILE ASN GLU
TATGCCCTACAAGGCCCTGTGGCAGGCAAA...           ...AATTATGCCGCAGGTGGGGCAATCAACGAA
        490             500          510...                520          530          540

ILE GLU TYR GLU ASN VAL ARG SER VAL GLU ....              ILE SER LYS GLY ALA ASN SER SER GLU TYR
ATAGAATACGAAAATGTCCGCTCCGTTGAG...           ...ATTAGTAAAGGTGCAAATTCAAGTGAATAC
        550             560          570...                580          590          600

GLY SER GLY ALA LEU SER GLY SER VAL ALA ....              PHE VAL THR LYS THR ALA ASP ASP ILE ILE
GGCTCTGGGGCATTATCTGGCTCTGTGGCA...           ...TTTGTTACCAAAACCGCCGATGACATCATC
        610             620          630...                640          650          660

LYS ASP GLY LYS ASP TRP GLY VAL GLN THR ....              LYS THR ALA TYR ALA SER LYS ASN ASN ALA
AAAGATGGTAAAGATTGGGGCGTGCAGACC...           ...AAAACCGCCTATGCCAGTAAAAATAACGCA
        670             680          690...                700          710          720
```

FIG.8D

TRP VAL ASN SER VAL ALA ALA ALA GLY LYS ...
TGGGTTAATTCTGTGTGGCAGCAGCAGGCAAG...
730                              740               750...

... ALA GLY SER PHE SER GLY LEU ILE ILE TYR
...GCAGGTTCTTTTAGCGGTCTTATCATCTAC
      760                        770                780

THR ASP ARG ARG GLY GLN GLU TYR LYS ALA ....
ACCGACCGCCGTGGTCAAGAATACAAGGCA....
790                              800              810...

... HIS ASP ASP ALA TYR GLN GLY SER GLN SER
...CATGATGATGCCTATCAGGGTAGCCAAAGT
       820                      830              840

PHE ASP ARG ALA VAL ALA THR THR ASP PRO ....
TTTGATAGAGCGGTGGCAACCACTGACCCA....
850                              860             870...

... ASN ASN ARG THR PHE LEU ILE ALA ASN GLU
...AATAACCGAACATTTTTAATAGCAAATGAA
      880                       890               900

CYS ALA ASN GLY ASN TYR GLU ALA CYS ALA ....
TGTGCCAATGGTAATTATGAGGCGTGTGCT....
910                              920             930...

... ALA GLY GLY VAL GLN THR LYS LEU GLN ALA LYS
...GCTGGCGGGGTCAAACCAAACTTCAAGCCAAG
       940                      950               960

FIG.8E

```
PRO  THR  ASN  VAL  ARG  ASP  LYS  VAL  ASN  VAL....  LYS  ASP  TYR  THR  GLY  PRO  ASN  ARG  LEU  ILE
C C A A C C A A T G T G C G T G A T A A G G T C A A T G T C...  ...A A A G A T T A T A C A G G T C C T A A C C G C C T T A T C
         970                    980                                    990                      1000                       1010                       1020

PRO  ASN  PRO  LEU  THR  GLN  ASP  SER  LYS  SER....  LEU  LEU  LEU  ARG  PRO  GLY  TYR  GLN  LEU  ASN
C C A A A C C C A C T C A C C C A A G A C A G C A A A T C C...  ...T T A C T G C T T C G C C C A G G T T A T C A G C T A A A C
       1030                    1040                                    1050                      1060                       1070                       1080

ASP  LYS  HIS  TYR  VAL  GLY  GLY  VAL  TYR  GLU....  ILE  THR  LYS  GLN  ASN  TYR  ALA  MET  GLN  ASP
G A T A A G C A C T A T G T C G G T G G T G T A T G A A...  ...A T C A C C A A A C A A A A C T A C G C C A T G C A A G A T
       1090                    1100                                    1110                      1120                       1130                       1140

LYS  THR  VAL  PRO  ALA  TYR  LEU  ALA  VAL  HIS....  ASP  ILE  GLU  LYS  SER  ARG  LEU  SER  ASN  HIS
A A A A C C G T G C C T G C T T A T C T G G C G G T T C A T...  ...G A C A T T G A A A A A T C A A G G C T C A G C A A C C A T
       1150                    1160                                    1170                      1180                       1190                       1200
```

FIG. 8F

```
ALA  GLN  ALA  ASN  GLY  TYR  TYR  GLN  GLY  ASN....
GCCCAAGCCAATGGCTATTATCAAGGCAAT...
                                          1230...
         1210          1220
                                    ...ASN  LEU  GLY  GLU  ARG  ILE  ARG  ASP  THR  ILE
                                    ...AATCTTGGTGAACGCATTCGTGATACCATT
                                                                      1260
                                          1240          1250
                                    ...

GLY  PRO  ASP  SER  GLY  TYR  GLY  ILE  ASN  TYR....
GGGCCAGATTCAGGTTATGGCATCAACTAT...
                                          1290...
         1270          1280
                                    ...ALA  HIS  GLY  VAL  PHE  TYR  ASP  GLU  LYS  HIS
                                    ...GCTCATGGCGTATTTTATGATGAAAAACAC
                                                                      1320
                                          1300          1310
                                    ...

GLN  LYS  ASP  ARG  LEU  LEU  GLU  TYR  VAL....
CAAAAAGACCGCCTAGGGCTTGAATATGTT...
                                          1350...
         1330          1340
                                    ...TYR  ASP  SER  LYS  GLY  GLU  ASN  LYS  TRP  PHE
                                    ...TATGACAGCAAAGGTGAAAATAAATGGTTT
                                                                      1380
                                          1360          1370
                                    ...

ASP  ASP  VAL  ARG  VAL  SER  TYR  ASP  LYS  GLN....
GATGATGTGCGTGTGTCTTATGATAAGCAA...
                                          1410...
         1390          1400
                                    ...ASP  ILE  THR  LEU  ARG  SER  GLN  LEU  THR  ASN
                                    ...GACATTACGCTACGCCAGCTGACCAAC
                                                                      1440
                                          1420          1430
                                    ...
```

FIG.8G

```
THR HIS CYS SER THR TYR PRO HIS ILE ASP...
ACGCACTGTTCAACCTATCCGCACATTGAC...
       1450              1460              1470...
                      ...LYS ASN CYS THR PRO ASP VAL ASN LYS PRO
                      ...AAAAATTGTACGCCTGATGTCAATAAACCT
                              1480              1490              1500

PHE SER VAL LYS GLU VAL ASP ASN ASN ALA....
TTTTCGGTAAAAGAGGTGGATAACAATGCC....
       1510              1520              1530...
                      ...TYR LYS GLN HIS ASN LEU ILE LYS ALA
                      ...TACAAAGAACAGCACAATTAATCAAAGCC
                              1540              1550              1560

VAL PHE ASN LYS LYS MET ALA LEU GLY SER....
GTCTTTAACAAAAAAATGGCGTTGGGCAGT....
       1570              1580              1590...
                      ...THR HIS HIS ILE ASN LEU GLN VAL GLY
                      ...ACGCATCATCATCAACCTGCAAGTTGGC
                              1600              1610              1620

TYR ASP LYS PHE ASN SER SER LEU SER ARG....
TATGATAAATTCAATTCAAGCCTGAGCCGT....
       1630              1640              1650...
                      ...VAL GLU TYR ARG LEU ALA THR HIS GLN SER
                      ...GTAGAATATCGTTTGGCAACCCATCAGTCT
                              1660              1670              1680
```

FIG. 8H

```
TYR GLN LYS LEU ASP TYR THR PRO PRO SER....
TATCAAAAACTTGATTACACCCCACCAAGT...
         1690              1700             1710...
                       ...ASN PRO LEU PRO ASP LYS PHE LYS PRO ILE
                       ...AACCCTTTGCCAGATAAGTTAAGCCCCATT
                                   1720             1730           1740

LEU GLY SER ASN ASN LYS PRO ILE CYS LEU....
TTAGGTTCAAACAACAAACCCATTTGCCTT...
         1750              1760             1770...
                       ...ASP ALA TYR GLY TYR GLY HIS ASP HIS PRO
                       ...GATGCTTATGGTTATGGTCATGACCATCCA
                                   1780             1790           1800

GLN ALA CYS ASN ALA LYS ASN SER THR TYR....
CAGGCTTGTAACGCCAAAAACAGCACTTAT...
         1810              1820             1830...
                       ...GLN ASN PHE ALA ILE LYS LYS GLY ILE GLU
                       ...CAAAATTTTGCCATCAAAAAAGGCATAGAG
                                   1840             1850           1860

GLN TYR ASN GLN LYS THR ASN THR ASP LYS....
CAATACAACCAAAAAACCAATACCGATAAG...
         1870              1880             1890...
                       ...ILE ASP TYR GLN ALA ILE ILE ASP GLN TYR
                       ...ATTGATTATCAAGCCATCATTGACCAATAT
                                   1900             1910           1920
```

FIG. 8I

```
ASP LYS GLN ASN PRO ASN SER THR LEU LYS
GATAAACAAAACCCCAACAGCACCCTAAAA...
          1930          1940          1950...

PRO PHE GLU LYS ILE LYS GLN SER LEU GLY
...CCCTTTGAGAAAATCAAACAAAGTTTGGGG
          1960          1970          1980

GLN GLU LYS TYR ASN LYS ILE ASP GLU LEU
CAAGAAAAATACAACAAGATAGACGAACTT...
          1990          2000          2010...

GLY PHE LYS ALA TYR LYS ASP LEU ARG ASN
...GGCTTTAAAGCTTATAAAGATTTACGCAAC
          2020          2030          2040

GLU TRP ALA GLY TRP THR ASN ASP ASN SER
GAATGGGCGGGTTGGACTAATGACAACAGC...
          2050          2060          2070...

GLN GLN ASN ALA ASN LYS GLY THR ASP ASN
...CAACAAAATGCCAATAAAGGCACGGATAAT
          2080          2090          2100

ILE TYR GLN PRO ASN GLN ALA THR VAL VAL
ATCTATCAGCCAAATCAAGCAACTGTGGTC...
          2110          2120          2130...

LYS ASP ASP LYS CYS LYS TYR SER GLU THR
...AAAGATGACAAATGTAAATATAGCGAGACC
          2140          2150          2160
```

FIG. 8J

```
ASN SER TYR ALA ASP CYS SER THR THR ARG ...
AACAGCTATGCTGATTGCTCAACCACTCGC...
           2170              2180           2190
                                             ...HIS ILE SER GLY ASP ASN TYR PHE ILE ALA
                                             ...CACATCAGTGGTGATAATTATTTCATCGCT
                                                       2200              2210              2220

LEU LYS ASP ASN MET THR ILE ASN LYS TYR ...
TTAAAGACAACATGACCATCAATAAATAT...
           2230              2240           2250
                                             ...VAL ASP LEU GLY LEU GLY ALA ARG TYR ASP
                                             ...GTTGATTTGGGGCTGGGTGCTCGCTATGAC
                                                       2260              2270              2280

ARG ILE LYS HIS LYS SER ASP ALA SER ASN GLN LEU ...
AGAATCAAACACAAATCTGATGCCAGCAACCAGCTGTCT
           2290              2300           2310
                                             ...VAL ASP ASN SER ALA SER ASN GLN LEU
                                             ...GTAGACAACAGTGCCAGCAACCAGCTGTCT
                                                       2320              2330              2340

TRP ASN PHE GLY VAL VAL VAL LYS PRO THR ...
TGGAATTTTGGCGTGGTCGTCAAGCCCACC...
           2350              2360           2370
                                             ...ASN TRP LEU ASP ILE ALA TYR ARG SER SER
                                             ...AATTGGCTGGACATCGCTTATAGAAGCTCG
                                                       2380              2390              2400
```

FIG. 8K

```
GLN GLY PHE ARG MET PRO SER PHE SER GLU ...
CAAGGCTTTCGCATGCCAAGTTTTCTGAA...
         2410                2420                2430...

MET TYR GLY VAL ARG PHE GLY VAL THR ILE
                 ...ATGTATGGCGAACGCTTTGGCGTAACCATC
                         2440                2450                2460

GLY LYS GLY THR GLN HIS GLY CYS LYS GLY ....
GGTAAAGGCACGCAACATGGCTGTAAGGGT...
         2470                2480                2490....

LEU TYR TYR ILE CYS GLN THR VAL HIS
                 ...CTTTATTACATTTGTCAGCAGACTGTCCAT
                         2500                2510                2520

GLN THR LYS LEU LYS PRO GLU LYS SER PHE ....
CAAACCAAGCTAAAACCTGAAAAATCCTTT...
         2530                2540                2550....

ASN GLN GLU ILE GLY ALA THR LEU HIS ASN
                 ...AACCAAGAAATCGGAGCGACTTTACATAAC
                         2560                2570                2580

HIS LEU GLY SER LEU GLU VAL SER TYR PHE ....
CACTTAGGCAGTCTTGAGGTTAGTTATTTT...
         2590                2600                2610....

LYS ASN ARG TYR THR ASP LEU ILE VAL GLY
                 ...AAAAATCGCTATACCGATTTGATTGTTGGT
                         2620                2630                2640
```

FIG. 8L

```
LYS SER GLU GLU ILE ARG THR LEU THR GLN ...
AAAAGTGAAGAGATTAGAACCCTAACCCAA....
              2650                    2660                    2670...
                    ... GLY ASP ASN ALA GLY LYS GLN ARG GLY LYS
                    ...GGTGATAATGCAGGCAAAACAGCGTGGTAAA
                                2680                    2690                    2700

GLY ASP LEU GLY PHE HIS ASN GLY GLN ASP ....
GGTGATTTGGGCTTTCATAATGGACAAGAT....
              2710                    2720                    2730...
                    ... ALA ASP LEU THR GLY ILE ASN ILE LEU GLY
                    ...GCTGATTTGACAGGAATTAACATTCTTTGGC
                                2740                    2750                    2760

ARG LEU ASP LEU ASN ALA ALA ASN SER ARG ....
AGACTTGACCTAAACGCTGCCAATAGTCGC....
              2770                    2780                    2790...
                    ... LEU PRO TYR GLY LEU TYR SER THR LEU ALA
                    ...CTTCCCTATGGATTATACTCAACACTGGCT
                                2800                    2810                    2820

TYR ASN LYS VAL ASP VAL LYS GLY LYS THR ....
TATAACAAAGTTGATGTTAAAGGAAAAACC....
              2830                    2840                    2850...
                    ... LEU ASN PRO THR LEU ALA GLY THR ASN ILE
                    ...TTAAACCCAACTTTGGCAGGAACAAACATA
                                2860                    2870                    2880
```

FIG.8M

```
LEU PHE ASP ALA ILE GLN PRO SER ARG TYR ...
CTGTTTGATGCCATCCAGCCATCTCGTTAT...
              2890              2900              2910
      ... VAL VAL GLY LEU GLY TYR ASP ALA PRO SER
      ...GTGGTGGGCTTGGCTATGATGCCCCAAGC
              2920              2930              2940

GLN LYS TRP GLY ALA ALA ASN ALA ILE PHE THR ...
CAAAAATGGGGAGCAAACGCCATATTTACC...
              2950              2960              2970
      ... HIS SER ASP ALA LYS ASN PRO SER GLU LEU
      ...CATTCTGATGCCAAAAATCCAAGCGAGCTT
              2980              2990              3000

LEU ALA ASP LYS ASN LEU GLY ASN ...
TTGGCAGATAAGAACTTAGGTAATGGCAAC...
              3010              3020              3030
      ... ILE GLN THR LYS GLN ALA THR LYS ALA LYS
      ...ATTCAAACAAAACAAGCCACCAAAGCAAAA
              3040              3050              3060

SER THR PRO TRP GLN THR LEU ASP LEU SER ...
TCCACGCCGTGGCAAACACTTGATTTGTCA...
              3070              3080              3090
      ... GLY TYR VAL ASN ILE LYS ASP ASN PHE THR
      ...GGTTATGTAAACATAAAAGATAATTTTACC
              3100              3110              3120
```

FIG.8N

```
LEU ARG ALA GLY VAL TYR ASN VAL PHE ASN...
TTGCGTGCTGGCGTGTACAATGTATTTAAT...
        3130                    3140         3150....
                    ...THR TYR TYR THR THR TRP GLU ALA LEU ARG
                    ...ACCTATTACACCACTTGGGAGGCTTTACGC
                                3160                    3170         3180

GLN THR ALA LYS GLY ALA VAL ASN GLN HIS...
CAAACAGCAAAAGGGGCGGTCAATCAGCAT...
        3190                    3200         3210....
                    ...THR GLY LEU SER GLN ASP LYS HIS TYR GLY
                    ...ACAGGACTGAGCCAAGATAAGCATTATGGT
                                3220                    3230         3240

ARG TYR ALA ALA PRO GLY ARG ASN TYR GLN...
CGCTATGCCGCTCCCTGGACGCAATTACCAA...
        3250                    3260         3270....
                    ...LEU ALA LEU GLU MET LYS PHE ***
                    ...TTGGCACTTGAAATGAAGTTTTAACCAGTG
                                3280                    3290         3300

GCTTTGATGTGATTTTGGCATGCCAAATCC...
        3310                    3320         3330....
                    ...CAATCAACCAATGAATAAAGCCCCCATTAC
                                3340                    3350         3360
```

FIG. 80

```
CATGAGGGCTTTATTTTATCATCGCTGAGT....                                                                3390
             ...ATGCTCTTAGCGGTCATCACTCAGATTAGT 3420
                                            3400                      3410
CATTAATTTATTAGCGATTAATTTATTAGT....                                                                3450
             ...AATCACGCTGCTCTTTGATGATTTTAAGTG 3480
                                            3440                      3470
ATGGGTATTCAAGAACGATGTCATACTCAG....                                                                3510
             ...CACCGTTTTTATAGGCTTCTACTTCAAAGA 3540
                                            3500                      3530
CAGGCTTGCCTAAAAAGTCATCAACTTCTA....                                                                3570
             ...TATCGCCCGACTTGATAGCCACGAGCAGCAA 3600
                                            3560                      3590
GCATTTGAATGGCTTTTTTGACGATTTTGGG....                                                               3630
             ...CAAAGTTGCTGTCGCCATAAGGTTGTGCTT 3660
                                            3620                      3650
```

FIG.8P

TAATACGGTCGTTAGCAACTGCGGTGGTAG.... 3690 ....AGATACCAACGGCAGGCAACAAAACAGCAG 3720
3670                                      3700                                    3710

CACTTAGTACGCCAGCCAACAGTTTATTGG... 3740 ...TTAAATTTTCATAGTAGTTTCCTAATTAT 3780
3730                                     3750                                    3770

TATCATTGTAATTCATGTTTATCGTTATAA.... 3790 ...ACAAATCGTTATAAAATAACTGTGTCGTGATA 3840
                                         3800                                    3810                                    3830

ACCATTAATCACAAGTGGGTAAAATGCCTT.... 3850 ...TTGCCCAATGGCAAAATAGGCACAATGCTCT 3900
                                         3860                                    3870                                    3890

GCTTGTTCTATGATGGTCTATTATGATCAT.... 3910 ...CATTTTATTGACCTATTTTTTAATCGTAA 3960
                                         3920                                    3930                                    3950

FIG.8Q

```
TGTTTGTTTGATGTTAGTATAAATTTTATC...      ...AATCAAACAATCACAAATTATCAATCAT
         3970             3980         3990       4000            4010  4020

AGACGGTAAACAGGCTTCATATTTTACGCA...      ...TATTTCCCAGATGTCTGTAGTGTTTCATA
         4030             4040         4050       4060            4070  4080

GATGATTTGTAAAACAATTGTCGGTCATTA...      ...TTATCAATTGTAAAACTGATGGCTAATTTGT
         4090             4100         4110       4120            4130  4140

AACCTTATGGCTAAATGATAAATATGAATAAA...    ...GCGTTATACTGTATCAAAGAATGAGTAAAA
         4150             4160         4170       4180            4190  4200

ACCATCAATGGTATCTTATTTATCATCAGG...      ...TTGTGTTAATAAGATGCCAATTAAGCGACT
         4210             4220         4230       4240            4250  4260
```

FIG.8R

```
AATTTTGTAAATTAATTAATAATCATTCAT...
        4270                4280

...ATTTGTATTTTTAAATACCATAAAAATGG
                      4300          4310        4320 orf3
       MET LEU ALA PHE LEU ILE GLY ALA...
TAAAATATGCTCGCTTTTTTGATAGGAGCT...
        4330                4340

...VAL MET THR ILE THR PRO VAL TYR THR THR
              ...GTCATGACAATCACGCCTGTTTATACCACA
                      4360          4370        4380

PHE THR PRO THR LYS THR PRO ILE LYS PHE...
TTCACCCCCACCAAAACACCCATAAAATTT...
        4390                4400        4410

...PHE MET ALA GLY LEU THR PHE LEU ILE ALA
              ...TTTATGGCTGGCTTGACTTTTCTAATCGCT
                      4420          4430        4440

HIS ILE SER HIS ALA ASP ASP GLY ARG THR
CATATCAGCCATGCCGATGATGGTCGCACC...
        4450                4460        4470

...ASP ASN GLN LEU ILE GLU ASN GLN GLU ILE
              ...GACAATCAAGAGCTAATCAATCAAGAAATA
                      4480          4490        4500
```

FIG.8S

```
ALA  THR  LEU  GLU  PRO  ILE  ILE  ASN  HIS  ALA ....
G C C A C C C T T G A A C C C A T C A T T A A C C A T G C T ...
              4510                4520                4530...

...  GLN  PRO  GLU  LEU  LEU  SER  HIS  ASP  ALA  LEU
     ...  C A G C C T G A G T T A T T G T C C C A T G A T G C A T T A
                        4540                4550                4560

THR  PRO  LYS  ILE  GLU  PRO  ILE  LEU  LEU  ALA  GLN ....
A C A C C A A A A A T A G A A C C A A T A C T G G C A C A A ...
              4570                4580                4590...

...  THR  PRO  ASN  PRO  ALA  GLU  ASP  THR  LEU  ILE
     ...  A C A C C A A A T C C T G C C G A A G A T A C G C T C A T C
                        4600                4610                4620

ALA  ASP  GLU  ALA  LEU  LEU  LEU  ASP  ASN  PRO ....
G C C G A T G A G G C G T T A C T G C T T G A T A A C C C T ...
              4630                4640                4650...

...  ASP  LEU  LEU  ASN  HIS  ALA  LEU  ASN  SER  ALA
     ...  G A T T T G C T C A A T C A C G C C C T A A A T T C T G C T
                        4660                4670                4680

VAL  MET  THR  ASN  HIS  MET  ALA  GLY  VAL  HIS ....
G T C A T G A C C A A T C A T A T G G C A G G C G T T C A C ...
              4690                4700                4710...

...  ALA  LEU  LEU  PRO  ILE  TYR  GLN  LYS  LEU  PRO
     ...  G C A T T A T T G C C C A T T T A T C A A A A A C T G C C C
                        4720                4730                4740
```

FIG.8T

LYS ASP HIS GLN ASN GLY ILE LEU LEU GLY               TYR ALA ASN ALA LEU ALA ALA LEU ASP LYS
AAAGACCATCAAAAATGGCATTTTACTTTGGG...   ...TATGCCAATGCCCTTGGCTGCCTTTGGATAAG
         4750             4760              4770              4780              4790              4800

GLY ASN ALA LYS LYS ALA ILE ASP GLU LEU               ARG ARG ILE ILE ALA ILE MET PRO GLU TYR
GGCAACGCCAAAAAAGCCATTGATGAGCTA...   ...CGTCGCATCATCGCCATCATGCCTGAATAT
         4810             4820              4830              4840              4850              4860

ASN VAL VAL ARG PHE HIS LEU ALA ARG ALA               LEU PHE MET ASP LYS GLN ASN GLU ALA ALA
AATGTGGTGCGTTTCATCTGGCAAGGGCA...   ...TTATTTATGGACAAAACAAAATGAAGCCGCC
         4870             4880              4890              4900              4910              4920

LEU ASP GLN PHE ASN LYS LEU HIS ALA ASP               ASN LEU PRO GLU GLU VAL ARG GLN VAL VAL
CTTGACCAGTTTAATAAATTACATGCTGAC...   ...AACTTGCCAGAGGAGGTGCGGCAGGTTGTT
         4930             4940              4950              4960              4970              4980

FIG.8U

```
GLY  GLN  TYR  ARG  GLN  ALA  LEU  LYS  GLN  ARG...         ASP  SER  TRP  THR  TRP  GLN  VAL  GLY  MET  ASN
GGG CAG TAC AGA CAG GCA CTA AAA CAA CGA...     ...GAT TCA TGG ACA TGG CAA GTA GGC ATG AAT
              4990                    5000                           5010                      5020                         5030                       5040

LEU  ALA  LYS  GLU  ASP  ASN  ILE  ASN  GLN  THR....        PRO  LYS  ASN  THR  THR  GLN  GLY  GLN  TRP  THR
CTG GCC AAA GAA GAC AAC ATC AAT CAA ACC...  ...CCC AAA AAC ACC ACG CAA GGT CAA TGG ACT
              5050                      5060                         5070                      5080                        5090                        5100

PHE  ASP  LYS  PRO  ILE  ASP  ALA  ILE  THR  LEU....        SER  TYR  GLN  LEU  GLY  ALA  ASP  LYS  LYS  TRP
TTT GAC AAA CCC ATT GAC GCC ATT CAC CCT A...  ...AGC TAC CAA TTG GGG GCG GAT AAA AGT GG
              5110                     5120                         5130                         5140                       5150                        5160

SER  LEU  PRO  LYS  GLY  ALA  TYR  VAL  GLY  ALA....        ASN  ALA  GLN  ILE  TYR  GLY  LYS  HIS  HIS  GLN
TCT TTG CCC AAA GGG GCA TAT GTG GGG AGC G...  ...AAC GCC CAA ATC TAT GGC AAA CAT CAT CAA
              5170                      5180                         5190                     5200                        5210                         5220
```

FIG.8V

```
ASN HIS LYS LYS TYR ASN ASP HIS TRP GLY ....
A A T C A C A A A A A T A C A A C G A C C A T T G G G G C ....
                5230                      5240                    5250....
                                            ... A G A C T G G G G G C A A A T T T G G G C T T T G C T G A T
                                                            5260                    5270                  5280
    ... ARG LEU GLY ALA ASN LEU GLY PHE ALA ASP

ALA LYS LYS ASP LEU SER ILE GLU THR TYR ....
G C C A A A A A A G A C C T T A G C A T T G A G A C C T A T ....
                5290                      5300                    5310....
                                            ... G G T G A A A A A G A T T T T A T G G G C A T G A G C G T
                                                            5320                    5330                  5340
    ... GLY GLU LYS ARG PHE TYR GLY HIS GLU ARG

TYR THR ASP THR ILE GLY ILE ARG MET SER ....
T A T A C C G A C A C C A T T G G C A T A C G C A T G T C G ....
                5350                      5360                    5370....
                                            ... G T T G A T T A T A G A A T C A A C C A A A A T T T C A A
                                                            5380                    5390                  5400
    ... VAL ASP TYR ARG ILE ASN PRO LYS PHE GLN

SER LEU ASN ALA ILE ASP ILE SER ARG LEU ....
A G C C T A A A C G C C A T A G A C A T A T C A C G C C T A ....
                5410                      5420                    5430....
                                            ... A C C A A C C A T C G G A C G C C T A G G G C T G A C A G T
                                                            5440                    5450                  5460
    ... THR ASN HIS ARG THR PRO ARG ALA ASP SER
```

FIG.8W

```
ASN ASN THR LEU TYR SER THR SER LEU ILE           TYR TYR PRO ASN ALA THR ARG TYR TYR LEU
AATAACACTTTATACAGTACCTCATTGATT...           ...TATTACCCAAATGCCACACGCTATTATCTT
        5470                 5490                        5500          5510          5520

LEU GLY ALA ASP PHE TYR ASP GLU LYS VAL           PRO GLN ASP PRO SER ASP SER TYR GLN ARG
TTGGGGGCAGACTTTTATGATGAAAAAGTG...           ...CCACAAGACCCATCTGACAGTTATCAACGC
        5530                 5550                        5560          5570          5580

ARG GLY ILE ARG THR ALA TRP GLY GLN GLU           TRP ALA GLY GLY LEU SER SER ARG ALA GLN
CGTGGCATACGCACAGCGTGGGGCAAGAA...           ...TGGGCGGGGGTGGTCTTTCAAGCCGTGCCCAA
        5590                 5610                        5620          5630          5640

ILE SER ILE ASN LYS ARG HIS TYR GLN GLY           ALA ASN LEU THR SER GLY GLY GLN ILE ARG
ATCAGCATCAACAAACGCCATTACCAAGGG...           ...GCAAACCTAACCAGCGGTGGACAAATTCGC
        5650                 5670                        5680          5690          5700
```

FIG.8X

HIS ASP LYS GLN MET GLN ALA SER LEU SER ...
CATGATAAACAGATGCAAGCCGTCTTTATCG... 5730...
          5720

LEU TRP HIS ARG ASP ILE HIS LYS TRP GLY
...CTTTGGCACAGAGACATTCACAAATGGGGC 5760
         5740     5750

ILE THR PRO ARG LEU THR ILE SER THR ASN ...
ATCACGCCACGGCTGACCATCAGCACAAAC... 5790...
         5770   5780

ILE ASN LYS SER ASN ASP ILE LYS ALA ASN
...ATCAATAAAGCAATGACATTCAAGGCAAAT 5820
     5800     5810

TYR HIS LYS ASN GLN MET PHE VAL GLU PHE ...
TATCACAAAAATCAAATGTTTGTTGAGTTT... 5850...
         5830   5840

SER ARG ILE PHE ***
...AGTCGCATTTTTTTGATGGGATAAGCACGCC 5880
      5860    5870

CTACTTTTGTTTTTGTAAAAAAATGTGCCA... 5910...
     5890     5900

...TCATAGACAATATCAAGAAAAATCAAGAA 5940
    5920     5930

FIG.8Y

```
AAAAAGATTACAAATTTAATGATAATTGTT....ATTGTTTATGTTATTTATTTATCAATGTAAA
     5950                5960              5970           5980              5990          6000

TTTGCCGTATTTTGTCTATCATAAATGCAT....TTATCAAATGCTCAAAATAAATACGCCAAAT
     6010                6020              6030           6040              6050          6060

GCACATTGTCAGCATGCCAAAATAGGCATC....AACAGACTTTTTAGATAATACCATCAACC
     6070                6080              6090           6100              6110          6120 tbpB
                                          MET LYS HIS ILE
CATCAGAGGATTATTTTATGAAAACACATTC....PRO LEU THR THR LEU CYS VAL ALA ILE SER  A
     6130                6140              6150         CTTTAACCACACTGTGTGGCAATCTCTG
                                                         6160              6170          6180
```

FIG.8Z

```
LA  VAL LEU LEU THR ALA CYS GLY GLY SER                                                       ...
    CCGTCTTATTAACCGCTTGTGGTGGCAGTG                                                             ...
              6190                  6200                 6210
                                          ...GLY GLY SER ASN PRO PRO ALA PRO THR PRO  I
                                          ...GTGGTTCAAATCCACCTGCTCCTACGCCCA
                                                  6220                  6230               6240

LE  PRO ASN ALA SER GLY SER GLY ASN THR                                                       ...
    TTCCAAATGCTAGCGGGTTCAGGTAATACTG                                                            ...
              6250                  6260                 6270
                                          ...GLY ASN THR GLY ASN ALA GLY GLY THR ASP  A
                                          ...GCAACACTGGTAATGCTGGCGGTACTGATA
                                                  6280                  6290               6300

SN  THR ALA ASN ALA GLY ASN THR GLY GLY                                                       ...
    ATACAGCCAATGCCAATGCAGGTAATACAGGCGGTA                                                       ...
              6310                  6320                 6330
                                          ...THR ASN SER GLY THR GLY SER ALA ASN THR  P
                                          ...CAAACTCTGGTACAGGCAGTGCCAACACAC
                                                  6340                  6350               6360

RO  GLU PRO LYS TYR GLN ASP VAL PRO THR                                                       ...
    CAGAGCCAAAATATCAAGATGTACCAACTG                                                             ...
              6370                  6380                 6390
                                          ...GLU LYS ASN GLU LYS ASP LYS VAL SER SER  I
                                          ...AGAAAAATGAAAAAGATAAAGTTTCATCCA
                                                  6400                  6410               6420
```

FIG.8A'

```
LE  GLN GLU PRO ALA MET GLY TYR GLY MET ....        ALA LEU SER LYS ILE ASN LEU HIS ASN ARG G
TTCAAGAACCTGCCATGGGTTATGGCATGG....              ...CTTTGAGTAAAATTAATCTACACAACCGAC
            6430              6440        6450          ...                6460              6470              6480

LN  ASP THR PRO LEU ASP GLU LYS ASN ILE ....        ILE THR LEU ASP GLY LYS LYS GLN VAL ALA G
AAGACACGCCATTAGATGAAAAAAATATCA....              ...TTACCTTAGACGGTAAAAACAAGTTGCAG
            6490              6500        6510          ...                6520              6530              6540

LU  GLY LYS LYS SER PRO LEU PRO PHE SER ....        LEU ASP VAL GLU ASN LYS LEU LEU ASP GLY T
AAGGTAAAAAAATCGCCATTGCCATTTTCGT....             ...TAGATGTAGAAAATAAATTGCTTGATGGCT
            6550              6560        6570          ...                6580              6590              6600

YR  ILE ALA LYS MET ASN VAL ALA ASP LYS ....        ASN ALA ILE GLY ASP ARG ILE LYS LYS GLY A
ATATAGCAAAAATGAATGTAGCGGATAAAA....              ...ATGCCATTGGTGACAGAATTAAGAAAGGTA
            6610              6620        6630          ...                6640              6650              6660
```

FIG. 8B'

```
SN  LYS GLU ILE SER ASP GLU LEU ALA ...                       ...LYS GLN ILE LYS GLU ALA VAL ARG LYS SER H
A T A A A G A A A T C T C C G A T G A A G A A C T T G C C A...   ...A A C A A A T C A A A G A A G C T G T G C G T A A A A G C C
                    6670                        6680                                  6700                      6710                        6720
                                                              6690

IS  GLU PHE GLN GLN VAL LEU SER SER LEU ...                   ...GLU ASN LYS ILE PHE HIS SER ASN ASP GLY T
A T G A G T T T C A G C A A G T A T T A T C A T C A C T G G...   ...A A A A C A A A A A T T T T C A T T C A A T G A C G G A A
                    6730                        6740                                  6760                      6770                        6780
                                                              6750

HR  THR LYS ALA THR THR ARG ASP LEU LYS ...                   ...TYR VAL ASP TYR GLY TYR TYR LEU ALA ASN A
C A A C C A A A G C A A C C A C G A G A T T A A A A T...         ...A T G T T G A T T A T G G T T A C T A C T T G G C G A A T G
                    6790                        6800                                  6820                      6830                        6840
                                                              6810

SP  GLY ASN TYR LEU THR VAL LYS THR ASP ...                   ...LYS LEU TRP ASN LEU GLY PRO VAL GLY GLY V
A T G G C A A T T A T C T A A C C G T C A A A A C A G A C A...   ...A A C T T T G G A A T T T A G G C C C T G T G G G T G
                    6850                        6860                                  6880                      6890                        6900
                                                              6870
```

FIG. 8C'

```
AL  PHE  TYR  ASN  GLY  THR  THR  ALA  LYS  ...  GLU  LEU  PRO  THR  GLN  ASP  ALA  VAL  LYS  TYR  L
TGTTTTTATAATGGCACAACGACCGCCAAAG...AGTTGCCCACACAAGATGCGGTCAAATATA
        6910                        6920            6930...      6940              6950              6960

YS  GLY  HIS  TRP  ASP  PHE  MET  THR  ASP  VAL  ...  ALA  ASN  ARG  ARG  ASN  ARG  PHE  SER  GLU  VAL  L
AAGGACATTGGGGACTTTATGACCGATGTTG....CCAAACAGAAGAAACCGATTTAGCGAAGTGA
        6970                        6980            6990...      7000              7010              7020

YS  GLU  ASN  SER  GLN  ALA  GLY  TRP  TYR  TYR  ...  GLY  ALA  SER  SER  LYS  ASP  GLU  TYR  ASN  ARG  L
AAGAAAACTCTCAAGCAGGCTGGTATTATG...GAGCATCTTCAAAAGATGAATACAACCGCT
        7030                        7040            7050...      7060              7070              7080

EU  LEU  THR  LYS  GLU  ASP  SER  ALA  PRO  ASP  ...  GLY  HIS  SER  GLY  GLU  TYR  GLY  HIS  SER  SER  G
TATTAAACTAAAGAAGACTCTGCCCCTGATG...GTCATAGCGGTGAATATGGCCATAGCAGTG
        7090                        7100            7110...      7120              7130              7140
```

FIG.8D'

```
LU  PHE  THR  VAL  ASN  PHE  LYS  GLU  LYS  LYS
AGTTTACTGTTAAATTTTAAGGAAAAAAAT....
         7150                  7160                            7170....
              ..LEU  THR  GLY  LYS  LEU  PHE  SER  ASN  LEU  GLN  A
              ...TAACAGGTAAGCTGTTTAGTAACCTACAAG
                        7180                 7190                        7200

SP  ARG  HIS  LYS  GLY  ASN  VAL  THR  LYS  THR
ACCGCCATAAGGGCAATGTTACAAAAACCG...
         7210                  7220                            7230....
              ..GLU  ARG  TYR  ASP  ILE  ASP  ALA  ASN  ILE  HIS  G
              ...AACGCTATGACATCGATGCCAATATCCACG
                        7240                 7250                        7260

LY  ASN  ARG  PHE  ARG  GLY  SER  ALA  THR  ALA
GCAACCGCTTCCGTGGCAGTGCCACCGCAA...
         7270                  7280                            7290....
              ..SER  ASN  LYS  ASN  ASP  THR  SER  LYS  HIS  PRO  P
              ...GCAATAAAAAATGACACAAGCAAACACCCCT
                        7300                 7310                        7320

HE  THR  SER  ASP  ALA  ASN  ARG  ASN  ARG  LEU  GLU
TTACCAGTGATGCCAACAATAGGCTAGAAG...
         7330                  7340                            7350....
              ..GLY  PHE  TYR  GLY  LYS  GLY  PRO  LYS  GLY  GLU  L
              ...GTGGTTTTTATGGGCCAAAAGGCGAGGAGC
                        7360                 7370                        7380
```

FIG. 8E'

```
EU  ALA GLY LYS PHE LEU THR ASN ASP ASN            ...LYS LEU PHE GLY VAL PHE GLY ALA LYS ARG G
    TGGCAGGTAAATTCTTAACCAATGACAACA....              ...AACTCTTTGGCGTCTTTGGTGCTAAACGAG
                      7390              7400                    7410     7420      7430     7440

LU  SER LYS ALA GLU GLU LYS THR GLU ALA            ...ILE LEU ASP ALA TYR ALA LEU GLY THR PHE A
    AGAGTAAAGCTGAGGAAAAACCGAAGCCA....               ...TCTTAGATGCCTATGCACTTGGGACATTTA
                      7450              7460                    7470     7480      7490     7500

SN  THR SER ASN ALA THR PHE THR PRO                ...PHE THR GLU LYS GLN LEU ASP ASN PHE GLY A
    ATACAAGTAACGCAACCACATTCACCCCAT....              ...TTACCGAAAAACAACTGGATAACTTTGGCA
                      7510              7520     7530          7540      7550      7560

SN  ALA LYS LYS LEU VAL LEU GLY SER THR            ...VAL ILE ASP LEU VAL PRO THR ASP ALA THR L
    ATGCCAAAAAATTGGTCTTAGGTTCTACCG....              ...TCATTGATTTGGTGCCTACTGATGCCACCA
                      7570              7580     7590          7600      7610      7620
```

FIG.8F'

```
YS  ASN GLU PHE THR LYS ASP LYS PRO GLU ...
    AAAATGAATTCACCAAAGACAAGCCAGAGT...
                    7630          7640          7650
         ...SER ALA THR ASN GLU ALA GLY GLU THR LEU M
         ...CTGCCACAAACGAAGCGGGCGGGCGAGACTTTGA
                    7660          7670          7680

ET  VAL ASN ASP GLU VAL SER VAL LYS THR ...
    TGGTGAATGATGAAGTTAGCGTCAAAACCT...
                    7690          7700          7710
         ...TYR GLY LYS ASN PHE GLU TYR LEU LYS PHE G
         ...ATGGCAAAAACTTTGAATACCTAAAATTTG
                    7720          7730          7740

LY  GLU LEU SER ILE GLY GLY SER HIS SER ...
    GTGAGCTTAGTATCGGTGGTAGCCATAGCG...
                    7750          7760          7770
         ...VAL PHE LEU GLN GLY ARG THR ALA THR T
         ...TCTTTTTACAAGGCGAACGCACCGCTACCA
                    7780          7790          7800

HR  GLY GLU LYS ALA VAL PRO THR THR GLY ...
    CAGGCGAGAAAGCCGTACCAACCACAGGCA...
                    7810          7820          7830
         ...THR ALA LYS TYR LEU GLY ASN TRP VAL GLY T
         ...CAGCCAAATATTTGGGGAACTGGGTAGGAT
                    7840          7850          7860
```

FIG. 8G'

```
YR  ILE THR GLY LYS ASP THR GLY THR GLY
    ACATCACAGGAAAAGGACACAGGAACGGGCA...
                 7870              7880           7890....

...THR GLY LYS SER PHE THR ASP ALA GLN ASP V
              ...CAGGAAAAAGCTTTACCGATGCCCAAGATG
                          7900          7910          7920

AL  ALA ASP PHE ASP ILE ASP PHE GLY ASN
    TTGCTGATTTTGACATTGATTTTGGAAATA...
                 7930              7940          7950....

...LYS SER VAL SER GLY LYS LEU ILE THR LYS G
              ...AATCAGTCAGCGGTAAACTTATCACCAAAG
                          7960          7970          7980

LY  ARG GLN ASP PRO VAL PHE SER ILE THR
    GCCGCCAAGAGACCCTGTATTTAGCATCACAG...
                 7990              8000          8010....

...GLY GLN ILE ALA GLY ASN GLY TRP THR GLY T
              ...GTCAAATCGCAGGCAATGGCTGGACAGGGA
                          8020          8030          8040

HR  ALA SER THR THR LYS ALA ASP ALA GLY
    CAGCCAGCACCACCAAAAGCGGACGCAGGAG...
                 8050              8060          8070....

...GLY TYR LYS ASP SER ILE SER SER THR GLY L
              ...GCTACAAGATAGATTCTAGCAGTACAGGCA
                          8080          8090          8100
```

FIG.8H'

```
YS  SER  ILE  ALA  ILE  LYS  ASP  ALA  ASN  VAL  ....
    A A T C C A T C G C C A T C A A A G A T G C C A A T G T T A....
                            8110                        8130....
                                                            ...THR GLY GLY PHE TYR GLY PRO ASN ALA ASN  G
                                                            ...C A G G G G G C T T T T A T G G T C C A A A T G C A A A C G
                                                                      8140                    8150              8160
                                                                                                                    ...

LU  MET GLY GLY SER PHE THR HIS ASN ALA  ....
    A G A T G G G C G G G T C A T T T A C A C A A C G C C G....
              8170                      8190....
                                                    ...ASP ASP SER LYS ALA SER VAL VAL PHE GLY  T
                                                    ...A T G A C A G C A A A G C C C T C T G T G G T C T T T G G C A
                                                            8200                    8210                    8220

HR  LYS ARG GLN GLN GLU VAL LYS ***
    C A A A A A G A C A A C A A G A A G T A A G T A G T A A T....
                  8230                          8250....
                                                            ...T T A A A C A C A A T G T T T G
                                                                    8260
```

FIG.9A

Alignment of M. catarrhalis ORF3 proteins

```
         10        20        30        40        50
MLAFLIGAVMITPVYTTFTPTKTPTKFFMAGLTFLIAHISHADDGRTDN
..................................................

60        70        80        90       100
         .P........................G...T.................         Q8
         QELINQETATLEPIINHAQPELLSHDALTPKIEPTLAQTPNPAEDTLIAD        4223

110       120       130       140       150
EALLLDNPDLLNHALNSAVMTNHMAGVHALLPIYQKLPKDHQNGILLGYA
........N.........................................

160       170       180       190       200
         NALAAIDKGNAKKAIDELRRIIAIMPEYNVVRFHLARALFMDKQNEAALD        4223
         ....V..........A..G...............................         Q8

210       220       230       240       250
QFNKLHADNLPEEVRQVVGQYRQALKQRDSWMQVGMNLAKEDNINQTPK
.........R........................................

260       270       280       290       300
         NTTQGQMTFDKPIDATTLSYQLGADKKWSLPKGAYVGANAQIYGKHHQNH        4223
         ..................................................         Q8

310       320       330       340       350
KKYNDHWGRLGANLGFADAKKDLSIETYGEKRFYGHERYTDTIGIRMSVD
...............................A..................

360       370       380       390       400
         YRINPKFQSLNAIDISRLTNHRTPRADSNNTLYSTSLIYYPNATRYYLLG        4223
         ..................................................         Q8
```

FIG.9B

```
         410       420       430       440       450
ADFYDEKVPQDPSDSYQRRGIRTAMQQEMAGGLSSRAQISINKRHYQGAN
                              E
                                      460       470       480       490       500
                              LTSGQIRHDKQMQASLSLMHRDIHKWGITPRLTISTNINKSNDIKANYH    4223
                                            Q                                       Q8

510                                                                                4223
KNQMFVEFSRIF*                                                                       Q8
    *
```

TRANSFERRIN RECEPTOR GENES OF MORAXELLA

REFERENCE TO RELATED APPLICATIONS

This application is a national phase application under 35 U.S.C. 371 of PCT/CA99/00307 filed Apr. 12, 1999.

FIELD OF INTVENTION

The present inventoin relates to the molecules cloning of genes encoding transferrin receptor (TfR) proteins and, in particular, to the cloning of transferrin receptor genes from *Moraxella (Branhamella) catarrhalis*.

BACKGROUND OF THE INVENTION

*Moraxella (Branhamella) catarrhalis* bacteria are Gram-negative diplococcal pathogens which are carried asymptomatically in the healthy human respiratory tract. In recent years, *M. catarrhalis* has been recognized as an important causative agent of otitis media. In addition, *M. catarrhalis* has been associated with sinusitis, conjunctivitis, and urogenital infections, as well as with a number of inflammatory diseases of the lower respiratory tract in children and adults, including pnuemonia, chronic bronchitis, tracheitis, and emphysema (refs. 1 to 8). (Throughout this application, various references are cited in parentheses to describe more fully the state of the art to which this invention pertains. Full bibliographic information for each citation is found at the end of the specification, immediately preceding the claims. The disclosures of these references are hereby incorporated by reference into the present disclosure). Occasionally, *M. catarrhalis* invades to cause septicaemia, arthritis, endocarditis, and meningitis (refs 9 to 13).

Otitis media is one of the most common illnesses of early childhood and approximately 80% of all children suffer at least one middle ear infection before the age of three (ref. 14). Chronic otitis media has been associated with auditory and speech impairment in children, and in some cases, has been associated with learning disabilities. Conventional treatments for otitis media include antibiotic administration and surgical procedures, including tonsillectomies, adenoidectomies, and tympanocentesis. In the United States, treament costs for otitis media are estimated to be between one and two billion dollars per year.

In otitis media cases, *M. catarrhalis* commonly is co-isolated from middle ear fluid along with *Streptococcus pneumoniae* and non-typable *Haemophilus influenzae*, which are believed to be responsible for 50% and 30% of otitis media infections, respectively. *M. catarrhalis* is believed to be responsible for approximately 20% of otitis media infections (ref. 15). Epidemiological reports indicate that the number of cases of otitis media attributable to *M. catarrhalis* is increasing, along with the number of antibiotic-resistant isolates of *M. catarrhalis*. Thus, prior to 1970, no β-lactamase-producing *M. catarrhalis* isolates had been reports, but since the mid-seventies, and incresing number of β-lactamase-expressing isolates have been detected. Recent surveys suggest that 75% of clinical isolates produce β-lactamase (ref. 16, 26).

Iron is an essential nutrient for the growth of many bacteria. Several bacterial species, including *M. catarrhalis*, obtain iron from the host by using transferring receptor proteins to captures transferrin. A number of bacteria including *Neisseria meningitidis* (ref. 17), *N. gonorrhoeae* (ref. 18), *Haemophilus influenzae* (ref. 19), as well as *M. catarrhalis* (ref. 20), produce outer membrane proteins which specifically bind human transferrin. The expression of these proteins is regulated by the amount of iron in the environment.

The two transferrin receptor proteins of *M. catarrhalis*, designated transferrin binding protein 1 (Tbp1) and transferrin binding protein 2 (Tbp2), have molecular weights of 115 kDa (Tbp1) and approximately 80 to 90 kDa (Tbp2). Unlike the transferrin receptor protein of other bacteria which have an affinity for apotransferrin, the *M. catarrhalis* Tbp2 receptors have a preferred affinity for iron-saturated (i.e., ferri-) transferrin (ref. 21).

*M. catarrhalis* infection may lead to serious disease. It would be advantageous to provide a recombinant source of transferrin binding proteins as antigens in immunogenic preparations including vaccines, carriers for other antigens and immunogens and the generation of diagnostic reagents. The genes encoding transferrin binding proteins and fragments thereof are particularly desirable and useful in the specific identification and diagnosis of *Moraxella* and for immunication against disease caused by *M. catarrhalis* and for the generation of diagnositc reagents.

There had previously been described in published PCT appliation WO 97/32380, assigned to Connaught Laboratories Limited, the assignee hereof, the cloning, subcloning and sequencing of nucleic acid molecules encoding transferrin receptor proteins Tbp1 and Tbp2 of certain specific strains of *Moraxella catarrhalis*, namely *M. catarrhlais* strains 4223, Q8 and R1, as well as identifying the deduced amino acid sequences of the encoded Tbp1 and Tbp2 proteins.

WO 97/32380 further describes the construction of expression plasmids for the production of recombinant Tbp1 from *M. catarrhalis* strain 4223 and of recombinant Tbp2 from *M. catarrhalis* strains 4223 and Q8, the recombinant expression of such proteins in *E. coli*, and the extraction and purification of the expressed Tbp1 and Tbp2 proteins.

SUMMARY OF THE INVENTION

The present invention is directed towards the provision of purified and isolated nucleic acid molecules encoding the transferrin receptor protein Tbp2 of additional strains of *Moraxella catarrhalis*, namely strains M35, 3 and LES1. As in the case of WO 97/32380, the respective genes encoding the Tbp1 and Tbp2 proteins are identified as *tbpA* and *tbpB* genes.

The nucleic acid molecules provided herein are useful for the specific detection of strains of *Moraxella* and for diagnosis of infection by *Moraxella*. The purified and isolated nucleic acid molecules provided herein, such as DNA, are also useful for expressing the *tbp* genes by recombinant DNA means for providing, in an economical manner, purified and isolated transferrin receptor proteins as well as subunits, fragments or analogs thereof.

The transferrin receptor, subunits or fragments thereof or analogs thereof, as well as nucleic acid molecules encoding the same and vectors containing such nucleic acid molecules, are useful in immunogenic compositions for vaccinating against diseases caused by *Moraxella*, the diagnosis of infection by *Moraxella* and as tools for the generation of immunological reagents.

Monoclonal antibodies or mono-specific antisera (antibodies) raised against the transferrin receptor protein, produced in accordance with aspects of the present invention, are useful for the diagnosis of infection by *Moraxella*, the specific detection of *Moraxella* (in, for example, in vitro and in vivo assays) and for the treatment of diseases caused by *Moraxella*.

In accordance with one aspect of the present invention, there is provided a purified and isolated nucleic acid molecule encoding transferrin receptor protein Tbp2 of a strain of *Moraxella*, specifically *M. catarrhalis* strain M35, 3 or LES1.

In one preferred embodiment of the invention, the nucleic acid molecule may encode only the Tbp2 protein of the *Moraxella* strain.

The purified and isolated nucleic acid molecule preferably has a DNA sequence selected from the group consisting of (a) a DNA sequence as set out in FIGS. 2, 4 or 6 (SEQ ID NOS: 1, 3 or 5) or the complementary DNA sequence thereto; (b) a DNA sequence encoding an amino acid sequence as set out in FIGS. 2, 4 or 6 (SEQ ID NOS: 2, 4 or 6) or the complementary DNA sequence thereto.

In an additional aspect, the present invention includes a vector adapted for transformation of a host, comprising a nucleic acid molecule as provided herein. Such vector may further comprise expression means operatively coupled to the nucleic acid molecule for expression by the host of the Tbp2 protein of the respective strain of *M. catarrhalis*.

The expression means may include a promoter and a nucleic acid portion encoding a leader sequence for secretion from the host of the transferrin receptor protein. The expression means also may include a nucleic acid portion encoding a lipidation signal for expression from the host of a lipidated form of the transferrin receptor protein or the fragment. The host transformed by the expression vector may be selected from, for example, *Escherichia coli, Bordetella, Bacillus, Haemophilus, Moraxella*, fungi, yeast or baculovirus and Semliki Forest virus expression systems may be used.

In an additional aspect of the invention, there is provided a transformed host containing an expression vector as provided herein. The invention further includes a recombinant Tbp2 protein of the specific strains of *Moraxella catarrhalis* and producible by the transformed host. Such recombinant Tbp2 proteins have a deduced amino acid sequence selected from the group consisting of those shown in FIGS. 2, 4 or 6 (SEQ ID NOS: 2, 4 or 6).

Such recombinant transferrin receptor protein may be provided in substantially pure form according to a further aspect of the invention, which provides a method of forming a substantially pure recombinant Tbp2 protein of *Moraxella catarrhalis* strain M35, 3 or LES1, which comprises growing the transformed host provided herein to express Tbp2 protein as inclusion bodies, purifying the inclusion bodies free from cellular material and soluble proteins, solubilizing Tbp2 protein from the purified includsion bodies, and purifying the Tbp2 protein free from other solubilized materials. The substantially pure recombinant transferrin receptor protein is generally at least about 70% pure, preferably at least about 90% pure.

In accordance with another aspect of the invention, an immunogenic composition is provided which comprises at least one active component selected from at least one nucleic acid molecule as provided herein and at least one recombinant protein as provided herein, and a pharmaceutically acceptable carrier therefor or vector therefor. The at least one active component produces an immune response when administered to a host.

The immunogenic compositions provided herein may be formulated as vaccines for in vivo administration to a host. For such purpose, the compositions may be formulated as a microparticle, capsule, ISCOM (immunostimulatory complex) or liposome preparation. The immunogenic composition may be provided in combination with a targeting molecule for delivery to specific cells of the immune system or to mucosal surfaces. The immunogenic compositions of the invention (including vaccines) may further comprise at least one other immunogenic or immunostimulating material and the immunostimulating material may be at least one adjuvant or at least one cytokine.

Suitable adjuvants for use in the present invention include (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein.

Advantageous combinations of adjuvants are described in copending U.S patent applications Ser. Nos. 08/261,194 filed Jun. 16, 1994 and 08/483,856, filed Jun. 7, 1995, assigned to the assignee hereof and the disclosures of which are incorporated herein by reference thereto (WO 95/34308).

In accordance with another aspect of the invention, there is provided a method for generating an immune respons in a host, comprising the step of administering to a susceptible host, such as a human, an effective amount of the immunogenic composition provided herein. The immune response may be a humoral or a cell-mediate immune response and may provide protection against disease caused by *Moraxella*. Hosts in which protection against disease may be conferred include primates, including humans.

In a further aspect of the invention, there is provided a live vector for delivery of Tbp2 protein to a host, comprising a vector containing the nucleic acid molecule as described above. The vector may be selected from *Salmonella*, BCG, adenovirus, poxvirus, vaccinia and poliovirus.

The nucleic acid molecules provided herein are useful in diagnostic applications. Accordingly, in a further aspect of the invention, there is provided a method of determining the presence, in a sample, of nucleic acid encoding a transferrin receptor protein of a strain of *Moraxella*, comprising the steps of:

(a) contacting the sample with a nucleic acid molecule as provided herein to produce duplexes comprising the nucleic acid molecule and any nucleic acid molecule encoding the transferrin receptor protein of a strain of *Moraxella* present in the sample and specifically hybridizable therewith; and (b) determining the production of the duplexes. In addition, the present invention provides a diagnostic kit for determining the presence, in a sample, of nucleic acid encoding a transferrin receptor protein of a strain of *Moraxella*, comprising:

(a) a nucleic acid molecule as provided herein;

(b) means for contacting the nucleic acid molecule with the sample to produce duplexes comprising the nucleic acid molecule and any such nucleic acid present in the sample and hydridizable with the nucleic acid molecule; and (c) means for determining production of the duplexes.

The invention further includes the use of the nucleic acid molecules and proteins provided herein as medicines. The invention additionally includes the use of the nucleic acid molecules and proteins provided herein in the manufacture of medicaments for protection against infection by strains of *Moraxella*.

Advantages of the present invention include:
an isolated and purified nucleic acid molecule encoding a Tbp2 protein of specific strains of *Moraxella catarrhalis*;
recombinantly-produced Tbp2 proteins; and
diagnostic kits and immunological reagents for specific identification of *Moraxella*.

BRIEF DESCRIPTION OF DRAWINGS

The present invention will be further understood from the following description with reference to the drawings, in which:

FIG. 2 shows the nucleotide sequence of the *tbpB* gene (SEQ ID NO: 1) and deduced amino acid sequence of the Tbp2 protein of *M. catarrhalis* strain M35 (SEQ ID NO: 2);

FIG. 4 shows the nucleotide sequence of *tbpB* gene (SEQ ID NO: 3) and the deduced amino acid sequence of the Tbp2 protein of *M. catarrhalis* strain 3 (SEQ ID NO: 4);

FIG. 6 shows the nucleotide sequence of the *tbpB* gene (SEQ ID NO: 5) and deduced amino acid sequence of the Tbp2 *M. catarrhalis* strain LES1 (SEQ ID NO: 6);

FIG. 7 shows an alignment of the Tbp2 proteins from strains 4223 (SEQ ID NO: 7), R1 (SEQ ID NO: 8), M35 (SEQ ID NO: 2), LES1 (SEQ ID NO: 6), Q8 (SEQ ID NO: 9) and 3 (SEQ ID NO: 4). Dots indicate identical residues and spaces have been introduced to maximize the sequence alignment. Underlining indicates those sequences conserved amongst the *M. catarrhalis* Tbp2 proteins and those from *A. pleuropneumoniae, H. influenzae, N. gonorrhoeae, N. meningitidis* and *P. haemolytica* (SEQ ID NO: 7, 8 and 9 are disclsed in WO 97/32380);

FIG. 8 shows the nucleotide and deduced amino acid sequence of the *M. catarrhalis* strain 4223 *tbpA—orf3—tbpB* gene locus (SEQ ID NO: 10—entire gene locus; SEQ ID NO: 11—*tbpA* coding sequence; SEQ ID NO: 12—deduced amino acid sequence of TbpA; SEQ ID NO: 13—*orf3* coding sequence; SEQ ID NO: 14—deduced amino acide sequence of ORF3; SEQ ID NO: 15—*tbpB* coding sequence; SEQ ID NO: 7—deduced amino acid sequence of Tbp2);

FIG. 9 shows an alignment of the ORF3 proteins from *M. catarrhalis* strains 4223 (SEQ ID NO: 14) and Q8 (SEQ ID NO: 16). Dots indicate identical residues. (cf. FIG. 7 of WO 97/32380).

GENERAL DESCRIPTION OF THE INVENTION

Figure 1A:
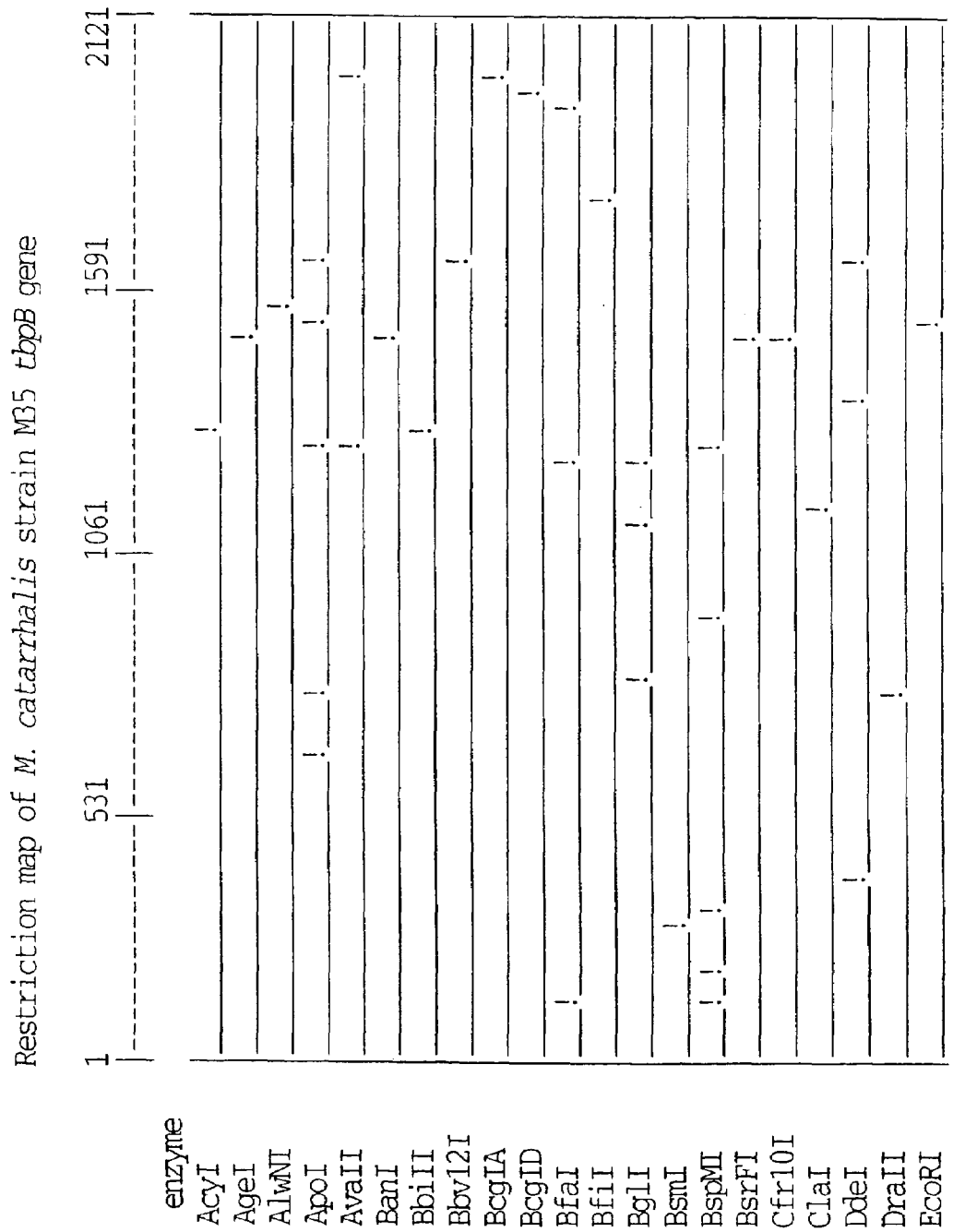
FIG. 1 shows a partial restriction map of the *M. catarrhalis* strain M35 *tbpB* gene.

*Moraxella catarrhalis* strain M35, 3 and LES1 may be conveniently used to provide the purified and isolated nucleic acid, which may be in the form of DNA molecules, comprising at least a portion of the nucleic acid coding for a Tbp2 protein of the strain. Strains 4223, LES1 and M35 are all derived from patients with otitis media while strains 3, R1 and Q8 were from sputum or bronchial secretions.

The *tbpB* genes from *M. catarrhalis* M35, 3 and LES1 were cloned and sequenced herein, following generally the procedures described in WO 97/32380. Strain 3 is a clinical isolate provided by Dr. T. Murphy (State University of New York, Buffalo, N.Y.); strain M35 was obtained from Dr. G. D. Campbell (Louisiana State University, Shreveport, La.) and strain LES1 was obtained from Dr. L. Stanfors (University of Tromoso, Finland).

FIGS. 2, 4 and 6 show the nucleotide sequences of the respective *tbpB* gene (SEQ ID NO: 1, 3 or 5) and deduced amino acid sequence of the Tbp2 protein (SEQ ID NO: 2, 4 or 6) of the *M. catarrhalis* strains M35, 3 and LES1, respectively. Regions of homology are evident between the *M. catarrhalis* Tbp2 amino acid sequences determined herein and those previously determined in WO 97/32380, as shown in the comparative alignment of FIG. 7 (SEQ ID NOS: 7, 8, 2, 6, 9 and 4) and between the *M. catarrhalis* Tbp2 amino acid sequences. Underlining in FIG. 7 indicates those sequences which are conserved among the *M. catarrhalis* Tbp2 proteins and those of *A. pleuropneumoniae, H. influenzae, N. gonorrhoeae, N. meingitidis* and *P. haemolytica*.

Sequence analysis of the nucleotide acid and amino acid sequences of the Tbp2 proteins described herein and in WO 97/32380 indicated that at least two families could be identified for *M. catarrhalis tbpB* genes, one comprising strains 4223, R1 and M35 and other comprising strains Q8 and 3, with strain LES1 being equally related to both families. Anti-rTbp2 bactericidal antibody activity (Table 1) correlated with the putative gene families indentified by sequencing.

Additional sequence analysis of the entire *M. catarrhalis* strains 4223 and Q8 *tbpA—tbpB* locus gene sequence (FIG. 8) identified an intergenic open reading frame termed "orf3" (SEQ ID NO: 13, SEQ ID NO: 14, ORF3 amino acid sequence), (see also FIGS. 10 and 11 for location of orf3). The encoded ORF3 proteins from 4223 and Q8 are 98% identical, as seen from the sequence alignment of FIG. 9 (SEQ ID NOS: 14, 16).

Cloned *tbpB* genes may be expressed in *E. coli* to produce recombinant Tbp2 proteins free of other *Moraxella* proteins. These recombinant proteins may be purified and used for immunization.

The Tbp2 proteins provided herein are useful as a diagnostic reagent, as an antigen for the generation of anti-transferrin protein binding antibodies, as an antigen for vaccination against the disease caused by species of *Moraxella* and for detecting infection by *Moraxella* and other such bacteria.

The Tbp2 proteins provided herein may also be used as a carrier protein for haptens, polysaccharides or peptides to make conjugate vaccines against antigenic determinants unrelated to transferrin binding proteins. In additional embodiments of the present invention, therefore, the Tbp2 proteins as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and PRP. Such bacterial pathogens may include, for example, *Haemophilus influenzae, Streptococcus pneumoniae, Escherichia coli, Neisseria meningitidis, Salmonella typhi, Streptococcus mutans, Cryptococcus neoformans, Klesiella, Staphylococcus aureua* and *Pseudomonas aeruginosa*. Particular antigens which can be conjugated to Tbp2 proteins and methods to achieve such conjugations are described in U.S. patent application Ser. No. 08/433,522 filed Nov. 23, 1993 (WO 94/12641), assigned to the assignee hereof and the disclosure of which is hereby incorporated by reference thereto.

In another embodiment, the carrier function of the Tbp2 proteins may be used, for example, to induce an immune response against abnormal polysaccharides of tumour cells, or to produce anti-tumour antibodies that can be conjugated to chemotherapeutic or bioactive agents.

The invention extends to transferrin binding proteins from *Moraxella catarrhalis* for use as an active ingredient in a vaccine against disease caused by infection with *Moraxella*. The invention also extends to a pharmaceutical vaccinal composition containing transferrin binding proteins from *Moraxella catarrhalis* and optionally, a pharmaceutically acceptable carrier and/or diluent.

In a further aspect the invention provides the use of transferrin binding proteins for the preparation of a pharmaceutical vaccinal composition for immunization against disease caused by infection with *Moraxella*.

It is clearly apparent to one skilled in the art, that the various embodiments of the present invention have many applications in the fields of vaccination, diagnosis, treatment of, for example, *Moraxella* infections and the generation of immunlogical and other diagnostic reagents. A further non-limiting discussion of such uses is further presented below.

1. Vaccine Preparation and Use

Immunogenic compositions, suitable to be used as vaccines, may be prepared from immunogenic transferrin receptor proteins, analogs and fragments thereof encoded by the nucleic acid molecules as well as the nucleic acid molecules disclosed herein. The vaccine elicits and immune response which produces antibodies, including anti-transferrin receptor antibodies and antibodies that are opsonizing or bactericidal. Should the vaccinated subject be challenged by *Moraxella*, the antibodies bind to the transferrin receptor and thereby prevent access of the bacteria to an iron source which is required for viability. Furthermore, opsonizing or bactericidal anti-transferrin receptor antibodies may also provide protection by alternative mechanisms.

Immunogenic compositions, including vaccines, may be prepared as injectables, as liquid solutions or emulsions. The transferrin receptor proteins, analogs and fragments thereof and encoding nucleic acid molecules may be mixed with pharmaceutically acceptable excipients which are compatible with the transferring receptor proteins, fragments, analogs or nucleic acid molecules. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants, to enhance the effectiveness of the vaccines. Immunogenic compositions and vaccines may be administered parenterally, by injection subcutaneously, intradermally or intramuscularly. Alternatively, the immunogenic compositions provided according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration, including suppositories and oral formulations, may be desirable. For suppositories, binders and carriers may include, for example, polyalkalene glycols or triglycerides.

Oral formulations may include normally employed incipients such as, for example, pharmaceutical grades of saccharine, cellulose and magnesium carbonate. These compositions may take the form of solutions, suspensions, tablets, pills, capsules, sustained release formulations or powders and contain about 1 to 95% of the transferrin receptor proteins, fragments, analogs and/or nucleic acid molecules.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and, if needed, to produce a cell-mediated immune response. Precise amounts of active ingredient required to be administered depend on the judgment of the practitioner. However, suitable dosage ranges are readily determinable by one skilled in the art and may be of the order of micrograms of the transferrin receptor proteins, analogs and fragments thereof and/or nucleic acid molecules. Suitable regimes for initial administration and booster doses are also variable, but may include an initial administration followed by subsequent administrations. The dosage of the vaccine may also depend on the route of administration and will vary according to the size of the host.

The nucleic acid molecules encoding the transferrin receptor of *Moraxella* may be used directly for immunization by administration of the DNA directly, for example, by injection for genetic immunization or by constructing a live vector, such as *Salmonella*, BCG, adenovirus, poxvirus, vaccinia or poliovirus containing the nucleic acid molecules. A discussion of some live vectors that have been used to carry heterologous antigens to the immune system is contained in, for example, O'Hagan (ref. 22). Processes for the direct injection of DNA into test subjects for genetic immunization are described in, for example, Ulmer et al. (ref. 23).

Immunogenicity can be significantly improved if the antigens are co-administered with adjuvants, commonly used as an 0.05 to 1.0 percent solution in phosphate— buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and an HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:

(1) lack of toxicity;

(2) ability to stimulate a long-lasting immune response;

(3) simpliciaty of manufacture and stability in long-term storage;

(4) ability to elicit both CMI and HIR to antigens administered by various routes,m if required;

(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example, IgA) against antigens.

U.S. Pat. No. 4,855,283 granted to Lockoff et al on Aug. 8, 1989, which is incorporated herein by reference thereto, teaches glycolipid analogues including N-glycosylamides, N-glycosylureas, and N-glycosylcarbamates, each of which is substituted in the sugar residue by an amino acid, as immuno-modulators or adjuvants. Thus, Lockoff et al. 1991 (ref. 24) reported that N-glycolipid analogs displaying structural similarities to the naturally-occurring glycolipids, such as glycophospholipids and glycoglycerolipids, are capable of eliciting strong immune responses in both herpes simplex virus vaccine and pseudorables virus vaccine. Some glycolipids have been synthesized from long chain-alkylamides and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990, (ref. 25) reported that octadecyl esters of aromatic amino acids complexed with a recombinant hepatitis B surface antigen, enhanced the host immune responses against hepatitis B virus.

2. Immunoassays

The transferrin receptor proteins, analogs and/or fragments thereof of the present invention are useful as immunogens, as antigens in immunoassays including enzymlinked immunosorbent assays (ELISA), RIAs and other non-enzyme linked antibody binding assays or procedures known in the art for the detection of anti-*Moraxella* transferrin receptor protein antibodies. In ELISA assays, the transferrin receptor protein, analogs and/or fragments corresponding to portions of TfR protein, are immobilized onto a selected surface, for example, a surface capable of binding proteins or peptides such as the wells of a ploystyrene microtiter plate. After washing to remove incompletely adsorbed transferrin receptor, analogs and/or fragments, a non-specific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by non-specific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution such as PBS/Tween or a borate buffer.

Following formation of specific immunocomplexes between the test sample and the bound transferrin receptor protein, analogs and/or fragments and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then achieved by measuring the degree of color generation using, for example, a spectrophotometer.

3. Use of Sequences as Hybridization Probes

The nucleotide sequences of the present invention, comprising the sequence of the transferrin receptor gene, now allow for the indentification and cloning for the transferrin receptor gene from any species for *Moraxella*.

The nucleotide sequences comprising the sequence of the transferrin receptor genes of the present invention are useful for their ability to selectively form duplex molecules with complementary stretches of other TfR genes. Depending on the application, a variety of hybridization conditions may be employed to achieve varying degrees of selectivity of the probe toward the other TfR genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% foramide are: 42° C. for a probe which is 95 to 100% homologous to the target fragment, 37° C. for 90 to 95% homology and 32° C. for 85 to 90% homology.

In a clinical diagnositc embodiment, the nucleic acid sequences of the TfR genes of the present invention may be used in combination with an appropriate means, such as a label, for determining hybridization. A wide variety of appropriate indicator means are known in the art, including radioactive, enzymatic or other ligands, such as avidin/biotin and digoxigenin-labeling, which are capable of providing a detectable signal. In some diagnostic embodiments, an enzyme tag such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridizaiton with samples containing TfR gene sequences.

The nucleic acid sequences of TfR genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the TfR genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of *Moraxella*. The selected probe may be at least 18 bp and may be in the range of about 30 to 90 bp.

4. Expression of the Transferrin Receptor Genes

Plasmid vectors containing replicon and control sequences which are derived from species compatible with the host cell may be used for the expression of the transferrin receptor genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems and other microbial promoters, such as the T7 promoter system as descried in U.S. Pat. No. 4,952,496. Details concerning the nucleotide sequences of promoters are known, enabling a skilled worker to ligate them functionally with genes. The particular promoter used will generally be a matter of choice depending upon the desired results. Hosts that are appropriate for expression of the transferrin receptor genes, fragments, analogs or variants thereof, may include *E. coli, Bacillus* species, *Haemophilus*, fungi, yeast, *Moraxella, Bordetella*, or the baculovirus expression system may be used.

In accordance with this invention, it is preferred to make the transferrin receptor protein, fragment or analog thereof, by recombinant methods, particularly since the naturally occurring TfR protein as purified from a culture of a species of *Moraxella* may include trace amounts of toxic materials or other contaminants. This problem can be avoided by using recombinantly produced TfR protein in heterologous systems which can be isolated from the host in a manner to minimize contaminants in the purified material. Particularly desirable hosts for expression in this regard include Gram positive bacteria wihch do not have LPS and are, therefore, endotoxin free. Such hosts include species of *Bacillus* and may be particularly useful for the production of non-pyrogenic transferrin receptor, fragments or analogs thereof.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry and immunology used but not explicitly described in this disclosure and these Examples are amply reported in the scientific literature and are well within the ability of those skilled in the art.

EXAMPLE 1

This Example illustrates the preparation of chromosomal DNA from *M. catarrhalis* strain M35, following the procedure described in WO 97/32380 for strains 4223 and Q8 (Example 2).

*M. catarrhalis* isolate M35 was inoculated into 100 ml of BHI broth, and incubated for 18 hr at 37° C. with shaking. The cells were harvested by centrifugation at 10,000 × g for 20 min. The pellet was used for extraction of *M. catarrhalis* M35 chromosomal DNA.

The cell pellet was resuspended in 20 ml of 10 mM Tris-HCl (pH 7.5)–1.0 mM EDTA (TE). Pronase and SDS were added to final concentrations of 500 µg/ml and 1.0%, respectively, and the suspension was incubated at 37° C. for 2 hr. After several sequential extractions with phenol, phenol:chloroform (1:1), and chloroform:isoamyl alcohol (24:1), the aqueous extract was dialysed, at 4° C., against 1.0 M NaCl for 4 hr, and against TE (pH 7.5) for a further 48 hr with three buffer changes. Two volumes of ethanol were added to the dialysate, and the DNA was spooled onto a glass rod. The DNA was allowed to air-dry, and was dissolved in 3.0 ml of water. Concentration was estimated, by UV spectrophotometry, to be about 290 µg/ml. This procedure was repeated for the preparation of chromosomal DNA from *M. catarrhalis* strain 3 and LES1.

EXAMPLE 2

This Example illustrates the construction of a *M. catarrhalis* strain M35 chromosomal library in EMBL3.

A series of Sau3A restriction digests of chromosomal DNA from *M. catarrhalis* M35, prepared as described in Example 1, in final volumes of 10 µL each, were carried out in order to optimize the conditions necessary to generate maximal amounts of restriction fragments within a 15 to 23 kb size range. Using the optimized digestion conditions, a large-scale digestion was set up in a 100 µL volume, containing the following: 50 µL of chromosomal DNA (290 µg/mol), 33 µL water, 10 µL 10× Sau3A buffer (New England Biolabs), 1.0 µL BSA (10 mg/ml, New England Biolabs), and 6.3 µL Sau3A (0.04 U/µL), Following a 15 min. incubation at 37° C., the digestion was terminated by the addition of 10 µL of 100 mM Tri-HCl (pH 8.0)–10 mM EDTA-0.1% bromophenol blue-50% glycerol (loading buffer). Digested DNA was electrophoresed through a 0.5% agarose gel in 40 mM Tris acetate-2 mM $Na_2EDTA.2H_2O$ (pH8.5) (TAE buffer) at 50 V for 6 hr. The region containing restriction fragments within a 15 to 23 kb molecular size range was excised from the gel, and placed into dialysis tubing containing 3.0 ml of TAE buffer. DNA was electroeluted from the gel fragment by applying a field strength of 1.0 V/cm for 18 hr. Electroeluted DNA was extracted once each with phenol and phenol:chloroform (1:1), and precipitated with ethanol. The dired DNA was dissolved in 5.0 µL water.

Size-fractionated chromosomal DNA was ligated with BamHI-digested EMBL3 arms (Promega), using T4 DNA ligase in a final volume of 9 µL. The entire ligation mixture was packaged into lambda phage using a commercial packaging kit (Amersham), following manufacturer's instructions.

The packaged DNA library was amplified on solid media. 0.1 ml aliquots of *Escherichia coli* strain NM539 in 10 mM $MgSO$, ($OD_{260}$=0.5) were incubated at 37° C. for 15 min. with 15 to 25 µL of the packaged DNA library. Samples were mixed with 3 ml of 0.6% agarose containing 1.0% BBL trypticase peptone-0.5% NaCl (BBL top agarose), and mixtures were plated onto 1.5% agar plates containing 1.0% BBL trypticase peptone-0.5% NaCl, and incubated at 37° C. for 18 hr. 3 ml quantities of 50 mM Tris-HCl (pH 7.5)–8 mM magnesium sulfate heptahydrate-100 mM NaCl-0.01% (w/v) gelatin (SM buffer) were added to each plate, and plates were left at 4° C. for 7 hr. SM buffer containing phage was collected from the plates, pooled together, and stored in a screwcap tube at 4° C., with chloroform.

EXAMPLE 3

This Example illustrates screening of the *M. catarrhalis* strain M35 library.

The EMBL3/M35 library, prepared as described in Example 2, was plated onto LE392 cells on YT plates using 0.7% top agar in YT as overlay. Plaques were lifted onto nitrocellulose filters and the filters were probed with oligonucleotide probes labelled with $^{32}P\alpha$-dCTP (Random Primed DNA labeling kit, Boehringer Mannheim). The pre-hybridization was performed in sodium chloride/sodium citrate (SSC) buffer (ref. 27) at 37° C. for 1 hour and the hybridization was performed at 42° C. overnight. The probes were based upon an internal sequence of 4223 tbpA:

I R D L T R Y D P G (SEQ ID NO: 17)

4236-RD 5' ATTCGAGACTTAACACGCTATGAC-CCTGGC 3'

(Seq ID No 18)

4237-RD 5' ATTCGTGATTTAACTCGCTATGAC-CCTGGT 3'

(Seq ID No 19).

Putative plaques were re-plated and submitted to second and third rounds of screening using the same procedures.

Phage clone M35-2.3 was found to contain a 13 kb insert of the M35 tfr genes. The tbp5 gene was localized to a 7.5 kb Nhel—Sal I fragment by restriction enzyme and Southern blot analyses and was subcloned into pBR328 for sequence analysis, generating plasmid pLEM40.

Figure 1B:
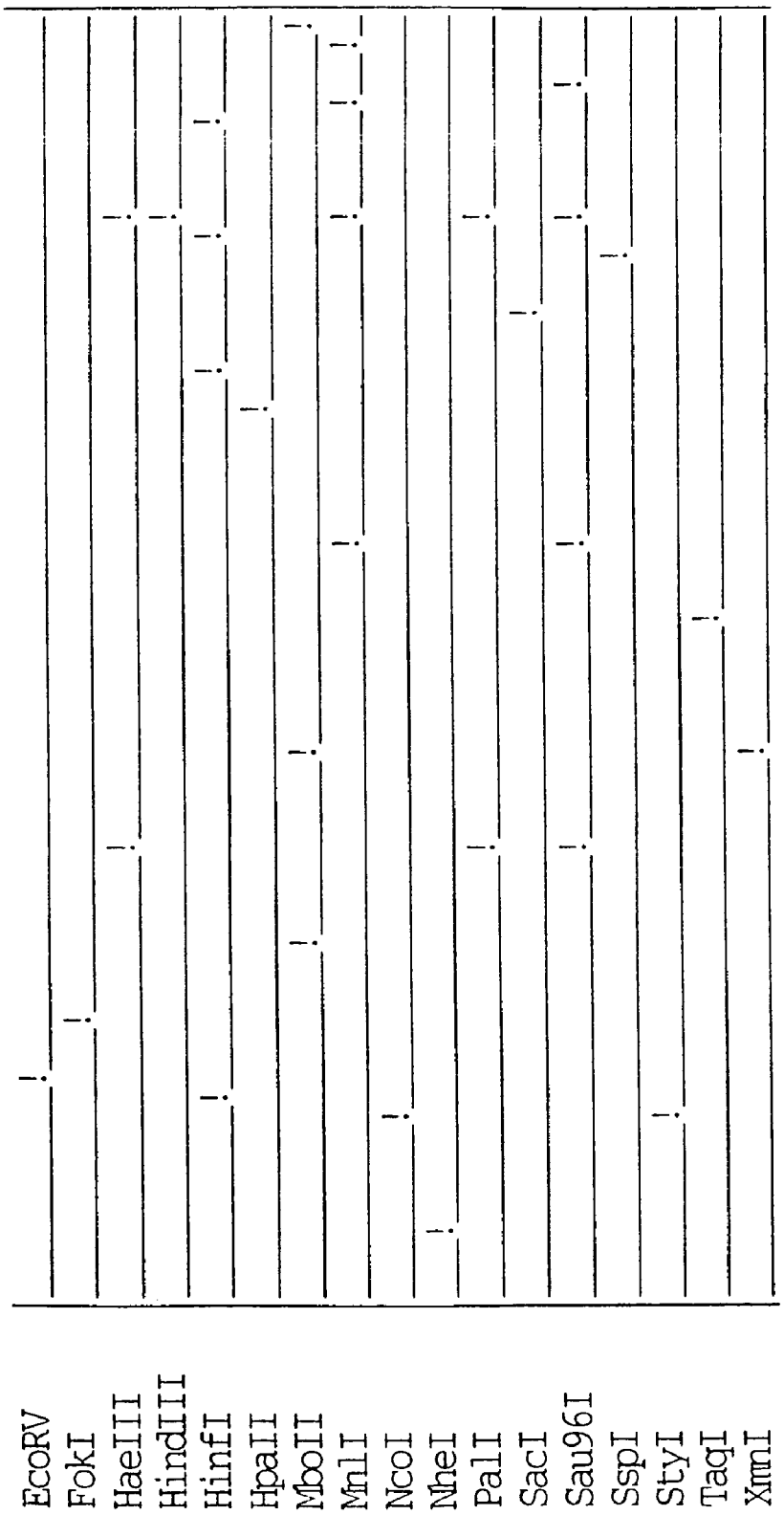

A partial restriction map of the M35 tbpB gene is shown in FIG. 1. The nucleotide and deduced amino acid sequences of the M35 tbpB gene are shown in FIG. 2. The M35 tbpB gene encodes a 706 amino acid protein of molecular weight 76.5 kDa. When the M35 TbpB sequence was aligned with the 4223 TbpB protein (FIG. 7), it was found to be 86% identical and 90% similar.

EXAMPLE 4

This Example illustrates the PCR amplification of the tbpB genes from *M. catarrhalis* strains 3 and LES1, following the procedure described in WO 97/32380 for *M. catarrhalis* strain R1.

Oligonucleotide primers were based upon the following sequences, which are found in the intergenic regions surrounding *M. catarrhalis* strain 4223 tbpB:

5' GATGGGATAAGCACGCCCTACTT 3' (SEQ ID NO: 20)

sense primer (4940)

5' CCCATCAGCCAAACAAACATTGTGT 3' (SEQ ID NO: 21)

antisense primer (4967)

PCR amplification was performed in buffer containing 100 mM Tris-HCI (pH 8.9), 25 mM KCI, 5 mM $(NH_4)_2SO_4$ and 2 mM $MgSO_4$. Each 100 µl reaction mixture contained 10 ng of chromosomal DNA from strains 3 and LES1, prepared following the procedure of Example 1, 1 µg each primer, 2.5 U Pwo DNA polymerase (Boehringer Mannheim) and 0.2 mM dNTPs (Perkin Elmer, Foster City, Calif.). The cycling conditions were 25 cycles of 95° C. for 30 sec, 45° C. for 1.0 min and 72° C. for 2.0 min, followed by a 10 min elongation at 72° C. Specific 2.4 kb fragments were amplified and DNA was purified for direct sequencing by agarose gel extraction, using a Geneclean kit (Bio 101 Inc., Vist, Calif.). Plasmid DNA for sequencing was prepared using a Qiagen Plasmid Midi kit (Qiagen, Chatsworth, Calif.). DNA samples were sequenced using an ABI model 373A DNA sequencer using dye terminator chemistry. Oligonucleotide primers of 17 to 25 bases in length were used to sequence both strands of the genes.

Figure 3A:
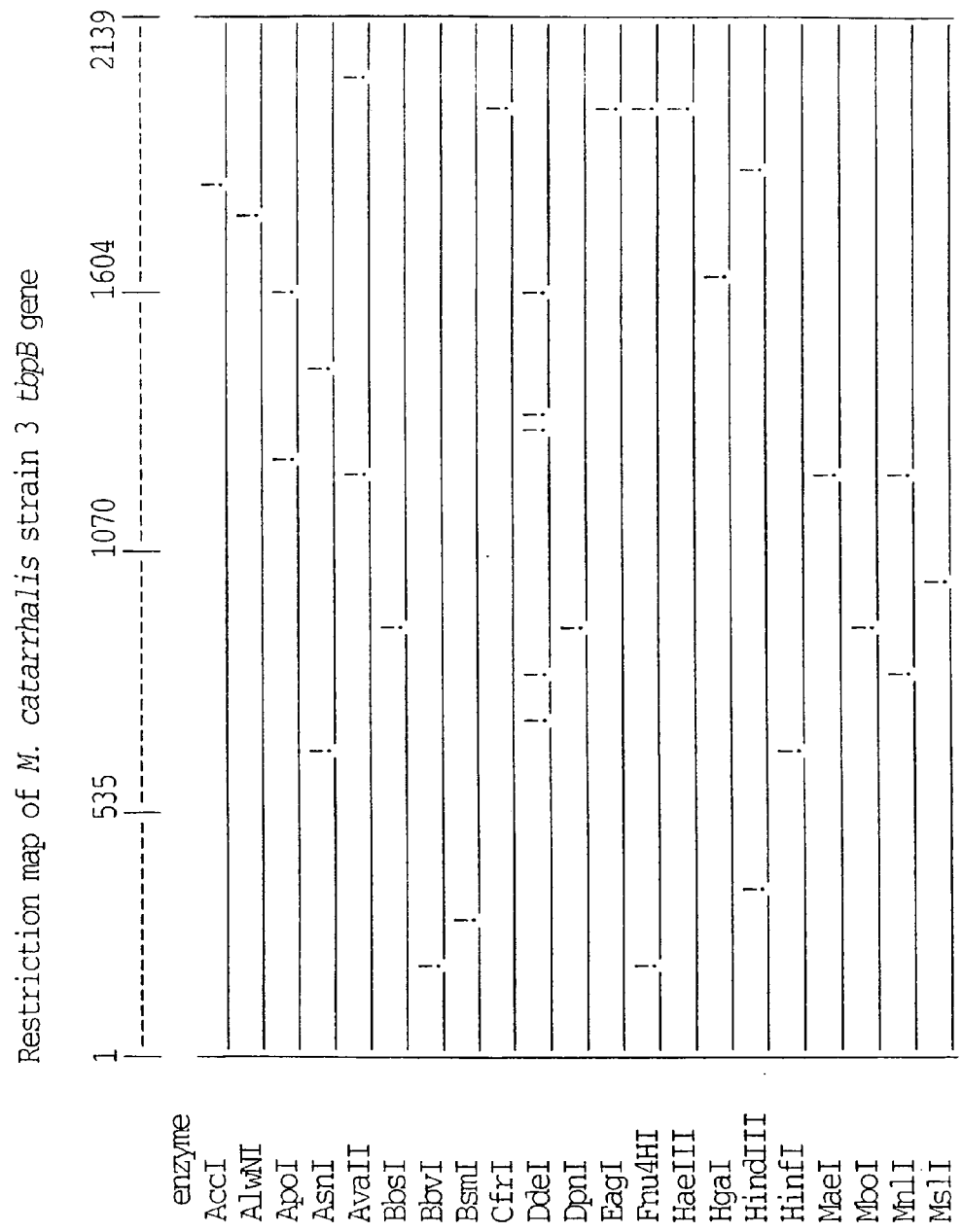
FIG. 3 shows a partial restriction map of the *tbpB* gene for *M. catarrhalis* strain 3.
Figure 3B:
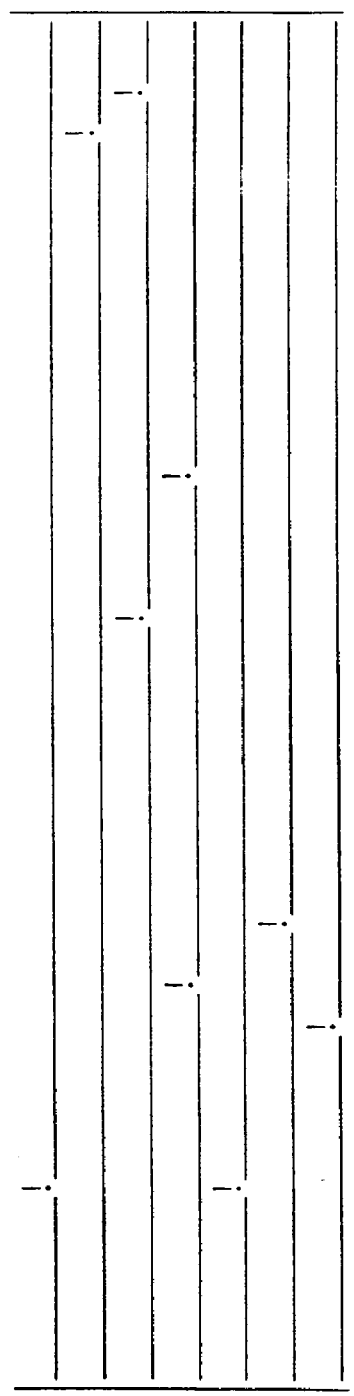
Figure 5B:
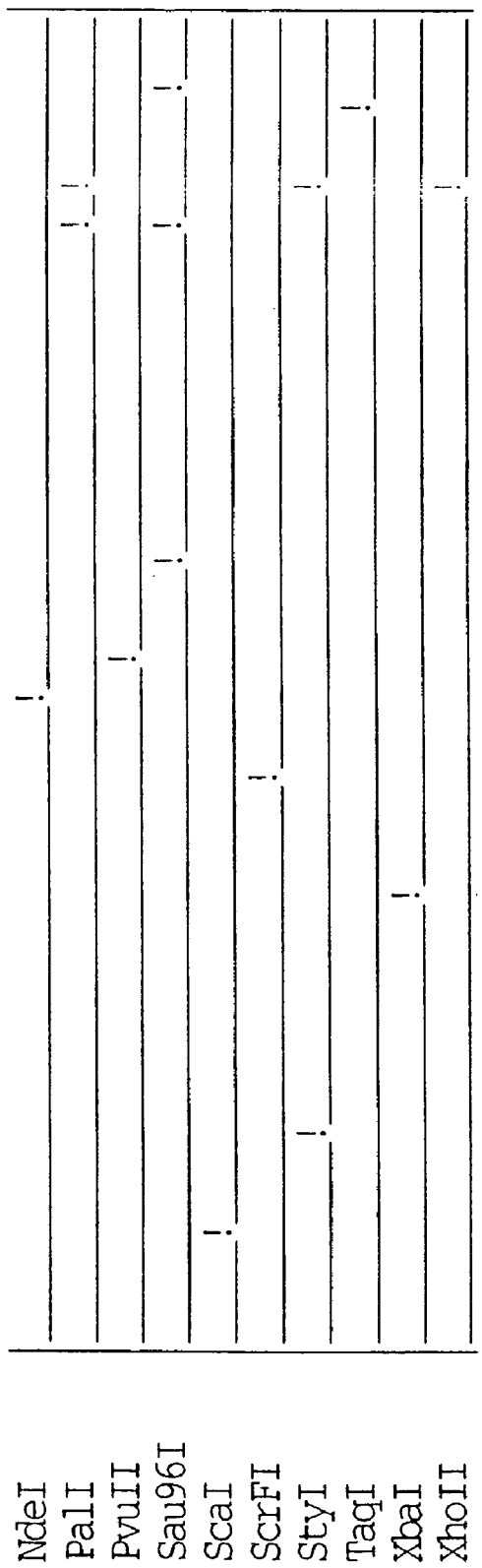
FIG. 5 shows a partial restriction map of the *tbpB* gene for *M. catarrhalis* strain LES1.
Figure 7A:
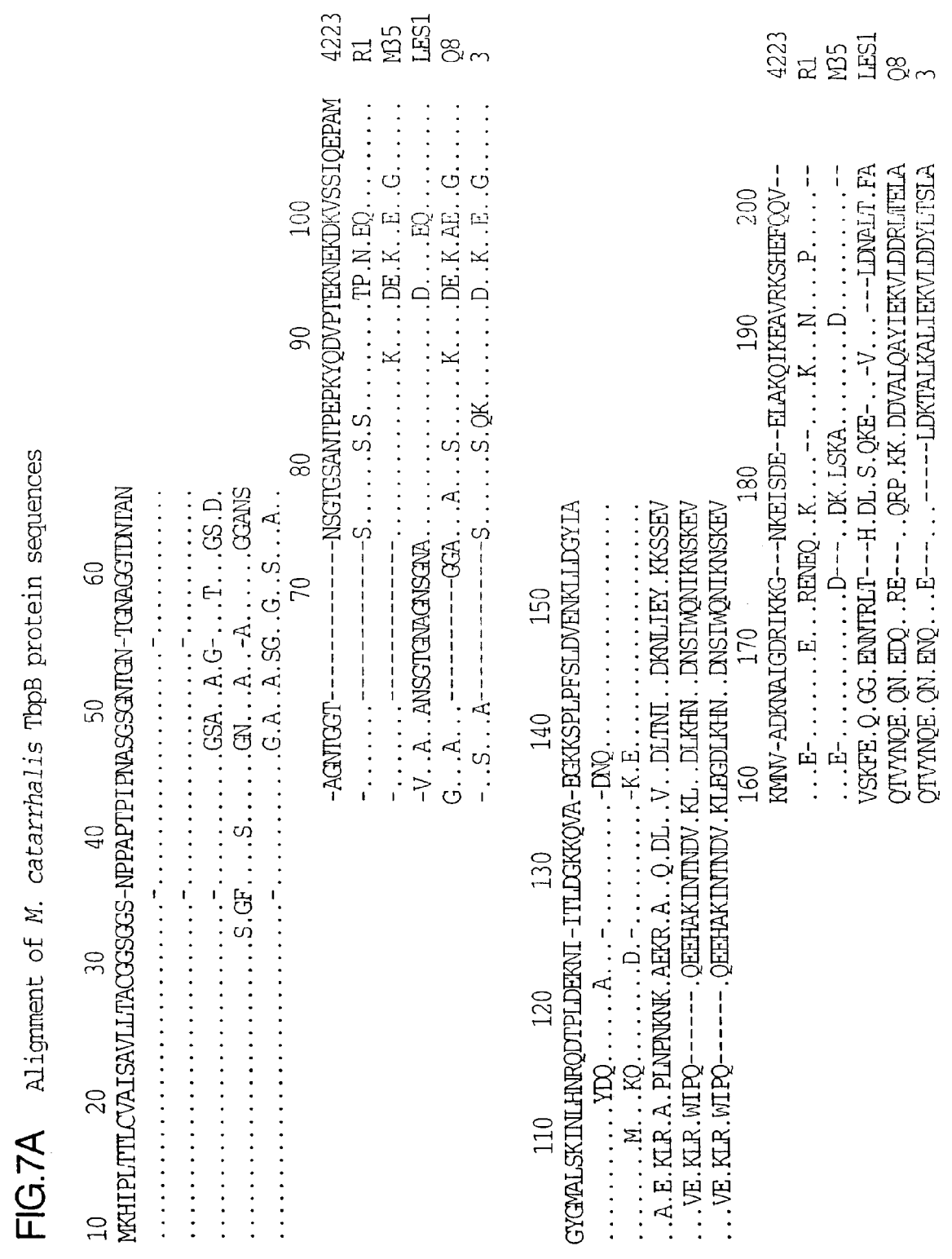

Partial restriction maps of the *M. catarrhalis* strains 3 and LES1 *tpbB* genes are shown in FIGS. 3 and 5 respectively. The nucleotide and deduced amino acid sequences of the strain 3 and LES1 *tpbB* genes are shown in FIGS. 4 and 6, respectively. The strain 3 tbpB gene encodes a 712 amino acid protein of molecular weight 76.9 kDa, which is more closely related to the strain Q8 Tbp2 protein than to the 4223 Tbp2 protein (FIG. 7). The Q8 and strain 3 Tbp2 proteins are 71% identical and 79% similar, whereas the 4223 and strain 3 Tbp2 proteins are 51% identical and 64% similar. The strain LES1 tbpB gene encodes a 713 amino acid protein of molecular weight 76.8 kDa which is 63% identical to both the 4223 and Q8 Tbp2 protein.

From the sequence analysis presented herein and in further consideration of the sequences presented in WO 98/32380, there appear to be at least two gene families which can be identified for M. catarrhalis tbpB, one comprising strains 4223, R1 and M35 and the other comprising strains Q8 and 3, with strain LES1 being equally related to both families. This novel finding is similar to that of the N. meningitidis tbpB genes which can be divided into two sub-groups (ref. 28). There is limited sequence homology among the amino acid sequences of the M. catarrhalis Tbp2 proteins previously identified in WO 98/32380 and in this application and those from other organisms, such as Actinobacillus pleuropneumoniae, H. influenzae. N. gonorrhoeae, N. miningitidis and P. haemolytical (ref. 29). The homology is scattered in small peptide motifs throughout the sequence and is illustrated by underlining in FIG. 7. The conserved LEGGFYG (SEQ ID NO: 22) epitope was present, as found in Tbp2 for other M. catarrhalis strains as well as the H. influenzae and N. meningitidis Tbp2 proteins.

EXAMPLE 5

This Example illustrates the bactericidal antibody activity of guinea pig anti-4223 rTbp2 and anti-Q8 rTbp2 antibodies, prepared as described in WO 97/32380 (Example 14), and confirmation of the gene families of tbpB genes.

The bactericidal antibody assay was performed as described by Yang et al. (ref. 30). Briefly, several M. catarrhalis strains were grown to an $OD_{578}$ of 0.5 in BHI medium containing 25 mM EDDA. The bacteria were diluted so that the pre-bleed control plates contained 100 to 300 cfu. Guinea pig anti-rTbp2 antisera and pre-bleed controls, prepared as described in Example 14 of WO 97/32380, were heated to 56° C. for 30 min to inactivate endogenous complement and were diluted 1:64 with veronal buffer containing 0.1% BSA (VBS). Guinea pig complement was diluted 1:10 in VBS. Twenty-five µl each of diluted antiserum, bacteria and complement were added to duplicate wells of a 96 well microtiter plate. The plates were incubated at 37° C. for 60 min, gently shaking at 70 rpm on a rotary platform. Fifty µl of each reaction mixture were plated onto Mueller Hinton agar plates which were incubated at 37° C. for 24 h, then room temperature for 24 h, before the bacteria were counted. Antisera were determined to be bactericidal if ≧50% of bacteria were killed compared with negative controls. Each assay was repeated at least twice in duplicate. The assay was performed using both the anti-Tbp2 antisera from both 4223 and Q8 strains against a number of different strains of Moraxella catarrhalis. The strains tested are identified and the results obtained are shown in Table 1.

The anti-rTbp2 bactericidal antibody activity shown in Table 1 corelates with the putative gene families identified by sequencing, as described in Example 4. Anti-4223 rTbp2 antibody kills those strains within its own family, i.e. 4223, R1 and M35, while anti-Q8 rTbp2 antibody kills those strains within its family, i.e. Q8, 3 and LES1. The anti-4223 rTbp2 antibody also killed strains VH-9, H-04 and ATCC 25240 indicating that the latter strains may be part of the 4223 family. Strain H-04 was also killed by anti-Q8 rTbp2 antibody.

EXAMPLE 6

This Example illustrates the sequence analysis of the open reading frame (ORF) within the intergenic region between M. catarrhalis tbpA and tbpB.

The integenic region was sequenced for strains 4223 and Q8 and a single open reading frame was identified. This orf, identified as orf3, was located about 1 kb downstream of tbpA and about 273 bp upstream of tbpB in each genome. The nucleotide and deduced amino acid sequences of the entire 4223 tpbA—orf3—tbpB gene loci are shown in FIG. 8. The encoded 4223 and Q8 ORF3 proteins are 98% identical, 512 amino acid proteins, of molecular weight 58.1 kDa and 57.9 kDa, respectively. The alignment of the ORF3 protein sequences is shown in FIG. 9.

SUMMARY OF THE DISCLOSURE

In summary of this disclosure, the present invention provides purified and isolated DNA molecules containing transferrin receptor genes of specific strains of Moraxella catarrhalis, the sequences of these transferrin receptor genes, and the derived amino acid sequences of the Tbp2 proteins encoded thereby. The genes and DNA sequences are useful for diagnosis, immunization, and the generation of diagnostic and immunological reagents. Immunogenic compositions, including vaccines, based upon expressed recombinant Tbp1 and/or Tbp2, portions thereof, or analogs thereof, can be prepared for prevetnion of diseases caused by Moraxella. Modifications are possible within the scope of this invention.

TABLE I

Bactericidal antibody activity of guinea pig anti-rTbpB antisera

| | Bactericidal Antibody Activity* | |
| --- | --- | --- |
| M. catarrhalis strain | Anti-4223 rTbp2 | Anti-Q8 rTbp2 |
| 4223 | ++ | – |
| M35 | ++ | – |
| R1 | ++ | – |
| LES1 | – | + |
| Q8 | – | ++ |
| 3 | – | ± |
| VH-9 | ++ | – |
| H-04 | ++ | ++ |
| ATCC 25240 | ** | – |

*killing by antiserum diluted 1:64 compared to negative controls: – indicates 0 to 25% killing; ± indicates 26 to 49%; + indicates 50 to 75%; ++ indicates 76 to 100% killing.

REFERENCES

1. Brorson, J-E., A. Axelsson, and S. E. Holm. 1976. Studies on Branhamella catarrhalis (Neisseria catarrhalis) with special reference to maxillary sinusitis Scan. J. Infect. Dis. 8:151-155.

2. Catlin, B. W., 1990. Branhamella catarrhalis: an organism gaining respect as a pathogen. Clin. Microbiol. Rev. 3: 293-320.

3. Hager, H., A. Verghese, S. Alvarez, and S. L. Berk. 1987. Branhamella catarrhalis respiratory infections. Rev. Infect. Dis. 9:1140-1149.

4. McLeod, D. T., F. Ahmad, M. J. Croughan, and M. A. Calder. 1986. Bronchopulmonary infection due to *M. catarrhalis*. Clincial features and therapeutic responses. Drugs 31(Suppl.3):109-112.

5. Nicotra, B., M. Rivera, J. I. Luman, and R. J. Wallace. 1986. *Branhamella catarrhalis* as a lower respiratory tract pathogen in patients with chronic lung diseases. Arch.Intern.Med. 146:890-893.

6. Ninane, G., J. Joly, and M. Krayman. 1978. Bronchopulmonary infection due to *Branhamella catarrhalis* 11 cases assessed by transtracheal puncture. Br.Med.Jr. 1:276-278.

7. Strinivasan, G., M. J. Raff, W. C. Templeton, S. J. Givens, R. C. Graves, and J. C. Mel. 1981. *Branhamella catarrhalis* pneumonia. Report of two cases and review of the literature. Am.Rev. Respir. Dis. 123:553-555.

8. West, M., S. L. Berk, and J. K. Smith, 1982. *Branhamella catarrhalis* pneumonia. South.Med. J. 75:1021-1023.

9. Christensen, J. J., and B. Bruun. 1985. Bacteremia caused by a beta-lactamase producing strain of *Branhamella catarrhalis*. Acta.Pathol. Microbiol. Immunol. Scand. Sect.B 93:273-275.

10. Craig, D. B., and P. A. Wehrle. 1983. *Branhamella catarrhalis* septic arthritis. J. Rheumatol. 10:985-986.

11. Guthrie R., K. Bakenhaster, R. Nelson, and R. Woskobnick. 1988. *Branhamella catarrhalis sepsis*: a case report and review of the literature J.Infect.Dis. 158:907-908.

12. Hiroshi, S., E. J. Anaissie, N. Khardori, and G. P. Bodey. 1988. *Branhamella catarrhalis* septicemia in patients with leukemia. Cancer 61:2315-2317.

13. O'Neill, J. H., and P. W. Mathieson. 1987. Meningitis due to *Branhamella catarrhalis*. Aust. N. Z. J. Med. 17:241-242.

14. Murphy, T. F. 1989. The surface of *Branhamella catarrhalis*: a systematic approach to the surface antigens of an emerging pathogen. Pediatr. Infect. Dis. J. 8:S75-S77.

15. Van Hare, G. F., P. A. Shurin, C. D. Marchant, N. A. Cartelli, C. E. Johnson, D. Fulton, S. Carlin, and C. H. Kim. Acute otitis media caused by *Branhamella catarrhalis*: biology and therapy. Rev. Infect. Dis. 9:16-27.

16. Jorgensen, J. H., Doern, G. V., Maher, L. A., Howell, A. W., and Redding, J. S., 1990 Antimicrobial resistance among respiratory isolates of *Haemophilus influenza, Moraxella catarrhalis*, and *Streptococcus* pneumoniae in the United States. Antibicrob. Agents Chemother. 34:2075-2080.

17. Schryvers, A. B. and Morris, L. J. 1988 Identification and Characterization of the transferrin receptor from *Neisseria meningitidis*. Mol. Microbiol. 2:281-288.

18. Lee, B. C., Schryvers, A. B. Specificity of the lactoferrin and transferrin receptors in *Neisseria gonorrhoeae*. Mol. Microbiol. 1988; 2-827-9.

19. Schryvers, A. B. Characterization of the human transferrin and lactoferrin receptors in *Haemophilus influenzae*. Mol. Microbiol. 1988; 2: 467-72.

20. Schryvers, A. B. and Lee, B. C. (1988) Comparative analysis of the transferrin and lactoferrin binding proteins in the family *Neisseriaceas*. Can. J. Microbiol. 35, 409-415.

21. Yu, R. and Schryvers, A. B., 1993. The interaction between human transferrin and transferrin binding protein 2 from *Moraxella* (*Branhamella*) *catarrhalis* differs from that of other human patahogens. Microbiol. Pathogenesis, 15:433-445.

22. O'Hagan, 1992. Clin. Pharmokinet. 22:1.

23. Ulmer et al., 1993. Curr. Opinion Invest. Drugs 2: 983-989.

24. Lockhoff, O., 1991. glycolipids as immunomoclutators: Synthesis and properitis. Chem. Int. Ed. Engl. 30:1611-1620.

25. Nixon-George, 1990. J. Immunol. 14:4798-4802.

26. Wallace, R. J. Jr., Nash, D. R., and Steingrube, V. A. 1990. Antibiotic susceptibilites and drug resistance in *Moraxella* (*Branhaemella*) *catarrhalis*. Am. J. Med. 88 (5A):465-50S.

27. F. M. Ausubel et al., Short protocols in Molecular Biology, Greene Publishing Associates and John Wiley and Sons.

28. Legrain, M., V. Mazarin, S. W. Irwin, B. Bouchon M- J. Quentin-Millet, E. Jacobs, and A. B. Schryvers. 1993, Cloning and characterization of *Neisseria meningitidis* genes encoding the transferrin-binding proteins Tbp1 and Tbp2. Gene 130:73-80.

29. Ogunnariwo, J. W., Woo, T. K. W., Lo, R. Y. C., Gonzalez, G. C., and Schryvers, A. B. Characterization of the Pasteurella haemolytica transferring receptor genes and the recombinant receptor proteins. Microb. Pathog. 23:273-284 (1997).

30. Yang, Y. P., Myers, L. E., McGuinness, U., Chong, P., Kwok, Y., Llein, M. H. and Harkness R. E. The major outer membrane proteihn, C. D.,m extracted from *Moraxella* (*Branhamella*) *catarrhalis* is a potential vaccine antigen that induces bactericidal antibodies. FEMS Immun. Med. Microbiol. 17:187-199 (1997).

We claim:

1. A recombinant Tbp2 protein of *Moraxella catarrhalis* strain M35, 3 or LES1, having a deduced amino acid sequence selected from the group consisting of those shown in FIGS. 2, 4 or 6 (SEQ ID NO: 2, 4 or 6).

2. An immunogenic composition, comprising at least one active component selected from the group consisting of the recombinant Tbp2 proteins claimed in claim 1; and a pharmaceutically carrier therefor, said at least one active component producing an immune response when administered to a host.

3. A method for generating an immune response in a host, comprising administering to the host an immunoeffective amount of an immunogenic composition selected from the group consisting of the immunogenic compositions claimed in claim 2.

4. A recombinant transferrin receptor protein of claim 1 for use as a medicine.

* * * * *

SEQUENCE LISTING

```
<160> NUMBER OF SEQ ID NOS: 22

<210> SEQ ID NO 1
<211> LENGTH: 2121
<212> TYPE: DNA
<213> ORGANISM: Moraxella catarrhalis

<400> SEQUENCE: 1
```

-continued

```
atgaaacaca ttcctttaac cacactgtgt gtggcaatct ctgccgtctt attaaccgct     60
tgtggtggca gtggtggttc aaatccacct gctcctacgc ccattccaaa tgctagcggt    120
tcaggtaata ctggcaacac tggtaatgct ggcggtactg ataatacagc caatgcaggt    180
aatacaggcg gtacaaactc tggtacaggc agtgccaaca caccagaacc aaaatataaa    240
gatgtgccaa ccgatgaaaa taaaaaagat gaagtgtcag gcattcaaga acctgccatg    300
ggttatggca tggctttgag taaaatgaat ctacacaaac aacaagacac gccattagat    360
gaaaaagata tcattacctt agacggtaaa aacaagttg caaaaggtga aaatcgcca     420
ttgccatttt cgttggatgt agaaaataaa ttgcttgatg gctatatagc aaaaatgaat    480
gaagcggata aaaatgccat tggtgacaga attaagaaag ataataaaga caagtcatta    540
tctaaagcag agcttgccaa acaaatcaaa gaagatgtgc gtaaaagcca tgagtttcag    600
caagtattat catcactgaa aaacaaaatt tttcattcaa atgatggaac aaccaaagca    660
accacacgag atttacaata tgttgattat ggttactact tggtgaatga tggcaattat    720
ctaaccgtca aaacagacga actttggaat ttaggccctg tgggcggtgt gttttataat    780
ggcacaacga ccgccaaaga gctacccaca caagatgcgg tcaaatataa aggacattgg    840
gactttatga ccgatgttgc caaacaaaga accgattta gcgaagtgaa agaaaaccttt    900
caagcaggtc ggtattatgg agcatcttca aaagatgaat acaaccgctt attaactgat    960
gagaaaaaca aaccgagcg ttataacggt gaatatggtc atagcagtga gtttactgtt   1020
aattttaagg acaaaaaatt aacaggtgag ctgtttagta acctacaaga cagccgtaag   1080
ggcaatgtta cgaaaaccaa acgctatgac atcgatgcca atatctacgg caaccgcttc   1140
cgtggcagtg ccaccgcaag cgataaagca gaagcaagca aaaccaaaca ccccttttacc   1200
agcgatgcca aaaatagcct agaaggcggt ttttatggac caaacgccga ggagctggca   1260
ggtaaattcc taaccaatga caacaaactc tttggcgtct tggtgctaa acgagagagt    1320
aaagctgggg aaaaaaccga agccatctta gatgcctatg cacttgggac atttaacaaa   1380
aataacgcaa ccacattcac ccccatttacc aaaaacaaac tggataactt tggcaatgcc  1440
aaaaagttgg tcttgggttc taccgtcatt gatttggtgc ctaccggtgt caccaaagat   1500
gtcaatgaat tcaccaaaaa caagccagat tctgccacaa acaaagcggg cgagactttg   1560
atggtgaatg ataaagttag cgtcaaaacc tatggctatg cagaaacatt tgaataccta   1620
aaatttggtg agctcagtgt cggcacaagc aacagcgtct tttttacaagg cgaacgcacc   1680
gctaccacag gcgagaaagc cgtaccaacc aaaggcacag ccaaatattt ggggaactgg   1740
gtaggataca tcacaggaaa ggactcatca aaaagcttta tgaggccca agatgttgct    1800
gattttgaca ttgactttga gaaaaaatca gttaaaggca aactgaccac caaagaccgc   1860
caagaccctg tatttaacat cacaggtgac atcgcaggca atggctggac aggcaaagcc   1920
agcaccacca aagcggacgc aggggggctac aagatagatt ctagcagtac aggcaaatcc   1980
atcgtcatca aagatgccga ggttacaggg ggcttttatg gtccaaatgc aaacgagatg   2040
ggcgggtcat ttacacacaa caccgatgac agtaaagcct ctgtggtctt tggcacaaaa   2100
agacaagaag aagttaagta g                                             2121
```

<210> SEQ ID NO 2
<211> LENGTH: 706
<212> TYPE: PRT
<213> ORGANISM: Moraxella catarrhalis -continued

<400> SEQUENCE: 2

```
Met Lys His Ile Pro Leu Thr Thr Leu Cys Val Ala Ile Ser Ala Val
 1               5                  10                  15

Leu Leu Thr Ala Cys Gly Gly Ser Gly Gly Ser Asn Pro Ala Pro
             20                  25                  30

Thr Pro Ile Pro Asn Ala Ser Gly Ser Gly Asn Thr Gly Asn Thr Gly
             35                  40                  45

Asn Ala Gly Gly Thr Asp Asn Thr Ala Asn Ala Gly Asn Thr Gly Gly
 50                  55                  60

Thr Asn Ser Gly Thr Gly Ser Ala Asn Thr Pro Glu Pro Lys Tyr Lys
 65                  70                  75                  80

Asp Val Pro Thr Asp Glu Asn Lys Lys Asp Glu Val Ser Gly Ile Gln
                 85                  90                  95

Glu Pro Ala Met Gly Tyr Gly Met Ala Leu Ser Lys Met Asn Leu His
                100                 105                 110

Lys Gln Gln Asp Thr Pro Leu Asp Glu Lys Asp Ile Ile Thr Leu Asp
            115                 120                 125

Gly Lys Lys Gln Val Ala Lys Gly Glu Lys Ser Pro Leu Pro Phe Ser
130                 135                 140

Leu Asp Val Glu Asn Lys Leu Leu Asp Gly Tyr Ile Ala Lys Met Asn
145                 150                 155                 160

Glu Ala Asp Lys Asn Ala Ile Gly Asp Arg Ile Lys Lys Asp Asn Lys
                165                 170                 175

Asp Lys Ser Leu Ser Lys Ala Glu Leu Ala Lys Gln Ile Lys Glu Asp
            180                 185                 190

Val Arg Lys Ser His Glu Phe Gln Gln Val Leu Ser Ser Leu Lys Asn
        195                 200                 205

Lys Ile Phe His Ser Asn Asp Gly Thr Thr Lys Ala Thr Thr Arg Asp
210                 215                 220

Leu Gln Tyr Val Asp Tyr Gly Tyr Tyr Leu Val Asn Asp Gly Asn Tyr
225                 230                 235                 240

Leu Thr Val Lys Thr Asp Glu Leu Trp Asn Leu Gly Pro Val Gly Gly
                245                 250                 255

Val Phe Tyr Asn Gly Thr Thr Thr Ala Lys Glu Leu Pro Thr Gln Asp
            260                 265                 270

Ala Val Lys Tyr Lys Gly His Trp Asp Phe Met Thr Asp Val Ala Lys
        275                 280                 285

Gln Arg Asn Arg Phe Ser Glu Val Lys Glu Asn Leu Gln Ala Gly Arg
290                 295                 300

Tyr Tyr Gly Ala Ser Ser Lys Asp Glu Tyr Asn Arg Leu Leu Thr Asp
305                 310                 315                 320

Glu Lys Asn Lys Pro Glu Arg Tyr Asn Gly Glu Tyr Gly His Ser Ser
                325                 330                 335

Glu Phe Thr Val Asn Phe Lys Asp Lys Lys Leu Thr Gly Glu Leu Phe
            340                 345                 350

Ser Asn Leu Gln Asp Ser Arg Lys Gly Asn Val Thr Lys Thr Lys Arg
        355                 360                 365

Tyr Asp Ile Asp Ala Asn Ile Tyr Gly Asn Arg Phe Arg Gly Ser Ala
370                 375                 380

Thr Ala Ser Asp Lys Ala Glu Ala Ser Lys Thr Lys His Pro Phe Thr
385                 390                 395                 400

Ser Asp Ala Lys Asn Ser Leu Glu Gly Gly Phe Tyr Gly Pro Asn Ala
                405                 410                 415
```

-continued

```
Glu Glu Leu Ala Gly Lys Phe Leu Thr Asn Asp Asn Lys Leu Phe Gly
            420                 425                 430
Val Phe Gly Ala Lys Arg Glu Ser Lys Ala Gly Glu Lys Thr Glu Ala
            435                 440                 445
Ile Leu Asp Ala Tyr Ala Leu Gly Thr Phe Asn Lys Asn Asn Ala Thr
            450                 455                 460
Thr Phe Thr Pro Phe Thr Lys Lys Gln Leu Asp Asn Phe Gly Asn Ala
465                 470                 475                 480
Lys Lys Leu Val Leu Gly Ser Thr Val Ile Asp Leu Val Pro Thr Gly
            485                 490                 495
Val Thr Lys Asp Val Asn Glu Phe Thr Lys Asn Lys Pro Asp Ser Ala
            500                 505                 510
Thr Asn Lys Ala Gly Glu Thr Leu Met Val Asn Asp Lys Val Ser Val
            515                 520                 525
Lys Thr Tyr Gly Tyr Gly Arg Asn Phe Glu Tyr Leu Lys Phe Gly Glu
            530                 535                 540
Leu Ser Val Gly Thr Ser Asn Ser Val Phe Leu Gln Gly Glu Arg Thr
545                 550                 555                 560
Ala Thr Thr Gly Glu Lys Ala Val Pro Thr Lys Gly Thr Ala Lys Tyr
            565                 570                 575
Leu Gly Asn Trp Val Gly Tyr Ile Thr Gly Lys Asp Ser Ser Lys Ser
            580                 585                 590
Phe Asn Glu Ala Gln Asp Val Ala Asp Phe Asp Ile Asp Phe Glu Lys
            595                 600                 605
Lys Ser Val Lys Gly Lys Leu Thr Thr Lys Asp Arg Gln Asp Pro Val
            610                 615                 620
Phe Asn Ile Thr Gly Asp Ile Ala Gly Asn Gly Trp Thr Gly Lys Ala
625                 630                 635                 640
Ser Thr Thr Lys Ala Asp Ala Gly Gly Tyr Lys Ile Asp Ser Ser Ser
            645                 650                 655
Thr Gly Lys Ser Ile Val Ile Lys Asp Ala Glu Val Thr Gly Gly Phe
            660                 665                 670
Tyr Gly Pro Asn Ala Asn Glu Met Gly Gly Ser Phe Thr His Asn Thr
            675                 680                 685
Asp Asp Ser Lys Ala Ser Val Val Phe Gly Thr Lys Arg Gln Glu Glu
            690                 695                 700
Val Lys
705

<210> SEQ ID NO 3
<211> LENGTH: 2139
<212> TYPE: DNA
<213> ORGANISM: Moraxella catarrhalis

<400> SEQUENCE: 3
atgaaacaca ttcctttaac cacactgtgt gtggcaatct ctgccgtctt attaaccgct     60
tgtggtggca gtggtggttc aaatccacct gctcctacgc ccattccaaa tgcaggcggt    120
gcaggtaatg ctggtagcgg tactggcggt gcaggtagca ctgataatgc agccaatgca    180
ggcagtacag gcggtgcaag ctctggtaca ggcagtgcca gcacacaaaa accaaaatat    240
caagatgtgc aaccgataaa aataaaaaaa gatgaagtgt caggcattca agaacctgcc    300
atgggttatg gctggaatt aaagcttcgt aactggatac acaagaaaca ggaagaacat    360
gccaaaatca atacaaatga tgttgtaaaa cttgaaggtg acttgaagca taatccattt    420
```

-continued

```
gacaactcta tttggcaaaa catcaaaaat agcaaagaag tacaaactgt ttacaaccaa      480
gagaagcaaa acattgaaaa tcaaatcaaa aaagaaaata agaacttga taaaacggca      540 ctaaaagctc ttattgaaaa agttcttgat gactatctaa caagtcttgc taaacccatt     600
tatgaaaaaa atattaatga ttcacatgat aagcagaata agcacgcac tcgtgatttg      660 aagtatgtgc gttctggtta tatttatcgc tcaggttatt ctaatatcga cattcaaaag    720
aaaatagcta aaactggttt tgatggtgct ttattttata aaggtacaca aactgctaaa    780
caattgcctg tatctgaggt taagtataaa ggcacttggg attttatgac cgatgccaaa    840
aaaggacaat catttagcag ttttgaaaga cgagctggtg atcgctatag tgcaatgtct    900
tcccatgagt acccatcttt attaactgat gataaaaaca accagataa ttataacgat     960 gaatatggtc atagcagtga gtttacggta gattttagta aaagagcct aacaggtggg    1020 ctgtttagta acctacaaga ccaccataag ggcaaggtta cgaaaaccaa acgctatgac   1080
atcaatgccc gtatccacgg taaccgcttc cgtggcagtg ccaccgcaat caataaagat   1140
aatgaaagca agccaaaca ccccttttacc agcgatgccg acaataggct agaaggcgt   1200 ttttatggac caaacgccga ggagctggca ggtaaattcc taaccgatga caacaaactc   1260
tttggtgtct ttggtgctaa acaagagagt gaagctaagg aaaccgaagc catcttagat   1320
gcttatgcac ttgggacatt taataaatct ggtacgacca atcctgcctt taccgccaat    1380
agtaaaaaag aactggataa ctttggcaat attaataaat tggtcttggg ttctactgtg    1440 atagaccta ctcaaggtaa tgattttgta aaaaccattg ataaagaaaa gccagccacc   1500
actaccaatc aagcaggcga gcctttgacg gtgaatgata aggttcgggt acaagtttgt   1560
tgtagcaatc ttgagcatct aaaatttggc tcactgagta tcggtgatag taatagcgtc   1620
tttttacaag gtgaacgcac cgctaccaaa ggtgataaag ataaagccat gccagttgca   1680
ggaaatgcta ataccgtgg tacatgggca ggctatgttg caggctctgg caataccagc    1740
aaagcctatg aagcccaaca atttgctgac aatgccaacc gtgccgagtt tgatgtagac   1800
tttgctaaca aaagcctaac tggtaagctt attccaaata cgagcagtga tggtaaatct    1860
gcttttgata ttactgctac aattgatggc aatggtttta gtggtaaagc caatacacca   1920
gatattgaaa caggtgggtt aaagattgac agtaagaaca gtgaaagcgg ccgagtaatt    1980
gtgaaagatg ctatagttat aggtggcttt tatggtccac aagctaatga actgggtggc    2040
tcatttacct acaagagcaa tgatgctgga aatcaagaca aagacagtag tgcatctgtg    2100
gtctttggtg caagaaaaca acaagaagtc aaaccatga                           2139
```

<210> SEQ ID NO 4
<211> LENGTH: 712
<212> TYPE: PRT
<213> ORGANISM: Moraxella catarrhalis

<400> SEQUENCE: 4

```
Met Lys His Ile Pro Leu Thr Thr Leu Cys Val Ala Ile Ser Ala Val
 1               5                  10                  15

Leu Leu Thr Ala Cys Gly Gly Ser Gly Gly Ser Asn Pro Pro Ala Pro
            20                  25                  30

Thr Pro Ile Pro Asn Ala Gly Gly Ala Gly Asn Ala Gly Ser Gly Thr
        35                  40                  45

Gly Gly Ala Gly Ser Thr Asp Asn Ala Ala Asn Ala Gly Ser Thr Gly
    50                  55                  60
```

-continued

| | | | | | | | | | | | | | | |
|---|---|---|---|---|---|---|---|---|---|---|---|---|---|---|
|Gly|Ala|Ser|Ser|Gly|Thr|Gly|Ser|Ala|Ser|Thr|Gln|Lys|Pro|Lys|Tyr|
|65| | | |70| | | |75| | | |80|

Gly Ala Ser Ser Gly Thr Gly Ser Ala Ser Thr Gln Lys Pro Lys Tyr
 65                  70                  75                  80

Gln Asp Val Pro Thr Asp Lys Asn Lys Lys Asp Glu Val Ser Gly Ile
                 85                  90                  95

Gln Glu Pro Ala Met Gly Tyr Gly Val Glu Leu Lys Leu Arg Asn Trp
            100                 105                 110

Ile Pro Gln Glu Gln Glu His Ala Lys Ile Asn Thr Asn Asp Val
            115                 120             125

Val Lys Leu Glu Gly Asp Leu Lys His Asn Pro Phe Asp Asn Ser Ile
    130                 135             140

Trp Gln Asn Ile Lys Asn Ser Lys Glu Val Gln Thr Val Tyr Asn Gln
145                 150                 155                 160

Glu Lys Gln Asn Ile Glu Asn Gln Ile Lys Lys Glu Asn Lys Glu Leu
                165                 170                 175

Asp Lys Thr Ala Leu Lys Ala Leu Ile Glu Lys Val Leu Asp Asp Tyr
            180                 185                 190

Leu Thr Ser Leu Ala Lys Pro Ile Tyr Glu Lys Asn Ile Asn Asp Ser
        195                 200                 205

His Asp Lys Gln Asn Lys Ala Arg Thr Arg Asp Leu Lys Tyr Val Arg
    210                 215                 220

Ser Gly Tyr Ile Tyr Arg Ser Gly Tyr Ser Asn Ile Asp Ile Gln Lys
225                 230                 235                 240

Lys Ile Ala Lys Thr Gly Phe Asp Gly Ala Leu Phe Tyr Lys Gly Thr
                245                 250                 255

Gln Thr Ala Lys Gln Leu Pro Val Ser Glu Val Lys Tyr Lys Gly Thr
            260                 265                 270

Trp Asp Phe Met Thr Asp Ala Lys Lys Gly Gln Ser Phe Ser Ser Phe
        275                 280                 285

Glu Arg Arg Ala Gly Asp Arg Tyr Ser Ala Met Ser Ser His Glu Tyr
    290                 295                 300

Pro Ser Leu Leu Thr Asp Asp Lys Asn Lys Pro Asp Asn Tyr Asn Asp
305                 310                 315                 320

Glu Tyr Gly His Ser Ser Glu Phe Thr Val Asp Phe Ser Lys Lys Ser
                325                 330                 335

Leu Thr Gly Gly Leu Phe Ser Asn Leu Gln Asp His His Lys Gly Lys
            340                 345                 350

Val Thr Lys Thr Lys Arg Tyr Asp Ile Asn Ala Arg Ile His Gly Asn
        355                 360                 365

Arg Phe Arg Gly Ser Ala Thr Ala Ile Asn Lys Asp Asn Glu Ser Lys
    370                 375                 380

Ala Lys His Pro Phe Thr Ser Asp Ala Asp Asn Arg Leu Glu Gly Gly
385                 390                 395                 400

Phe Tyr Gly Pro Asn Ala Glu Glu Leu Ala Gly Lys Phe Leu Thr Asp
                405                 410                 415

Asp Asn Lys Leu Phe Gly Val Phe Gly Ala Lys Gln Glu Ser Glu Ala
            420                 425                 430

Lys Glu Thr Glu Ala Ile Leu Asp Ala Tyr Ala Leu Gly Thr Phe Asn
        435                 440                 445

Lys Ser Gly Thr Thr Asn Pro Ala Phe Thr Ala Asn Ser Lys Lys Glu
    450                 455                 460

Leu Asp Asn Phe Gly Asn Ile Asn Lys Leu Val Leu Gly Ser Thr Val
465                 470                 475                 480

Ile Asp Leu Thr Gln Gly Asn Asp Phe Val Lys Thr Ile Asp Lys Glu

```
                         485                 490                 495
Lys Pro Ala Thr Thr Asn Gln Ala Gly Glu Pro Leu Thr Val Asn
            500                 505                 510

Asp Lys Val Arg Val Gln Val Cys Cys Ser Asn Leu Glu His Leu Lys
            515                 520                 525

Phe Gly Ser Leu Ser Ile Gly Asp Ser Asn Ser Val Phe Leu Gln Gly
            530                 535                 540

Glu Arg Thr Ala Thr Lys Gly Asp Lys Asp Lys Ala Met Pro Val Ala
545                 550                 555                 560

Gly Asn Ala Lys Tyr Arg Gly Thr Trp Ala Gly Tyr Val Ala Gly Ser
                565                 570                 575

Gly Asn Thr Ser Lys Ala Tyr Glu Ala Gln Gln Phe Ala Asp Asn Ala
            580                 585                 590

Asn Arg Ala Glu Phe Asp Val Asp Phe Ala Asn Lys Ser Leu Thr Gly
            595                 600                 605

Lys Leu Ile Pro Asn Thr Ser Ser Asp Gly Lys Ser Ala Phe Asp Ile
            610                 615                 620

Thr Ala Thr Ile Asp Gly Asn Gly Phe Ser Gly Lys Ala Asn Thr Pro
625                 630                 635                 640

Asp Ile Glu Thr Gly Gly Leu Lys Ile Asp Ser Lys Asn Ser Glu Ser
                645                 650                 655

Gly Arg Val Ile Val Lys Asp Ala Ile Val Ile Gly Gly Phe Tyr Gly
                660                 665                 670

Pro Gln Ala Asn Glu Leu Gly Ser Phe Thr Tyr Lys Ser Asn Asp
            675                 680                 685

Ala Gly Asn Gln Asp Lys Asp Ser Ser Ala Ser Val Val Phe Gly Ala
            690                 695                 700

Arg Lys Gln Gln Glu Val Lys Pro
705                 710

<210> SEQ ID NO 5
<211> LENGTH: 2142
<212> TYPE: DNA
<213> ORGANISM: Moraxella catarrhalis

<400> SEQUENCE: 5
atgaaacaca ttcctttaac cacactgtgt gtggcaatct ctgccgtctt attaaccgct      60
tgtggtggca gtggtggttc aaatccacct gctcctacgc ccatcccaaa tgcaggcagt     120
gcaggtaatg ctggcggtac aggaaataca ggcggtactg cagtactga taatgtaggc     180 aatgctggcg gtgcaaactc tggtacaggc aatgcaggta attcaggtaa tgcaaactct     240
ggtacaggca gtgccaacac accagaacca aaatatcaag atgtgccaac cgataaaaat     300
gaaaaagaac aagtttcatc cattcaagaa cctgccatgg ttatgcaat ggaattaaag      360 cttcgtaatg ctcaccctct taacccaaat aaaaataag aggctgaaaa acgcattgcc      420
ttagaccaaa aagatttggt ggcagtagag ggcgacctaa ccaacattcc ttttgataaa     480
aatcttattg aataccttaa aaaatcatcc gaggttgtaa gtaaatttga agcacaaaaa     540
ggcggtattg aaaataacac aagactgaca cacaaagatt tatcatcaga gcaaaaagaa     600
gcaaagtcaa agaagcgttt ggacaatgct ttaactcaat tgcccaagaa aatacaag       660 gagctaattg agaacgccca tgataaaaaa tctgacgcac gcaaccgtga tctagaatat     720
gtcaagtctg gttttaacta tctttctgga tataccgcca ccgaccacga caaaaaaacc     780
aattatcgtg gctattatgg tgcgttgtat tataaaggca gcgaaaccgc caaagagcta     840
```

```
ccacaaacaa gtgcaaaata taaaggttat tgggacttta tgacagatgc cacacttgat    900
aacaaataca cggatttgcc aggtatcgcc agacaaaccc agtggcgtag tcttgtttct    960
actgatgagt atgcaacgct cttgacagac aaaaataaca agcccagtga ttacaatggt   1020
gcatatggtc atagcagtga atttgatgtt aattttgctg ataaaaaaat taaaggcaaa   1080
cttatcagta atcagttatc aggcacagct gtaaccgcca aagagcgtta taaaatagaa   1140
gctgatatcc acggcaaccg cttccgtggc agtgccaccg caagcgataa agcagaagac   1200
agcaaaaccc aacacccctt taccagcgat gctacaaaca agctagaagg tggttttat    1260
ggaccaaaag gcgaggagct ggcaggtaaa ttcttaaccg atgacaacaa actctttggg   1320
gtctttggtg ctaaacgaga taagtagaaa aaaccgaag ccatcttaga tgcctatgca   1380
cttgggacat ttaataatac aaataaagca accacattca ccccatttac caaaaaacaa   1440
ctggataact ttgcaatgc caaaaagttg gtcttgggtt ctaccgtcat taatttggtg   1500
tctaccgatg ccaccaaaaa tgaattcacc aaaaaattca ccaaagacaa gccaacttct   1560
gccacaaaca aagcgggcga cctttgatg gtgaatgatg aagttatcgt caaaacctat    1620
ggcaaaaact ttgaatacct aaaatttggt gagcttagtg tcggtgatag ccatagcgtc   1680
tttttacaag gcgaacgcac cgctaccaca ggcgagaaag ccgtaccaac cacaggcaaa   1740
gccaaatatc tggggaactg gtaggatac atcacaggag cgggcacagg aaaaagcttt    1800
aatgaggccc aagatattgc tgatttttgac attgactttg agagaaaatc agttaaaggc   1860
aaactgacca cccaaggccg cacagatcct gtctttaaca tcaaggtga aattgcaggc    1920
aatggctgga caggcaaagc cagcaccacc aaagcggacg caggaggcta caagatagat   1980
tctagcagta caggcaaatc catcgtcatc gaaaatgccg aagttactgg gggcttttat   2040
ggtccaaatg caaacgagat gggcgggtca tttacacacg ataccgatga cagtaaagcc   2100
tctgtggtct ttggcacaaa aagcaacaa gaagttaagt ag                       2142
```

<210> SEQ ID NO 6
<211> LENGTH: 713
<212> TYPE: PRT
<213> ORGANISM: Moraxella catarrhalis

<400> SEQUENCE: 6

```
Met Lys His Ile Pro Leu Thr Thr Leu Cys Val Ala Ile Ser Ala Val
  1               5                  10                  15

Leu Leu Thr Ala Cys Gly Gly Ser Gly Gly Ser Asn Pro Pro Ala Pro
             20                  25                  30

Thr Pro Ile Pro Asn Ala Gly Ser Ala Gly Asn Ala Gly Gly Thr Gly
         35                  40                  45

Asn Thr Gly Gly Thr Gly Ser Thr Asp Asn Val Gly Asn Ala Gly Gly
     50                  55                  60

Ala Asn Ser Gly Thr Gly Asn Ala Gly Asn Ser Gly Asn Ala Asn Ser
 65                  70                  75                  80

Gly Thr Gly Ser Ala Asn Thr Pro Glu Pro Lys Tyr Gln Asp Val Pro
                 85                  90                  95

Thr Asp Lys Asn Glu Lys Glu Gln Val Ser Ser Ile Gln Glu Pro Ala
            100                 105                 110

Met Gly Tyr Ala Met Glu Leu Lys Leu Arg Asn Ala His Pro Leu Asn
        115                 120                 125

Pro Asn Lys Asn Lys Glu Ala Glu Lys Arg Ile Ala Leu Asp Gln Lys
    130                 135                 140
```

-continued

```
Asp Leu Val Ala Val Glu Gly Asp Leu Thr Asn Ile Pro Phe Asp Lys
145                 150                 155                 160

Asn Leu Ile Glu Tyr Leu Lys Lys Ser Ser Glu Val Val Ser Lys Phe
            165                 170                 175

Glu Ala Gln Lys Gly Gly Ile Glu Asn Asn Thr Arg Leu Thr His Lys
        180                 185                 190

Asp Leu Ser Ser Glu Gln Lys Glu Ala Lys Val Lys Glu Ala Leu Asp
    195                 200                 205

Asn Ala Leu Thr Gln Phe Ala Gln Glu Lys Tyr Lys Glu Leu Ile Glu
210                 215                 220

Asn Ala His Asp Lys Lys Ser Asp Ala Arg Asn Arg Asp Leu Glu Tyr
225                 230                 235                 240

Val Lys Ser Gly Phe Asn Tyr Leu Ser Gly Tyr Thr Ala Thr Asp His
            245                 250                 255

Asp Lys Lys Thr Asn Tyr Arg Gly Tyr Tyr Gly Ala Leu Tyr Tyr Lys
        260                 265                 270

Gly Ser Glu Thr Ala Lys Glu Leu Pro Gln Thr Ser Ala Lys Tyr Lys
    275                 280                 285

Gly Tyr Trp Asp Phe Met Thr Asp Ala Thr Leu Asp Asn Lys Tyr Thr
290                 295                 300

Asp Leu Pro Gly Ile Ala Arg Gln Thr Gln Trp Arg Ser Leu Val Ser
305                 310                 315                 320

Thr Asp Glu Tyr Ala Thr Leu Leu Thr Asp Lys Asn Asn Lys Pro Ser
            325                 330                 335

Asp Tyr Asn Gly Ala Tyr Gly His Ser Ser Glu Phe Asp Val Asn Phe
        340                 345                 350

Ala Asp Lys Lys Ile Lys Gly Lys Leu Ile Ser Asn Gln Leu Ser Gly
    355                 360                 365

Thr Ala Val Thr Ala Lys Glu Arg Tyr Lys Ile Glu Ala Asp Ile His
370                 375                 380

Gly Asn Arg Phe Arg Gly Ser Ala Thr Ala Ser Asp Lys Ala Glu Asp
385                 390                 395                 400

Ser Lys Thr Gln His Pro Phe Thr Ser Asp Ala Thr Asn Lys Leu Glu
            405                 410                 415

Gly Gly Phe Tyr Gly Pro Lys Gly Glu Glu Leu Ala Gly Lys Phe Leu
        420                 425                 430

Thr Asp Asp Asn Lys Leu Phe Gly Val Phe Gly Ala Lys Arg Asp Lys
    435                 440                 445

Val Glu Lys Thr Glu Ala Ile Leu Asp Ala Tyr Ala Leu Gly Thr Phe
450                 455                 460

Asn Asn Thr Asn Lys Ala Thr Thr Phe Thr Pro Phe Thr Lys Lys Gln
465                 470                 475                 480

Leu Asp Asn Phe Gly Asn Ala Lys Lys Leu Val Leu Gly Ser Thr Val
            485                 490                 495

Ile Asn Leu Val Ser Thr Asp Ala Thr Lys Asn Glu Phe Thr Lys Lys
        500                 505                 510

Phe Thr Lys Asp Lys Pro Thr Ser Ala Thr Asn Lys Ala Gly Glu Thr
    515                 520                 525

Leu Met Val Asn Asp Glu Val Ile Val Lys Thr Tyr Gly Lys Asn Phe
530                 535                 540

Glu Tyr Leu Lys Phe Gly Glu Leu Ser Val Gly Asp Ser His Ser Val
545                 550                 555                 560
```

-continued

```
Phe Leu Gln Gly Glu Arg Thr Ala Thr Thr Gly Glu Lys Ala Val Pro
                565                 570                 575

Thr Thr Gly Lys Ala Lys Tyr Leu Gly Asn Trp Val Gly Tyr Ile Thr
            580                 585                 590

Gly Ala Gly Thr Gly Lys Ser Phe Asn Glu Ala Gln Asp Ile Ala Asp
        595                 600                 605

Phe Asp Ile Asp Phe Glu Arg Lys Ser Val Lys Gly Lys Leu Thr Thr
    610                 615                 620

Gln Gly Arg Thr Asp Pro Val Phe Asn Ile Lys Gly Glu Ile Ala Gly
625                 630                 635                 640

Asn Gly Trp Thr Gly Lys Ala Ser Thr Thr Lys Ala Asp Ala Gly Gly
                645                 650                 655

Tyr Lys Ile Asp Ser Ser Thr Gly Lys Ser Ile Val Ile Glu Asn
                660                 665                 670

Ala Glu Val Thr Gly Gly Phe Tyr Gly Pro Asn Ala Asn Glu Met Gly
            675                 680                 685

Gly Ser Phe Thr His Asp Thr Asp Ser Lys Ala Ser Val Val Phe
        690                 695                 700

Gly Thr Lys Arg Gln Gln Glu Val Lys
705                 710

<210> SEQ ID NO 7
<211> LENGTH: 702
<212> TYPE: PRT
<213> ORGANISM: Moraxella catarrhalis

<400> SEQUENCE: 7

Met Lys His Ile Pro Leu Thr Thr Leu Cys Val Ala Ile Ser Ala Val
  1               5                  10                  15

Leu Leu Thr Ala Cys Gly Gly Ser Gly Gly Ser Asn Pro Ala Pro
                20                  25                  30

Thr Pro Ile Pro Asn Ala Ser Gly Ser Gly Asn Thr Gly Asn Thr Gly
            35                  40                  45

Asn Ala Gly Gly Thr Asp Asn Thr Ala Asn Ala Gly Asn Thr Gly Gly
        50                  55                  60

Thr Asn Ser Gly Thr Gly Ser Ala Asn Thr Pro Glu Pro Lys Tyr Gln
 65                 70                  75                  80

Asp Val Pro Thr Glu Lys Asn Glu Lys Asp Lys Val Ser Ser Ile Gln
                85                  90                  95

Glu Pro Ala Met Gly Tyr Gly Met Ala Leu Ser Lys Ile Asn Leu His
            100                 105                 110

Asn Arg Gln Asp Thr Pro Leu Asp Glu Lys Asn Ile Ile Thr Leu Asp
        115                 120                 125

Gly Lys Lys Gln Val Ala Glu Gly Lys Lys Ser Pro Leu Pro Phe Ser
    130                 135                 140

Leu Asp Val Glu Asn Lys Leu Leu Asp Gly Tyr Ile Ala Lys Met Asn
145                 150                 155                 160

Val Ala Asp Lys Asn Ala Ile Gly Asp Arg Ile Lys Lys Gly Asn Lys
                165                 170                 175

Glu Ile Ser Asp Glu Glu Leu Ala Lys Gln Ile Lys Glu Ala Val Arg
            180                 185                 190

Lys Ser His Glu Phe Gln Gln Val Leu Ser Ser Leu Glu Asn Lys Ile
        195                 200                 205

Phe His Ser Asn Asp Gly Thr Lys Ala Thr Thr Arg Asp Leu Lys
    210                 215                 220
```

-continued

```
Tyr Val Asp Tyr Gly Tyr Leu Ala Asn Asp Gly Asn Tyr Leu Thr
225                 230                 235                 240

Val Lys Thr Asp Lys Leu Trp Asn Leu Gly Pro Val Gly Val Phe
            245                 250                 255

Tyr Asn Gly Thr Thr Thr Ala Lys Glu Leu Pro Thr Gln Asp Ala Val
                260                 265                 270

Lys Tyr Lys Gly His Trp Asp Phe Met Thr Asp Val Ala Asn Arg Arg
            275                 280                 285

Asn Arg Phe Ser Glu Val Lys Glu Asn Ser Gln Ala Gly Trp Tyr Tyr
    290                 295                 300

Gly Ala Ser Ser Lys Asp Glu Tyr Asn Arg Leu Leu Thr Lys Glu Asp
305                 310                 315                 320

Ser Ala Pro Asp Gly His Ser Gly Glu Tyr Gly His Ser Ser Glu Phe
                325                 330                 335

Thr Val Asn Phe Lys Glu Lys Leu Thr Gly Lys Leu Phe Ser Asn
                340                 345                 350

Leu Gln Asp Arg His Lys Gly Asn Val Thr Lys Thr Glu Arg Tyr Asp
                355                 360                 365

Ile Asp Ala Asn Ile His Gly Asn Arg Phe Arg Gly Ser Ala Thr Ala
370                 375                 380

Ser Asn Lys Asn Asp Thr Ser Lys His Pro Phe Thr Ser Asp Ala Asn
385                 390                 395                 400

Asn Arg Leu Glu Gly Gly Phe Tyr Gly Pro Lys Gly Glu Glu Leu Ala
                405                 410                 415

Gly Lys Phe Leu Thr Asn Asp Asn Lys Leu Phe Gly Val Phe Gly Ala
                420                 425                 430

Lys Arg Glu Ser Lys Ala Glu Lys Thr Glu Ala Ile Leu Asp Ala
            435                 440                 445

Tyr Ala Leu Gly Thr Phe Asn Thr Ser Asn Ala Thr Thr Phe Thr Pro
450                 455                 460

Phe Thr Glu Lys Gln Leu Asp Asn Phe Gly Asn Ala Lys Lys Leu Val
465                 470                 475                 480

Leu Gly Ser Thr Val Ile Asp Leu Val Pro Thr Asp Ala Thr Lys Asn
                485                 490                 495

Glu Phe Thr Lys Asp Lys Pro Glu Ser Ala Thr Asn Glu Ala Gly Glu
            500                 505                 510

Thr Leu Met Val Asn Asp Glu Val Ser Val Lys Thr Tyr Gly Lys Asn
            515                 520                 525

Phe Glu Tyr Leu Lys Phe Gly Glu Leu Ser Ile Gly Gly Ser His Ser
    530                 535                 540

Val Phe Leu Gln Gly Glu Arg Thr Ala Thr Thr Gly Glu Lys Ala Val
545                 550                 555                 560

Pro Thr Thr Gly Thr Ala Lys Tyr Leu Gly Asn Trp Val Gly Tyr Ile
                565                 570                 575

Thr Gly Lys Asp Thr Gly Thr Gly Thr Gly Lys Ser Phe Thr Asp Ala
            580                 585                 590

Gln Asp Val Ala Asp Phe Asp Ile Asp Phe Gly Asn Lys Ser Val Ser
    595                 600                 605

Gly Lys Leu Ile Thr Lys Gly Arg Gln Asp Pro Val Phe Ser Ile Thr
    610                 615                 620

Gly Gln Ile Ala Gly Asn Gly Trp Thr Gly Thr Ala Ser Thr Thr Lys
625                 630                 635                 640
```

-continued

```
Ala Asp Ala Gly Gly Tyr Lys Ile Asp Ser Ser Thr Gly Lys Ser
            645                 650                 655

Ile Val Ile Lys Asp Ala Asn Val Thr Gly Gly Phe Tyr Gly Pro Asn
        660                 665                 670

Ala Asn Glu Met Gly Gly Ser Phe Thr His Asn Ala Asp Asp Ser Lys
        675                 680                 685

Ala Ser Val Val Phe Gly Thr Lys Arg Gln Gln Glu Val Lys
        690                 695                 700

<210> SEQ ID NO 8
<211> LENGTH: 714
<212> TYPE: PRT
<213> ORGANISM: Moraxella catarrhalis

<400> SEQUENCE: 8

Met Lys His Ile Pro Leu Thr Thr Leu Cys Val Ala Ile Ser Ala Val
  1               5                  10                  15

Leu Leu Thr Ala Cys Gly Gly Ser Gly Gly Ser Asn Pro Ala Pro
             20                  25                  30

Thr Pro Ile Pro Asn Ala Ser Gly Ser Gly Asn Thr Gly Asn Thr Gly
         35                  40                  45

Asn Ala Gly Gly Thr Asp Asn Thr Ala Asn Ala Gly Asn Thr Gly Gly
 50                  55                  60

Thr Ser Ser Gly Thr Gly Ser Ala Ser Thr Ser Glu Pro Lys Tyr Gln
 65                  70                  75                  80

Asp Val Pro Thr Thr Pro Asn Asn Lys Glu Gln Val Ser Ser Ile Gln
                 85                  90                  95

Glu Pro Ala Met Gly Tyr Gly Met Ala Leu Ser Lys Ile Asn Leu Tyr
            100                 105                 110

Asp Gln Gln Asp Thr Pro Leu Asp Ala Lys Asn Ile Ile Thr Leu Asp
        115                 120                 125

Gly Lys Lys Gln Val Ala Asp Asn Gln Lys Ser Pro Leu Pro Phe Ser
    130                 135                 140

Leu Asp Val Glu Asn Lys Leu Leu Asp Gly Tyr Ile Ala Lys Met Asn
145                 150                 155                 160

Glu Ala Asp Lys Asn Ala Ile Gly Glu Arg Ile Lys Arg Glu Asn Glu
                165                 170                 175

Gln Asn Lys Lys Ile Ser Asp Glu Glu Leu Ala Lys Lys Ile Lys Glu
            180                 185                 190

Asn Val Arg Lys Ser Pro Glu Phe Gln Gln Val Leu Ser Ser Ile Lys
        195                 200                 205

Ala Lys Thr Phe His Ser Asn Asp Lys Thr Thr Lys Ala Thr Thr Arg
    210                 215                 220

Asp Leu Lys Tyr Val Asp Tyr Gly Tyr Tyr Leu Val Asn Asp Ala Asn
225                 230                 235                 240

Tyr Leu Thr Val Lys Thr Asp Asn Pro Lys Leu Trp Asn Ser Gly Pro
                245                 250                 255

Val Gly Gly Val Phe Tyr Asn Gly Ser Thr Thr Ala Lys Glu Leu Pro
            260                 265                 270

Thr Gln Asp Ala Val Lys Tyr Lys Gly His Trp Asp Phe Met Thr Asp
        275                 280                 285

Val Ala Lys Lys Arg Asn Arg Phe Ser Glu Val Lys Glu Thr Tyr Gln
    290                 295                 300

Ala Gly Trp Trp Tyr Gly Ala Ser Ser Lys Asp Glu Tyr Asn Arg Leu
305                 310                 315                 320
```

-continued

```
Leu Thr Lys Ala Asp Ala Ala Pro Asp Asn Tyr Ser Gly Glu Tyr Gly
            325                 330                 335
His Ser Ser Glu Phe Thr Val Asn Phe Lys Glu Lys Leu Thr Gly
            340                 345                 350
Glu Leu Phe Ser Asn Leu Gln Asp Ser His Lys Gln Lys Val Thr Lys
            355                 360                 365
Thr Lys Arg Tyr Asp Ile Lys Ala Asp Ile His Gly Asn Arg Phe Arg
    370                 375                 380
Gly Ser Ala Thr Ala Ser Asp Lys Ala Glu Asp Ser Lys Ser Lys His
385                 390                 395                 400
Pro Phe Thr Ser Asp Ala Lys Asp Lys Leu Glu Gly Phe Tyr Gly
            405                 410                 415
Pro Lys Gly Glu Glu Leu Ala Gly Lys Phe Leu Thr Asp Asn Lys
            420                 425                 430
Leu Phe Gly Val Phe Gly Ala Lys Gln Glu Gly Asn Val Glu Lys Thr
            435                 440                 445
Glu Ala Ile Leu Asp Ala Tyr Ala Leu Gly Thr Phe Asn Lys Pro Gly
    450                 455                 460
Thr Thr Asn Pro Ala Phe Thr Ala Asn Ser Lys Lys Glu Leu Asp Asn
465                 470                 475                 480
Phe Gly Asn Ala Lys Lys Leu Val Leu Gly Ser Thr Val Ile Asp Leu
            485                 490                 495
Val Pro Thr Asp Ala Thr Lys Asp Val Asn Glu Phe Lys Glu Lys Pro
            500                 505                 510
Lys Ser Ala Thr Asn Lys Ala Gly Glu Thr Leu Met Val Asn Asp Glu
            515                 520                 525
Val Ser Val Lys Thr Tyr Gly Lys Asn Phe Glu Tyr Leu Lys Phe Gly
            530                 535                 540
Glu Leu Ser Val Gly Gly Ser His Ser Val Phe Leu Gln Gly Glu Arg
545                 550                 555                 560
Thr Ala Thr Thr Gly Glu Lys Ala Val Pro Thr Thr Gly Lys Ala Lys
            565                 570                 575
Tyr Leu Gly Asn Trp Val Gly Tyr Ile Thr Gly Ala Asp Ser Ser Lys
            580                 585                 590
Gly Ser Thr Asp Gly Lys Gly Phe Thr Asp Ala Lys Asp Ile Ala Asp
            595                 600                 605
Phe Asp Ile Asp Phe Glu Lys Lys Ser Val Asn Gly Lys Leu Thr Thr
    610                 615                 620
Lys Asp Arg Gln Asp Pro Val Phe Asn Ile Thr Gly Glu Ile Ala Gly
625                 630                 635                 640
Asn Gly Trp Thr Gly Lys Ala Ser Thr Ala Glu Ala Asn Ala Gly Gly
            645                 650                 655
Tyr Lys Ile Asp Ser Ser Thr Gly Lys Ser Ile Val Ile Lys Asp
            660                 665                 670
Ala Val Val Thr Gly Gly Phe Tyr Gly Pro Asn Ala Thr Glu Met Gly
            675                 680                 685
Gly Ser Phe Thr His Asn Ser Gly Asn Lys Gly Lys Val Ser Val Val
            690                 695                 700
Phe Gly Thr Lys Lys Gln Glu Val Lys Lys
705                 710
```

<210> SEQ ID NO 9
<211> LENGTH: 708

<212> TYPE: PRT
<213> ORGANISM: Moraxella catarrhalis

<400> SEQUENCE: 9

```
Met Lys His Ile Pro Leu Thr Thr Leu Cys Val Ala Ile Ser Ala Val
  1               5                  10                  15

Leu Leu Thr Ala Cys Gly Gly Ser Ser Gly Gly Phe Asn Pro Pro Ala
             20                  25                  30

Ser Thr Pro Ile Pro Asn Ala Gly Asn Ser Gly Asn Ala Gly Asn Ala
         35                  40                  45

Gly Asn Ala Gly Gly Thr Gly Gly Ala Asn Ser Gly Ala Gly Asn Ala
     50                  55                  60

Gly Gly Thr Gly Gly Ala Asn Ser Gly Ala Gly Ser Ala Ser Thr Pro
 65                  70                  75                  80

Glu Pro Lys Tyr Lys Asp Val Pro Thr Asp Glu Asn Lys Lys Ala Glu
                 85                  90                  95

Val Ser Gly Ile Gln Glu Pro Ala Met Gly Tyr Gly Val Glu Leu Lys
            100                 105                 110

Leu Arg Asn Trp Ile Pro Gln Ala Gln Glu Glu His Ala Lys Ile Asn
        115                 120                 125

Thr Asn Asp Val Val Lys Leu Asp Asn Asp Leu Lys His Asn Pro Phe
130                 135                 140

Asp Asn Ser Ile Trp Gln Asn Ile Lys Asn Ser Lys Glu Val Gln Thr
145                 150                 155                 160

Val Tyr Asn Gln Glu Lys Gln Asn Ile Glu Asp Gln Ile Lys Arg Glu
                165                 170                 175

Asn Lys Gln Arg Pro Asp Lys Lys Asp Asp Val Ala Leu Gln Ala Tyr
            180                 185                 190

Ile Glu Lys Val Leu Asp Asp Arg Leu Thr Glu Leu Ala Lys Pro Ile
        195                 200                 205

Tyr Lys Lys Asn Thr Asn Tyr Ser His Asp Lys Gln Asn Lys Ala Arg
    210                 215                 220

Thr Arg Asp Leu Lys Tyr Val Arg Ser Gly Tyr Ile Tyr Arg Ser Gly
225                 230                 235                 240

Tyr Ser Asn Ile Ile Pro Lys His Ile Ala Lys Thr Gly Phe Asp Gly
                245                 250                 255

Ala Leu Phe Tyr Gln Gly Ser Gln Thr Ala Lys Gln Leu Pro Val Ser
            260                 265                 270

Gln Val Lys Tyr Lys Gly Thr Trp Asp Phe Met Thr Asp Ala Lys Lys
        275                 280                 285

Gly Gln Ser Phe Ser Ser Phe Gly Thr Ser Gln Arg Leu Ala Gly Asp
    290                 295                 300

Arg Tyr Ser Ala Met Ser Tyr His Glu Tyr Pro Ser Leu Leu Thr Asp
305                 310                 315                 320

Glu Lys Asn Lys Pro Asp Asn Tyr Asn Gly Glu Tyr Gly His Ser Ser
                325                 330                 335

Glu Phe Thr Val Asp Phe Ser Lys Lys Ser Leu Lys Gly Glu Leu Ser
            340                 345                 350

Ser Asn Leu Gln Asp Gly His Lys Gly Ser Val Asn Lys Thr Lys Arg
        355                 360                 365

Tyr Asp Ile Asp Ala Asn Ile Tyr Gly Asn Arg Phe Arg Gly Ser Ala
    370                 375                 380

Thr Ala Ser Asp Thr Thr Glu Ala Ser Lys Ser Lys His Pro Phe Thr
385                 390                 395                 400
```

-continued

```
Ser Asp Ala Lys Asn Ser Leu Glu Gly Gly Phe Tyr Gly Pro Asn Ala
            405                 410                 415
Glu Glu Leu Ala Gly Lys Phe Leu Thr Asn Asp Asn Lys Leu Phe Gly
        420                 425                 430
Val Phe Gly Ala Lys Arg Glu Ser Glu Ala Lys Glu Lys Thr Glu Ala
    435                 440                 445
Ile Leu Asp Ala Tyr Ala Leu Gly Thr Phe Asn Lys Pro Gly Thr Thr
450                 455                 460
Asn Pro Ala Phe Thr Ala Asn Ser Lys Lys Glu Leu Asp Asn Phe Gly
465                 470                 475                 480
Asn Ala Lys Lys Leu Val Leu Gly Ser Thr Val Ile Asp Leu Val Pro
            485                 490                 495
Thr Gly Ala Thr Lys Asp Val Asn Glu Phe Lys Glu Lys Pro Lys Ser
        500                 505                 510
Ala Thr Asn Lys Ala Gly Glu Thr Leu Met Val Asn Asp Glu Val Ile
    515                 520                 525
Val Lys Thr Tyr Gly Tyr Gly Arg Asn Phe Glu Tyr Leu Lys Phe Gly
530                 535                 540
Glu Leu Ser Ile Gly Gly Ser His Ser Val Phe Leu Gln Gly Glu Arg
545                 550                 555                 560
Thr Ala Glu Lys Ala Val Pro Thr Glu Gly Thr Ala Lys Tyr Leu Gly
            565                 570                 575
Asn Trp Val Gly Tyr Ile Thr Gly Lys Asp Thr Gly Thr Ser Thr Gly
        580                 585                 590
Lys Ser Phe Asn Glu Ala Gln Asp Ile Ala Asp Phe Asp Ile Asp Phe
    595                 600                 605
Glu Arg Lys Ser Val Lys Gly Lys Leu Thr Thr Gln Gly Arg Gln Asp
610                 615                 620
Pro Val Phe Asn Ile Thr Gly Gln Ile Ala Gly Asn Gly Trp Thr Gly
625                 630                 635                 640
Thr Ala Ser Thr Ala Lys Ala Asn Val Gly Gly Tyr Lys Ile Asp Ser
            645                 650                 655
Ser Ser Thr Gly Lys Ser Ile Val Ile Glu Asn Ala Lys Val Thr Gly
        660                 665                 670
Gly Phe Tyr Gly Pro Asn Ala Asn Glu Met Gly Gly Ser Phe Thr His
    675                 680                 685
Asp Thr Asp Asp Ser Lys Ala Ser Val Val Phe Gly Thr Lys Arg Gln
690                 695                 700
Glu Glu Val Lys
705
```

<210> SEQ ID NO 10
<211> LENGTH: 8266
<212> TYPE: DNA
<213> ORGANISM: Moraxella catarrhalis

<400> SEQUENCE: 10

```
gatgcctgcc ttgtgattgg ttggggtgta tcggtgtatc aaagtgcaaa agccaacagg      60
tggtcattga tgaatcaatc aaaacaaaac aacaaatcca aaaatccaa acaagtatta     120
aaacttagtg ccttgtcttt gggtctgctt aacatcacgc aggtggcact ggcaaacaca     180
acggccgata aggcggaggc aacagataag acaaaccttg ttgttgtctt ggatgaaact     240
gttgtaacag cgaagaaaaa cgcccgtaaa gccaacgaag ttacagggct tggtaaggtg     300
```

-continued

```
gtcaaaactg ccgagaccat caataaagaa caagtgctaa acattcgaga cttaacacgc    360
tatgaccctg gcattgctgt ggttgagcaa ggtcgtgggg caagctcagg ctattctatt    420
cgtggtatgg ataaaaatcg tgtggcggta ttggttgatg gcatcaatca agcccagcac    480
tatgccctac aaggccctgt ggcaggcaaa aattatgccg caggtggggc aatcaacgaa    540
atagaatacg aaaatgtccg ctccgttgag attagtaaag gtgcaaattc aagtgaatac    600
ggctctgggg cattatctgg ctctgtggca tttgttacca aaaccgccga tgacatcatc    660
aaagatggta agattggggg cgtgcagacc aaaaccgcct atgccagtaa aaataacgca    720
tgggttaatt ctgtggcagc agcaggcaag gcaggttctt ttagcggtct tatcatctac    780
accgaccgcc gtggtcaaga atacaaggca catgatgatg cctatcaggg tagccaaagt    840
tttgatagag cggtggcaac cactgaccca aataaccgaa catttttaat agcaaatgaa    900
tgtgccaatg gtaattatga ggcgtgtgct gctggcggtc aaaccaaact tcaagccaag    960
ccaaccaatg tgcgtgataa ggtcaatgtc aaagattata caggtcctaa ccgcctatc    1020 ccaaacccac tcacccaaga cagcaaatcc ttactgcttc gcccaggtta tcagctaaac    1080
gataagcact atgtcggtgg tgtgtatgaa atcaccaaac aaaactacgc catgcaagat    1140
aaaaccgtgc ctgcttatct ggcggttcat gacattgaaa atcaaggct cagcaaccat    1200 gcccaagcca atggctatta tcaaggcaat aatcttggtg aacgcattcg tgataccatt    1260
gggccagatt caggttatgg catcaactat gctcatggcg tattttatga tgaaaaacac    1320
caaaaagacc gcctagggct tgaatatgtt tatgacagca aggtgaaaaa taatggtttt    1380
gatgatgtgc gtgtgtctta tgataagcaa gacattacgc tacgcagcca gctgaccaac    1440
acgcactgtt caacctatcc gcacattgac aaaaattgta cgcctgatgt caataaacct    1500
ttttcggtaa aagaggtgga taacaatgcc tacaaagaac agcacaattt aatcaaagcc    1560
gtctttaaca aaaaaatggc gttgggcagt acgcatcatc acatcaacct gcaagttggc    1620
tatgataaat tcaattcaag cctgagccgt gtagaatatc gtttggcaac ccatcagtct    1680
tatcaaaaac ttgattacac cccaccaagt aaccctttgc cagataagtt taagcccatt    1740
ttaggttcaa acaacaaacc catttgcctt gatgcttatg gttatggtca tgaccatcca    1800
caggcttgta acgccaaaaa cagcacttat caaaattttg ccatcaaaaa aggcatagag    1860
caatacaacc aaaaaaccaa taccgataag attgattatc aagccatcat tgaccaatat    1920
gataaacaaa accccaacag caccctaaaa ccctttgaga aaatcaaaca aagtttgggg    1980
caagaaaaat acaacaagat agacgaactt ggctttaaag cttataaaga tttacgcaac    2040
gaatgggcgg gttggactaa tgacaacagc caacaaaatg ccaataaagg cacggataat    2100
atctatcagc caaatcaagc aactgtggtc aaagatgaca aatgtaaata tagcgagacc    2160
aacagctatg ctgattgctc aaccactcgc cacatcagtg gtgataatta tttcatcgct    2220
ttaaaagaca acatgaccat caataaatat gttgatttgg ggctgggtgc tcgctatgac    2280
agaatcaaac acaaatctga tgtgcctttg gtagacaaca gtgccagcaa ccagctgtct    2340
tggaattttg gcgtggtcgt caagcccacc aattggctgg acatcgctta tagaagctcg    2400
caaggctttc gcatgccaag ttttttctgaa atgtatggcg aacgctttgg cgtaaccatc    2460
ggtaaaggca cgcaacatgg ctgtaagggt ctttattaca tttgtcagca gactgtccat    2520
caaaccaagc taaaacctga aaatcccttt aaccaagaaa tcggagcgac tttacataac    2580
cacttaggca gtcttgaggt tagttatttt aaaaatcgct ataccgattt gattgttggt    2640
aaaagtgaag agattagaac cctaacccaa ggtgataatg caggcaaaca gcgtggtaaa    2700
```

```
ggtgatttgg gctttcataa tggacaagat gctgatttga caggaattaa cattcttggc    2760
agacttgacc taaacgctgc caatagtcgc cttccctatg gattatactc aacactggct    2820
tataacaaag ttgatgttaa aggaaaaacc ttaaacccaa ctttggcagg aacaaacata    2880
ctgtttgatg ccatccagcc atctcgttat gtggtgggc ttggctatga tgccccaagc     2940
caaaaatggg gagcaaacgc catatttacc cattctgatg ccaaaaatcc aagcgagctt    3000
ttggcagata agaacttagg taatggcaac attcaaacaa acaagccac caaagcaaaa     3060 tccacgccgt ggcaaacact tgatttgtca ggttatgtaa acataaaaga taattttacc    3120
ttgcgtgctg gcgtgtacaa tgtatttaat acctattaca ccacttggga ggctttacgc    3180
caaacagcaa aaggggcggt caatcagcat acaggactga gccaagataa gcattatggt    3240
cgctatgccg ctcctggacg caattaccaa ttggcacttg aaatgaagtt ttaaccagtg    3300
gctttgatgt gattttggca tgccaaatcc caatcaacca atgaataaag cccccattac    3360
catgagggct ttattttatc atcgctgagt atgctcttag cggtcatcac tcagattagt    3420 cattaatttta ttagcgatta atttattagt aatcacgctg ctctttgatg attttaagtg    3480
atgggtattc aagaacgatg tcatactcag caccgttttt ataggcttct acttcaaaga    3540
caggcttgcc taaaaagtca tcaacttcta tatcgccgac ttgatagcca cgagcagcaa    3600
gcatttgaat ggcttttttga cgattttggg caaagttgct gtcgccataa gcttgtgctt    3660
taatacggtc gttagcaact gcggtggtag agataccaac ggcaggcaac aaaacagcag    3720
cacttagtac gccagccaac agtttattgg ttaaattttt catagtagtt tcctaattat    3780
tatcattgta attcatgttt atcgttataa acaatcgtta taaataactg tgtcgtgata    3840
accattaatc acaagtgggt taaatgcctt ttgcccaatg gcaaataggc acaatgctct    3900
gcttgttcta tgatggtcta ttatgatcat cattttattg acctattttt ttaatcgtaa    3960
tgtttgtttg atgttagtat aaattttatc aatcaaacaa tcacaaatta tatcaatcat    4020
agacggtaaa caggcttcat attttacgca tatttcccca gatgtctgta gtgtttcata    4080
gatgatttgt aaaacaattg tcggtcatta ttatcaattg taaactgatg gctaatttgt    4140
aaccttatgg ctaatgataa tatgaataaa gcgttatact gtatcaaaga atgagtaaaa    4200
accatcaatg gtatcttatt tatcatcagg ttgtgttaat aagatgccaa ttaagcgact    4260
aattttgtaa attaattaat aatcattcat atttgtattt ttaaatacca taaaaaatgg    4320
taaaatatgc tcgcttttttt gataggagct gtcatgacaa tcacgcctgt ttataccaca    4380
ttcaccccca ccaaaacacc cataaaattt tttatggctg gcttgacttt tctaatcgct    4440
catatcagcc atgccgatga tggtcgcacc gacaatcaag agctaatcaa tcaagaaata    4500
gccacccttg aacccatcat taaccatgct cagcctgagt tattgtccca tgatgcatta    4560
acaccaaaaa tagaaccaat actggcacaa acaccaaatc ctgccgaaga tacgctcatc    4620
gccgatgagg cgttactgct tgataaccct gatttgctca atcacgccct aaattctgct    4680
gtcatgacca atcatatggc aggcgttcac gcattattgc ccatttatca aaaactgccc    4740
aaagaccatc aaaatggcat tttacttggg tatgccaatg ccttggctgc tttggataag    4800
ggcaacgcca aaaagccat tgatgagcta cgtcgcatca tcgccatcat gcctgaatat     4860
aatgtggtgc gttttcatct ggcaagggca ttatttatgg acaaacaaaa tgaagccgcc    4920
cttgaccagt ttaataaatt acatgctgac aacttgccag aggaggtgcg gcaggttgtt    4980
gggcagtaca gacaagcgct aaaacaacga gattcatgga catggcaagt aggcatgaat    5040
```

-continued

| | |
|---|---|
| ctggccaaag aagacaacat caatcaaacc cccaaaaaca ccacgcaagg tcaatggact | 5100 |
| tttgacaaac ccattgacgc catcaccctaa agctaccaat tggggcgga taaaaagtgg | 5160 |
| tctttgccca aagggcata tgtgggagcg aacgcccaaa tctatggcaa acatcatcaa | 5220 |
| aatcacaaaa aatacaacga ccattggggc agactggggg caaatttggg ctttgctgat | 5280 |
| gccaaaaaag accttagcat tgagacctat ggtgaaaaaa gattttatgg gcatgagcgt | 5340 |
| tataccgaca ccattggcat acgcatgtcg gttgattata gaatcaaccc aaaatttcaa | 5400 |
| agcctaaacg ccatagacat atcacgccta accaaccatc ggacgcctag ggctgacagt | 5460 |
| aataacactt tatacagtac ctcattgatt tattacccaa atgccacacg ctattatctt | 5520 |
| ttgggggcag acttttatga tgaaaaagtg ccacaagacc catctgacag ttatcaacgc | 5580 |
| cgtggcatac gcacagcgtg ggggcaagaa tgggcgggtg gtctttcaag ccgtgcccaa | 5640 |
| atcagcatca acaaacgcca ttaccaaggg gcaaacctaa ccagcggtgg acaaattcgc | 5700 |
| catgataaac agatgcaagc gtctttatcg ctttggcaca gagacattca caaatggggc | 5760 |
| atcacgccac ggctgaccat cagcacaaac atcaataaaa gcaatgacat caaggcaaat | 5820 |
| tatcacaaaa atcaaatgtt tgttgagttt agtcgcattt tttgatggga taagcacgcc | 5880 |
| ctactttgt ttttgtaaaa aaatgtgcca tcatagacaa tatcaagaaa aaatcaagaa | 5940 |
| aaaaagatta caaatttaat gataattgtt attgtttatg ttattattta tcaatgtaaa | 6000 |
| tttgccgtat tttgtctatc ataaatgcat ttatcaaatg ctcaaataaa tacgccaaat | 6060 |
| gcacattgtc agcatgccaa ataggcatc aacagacttt tttagataat accatcaacc | 6120 |
| catcagagga ttattttatg aaacacattc ctttaaccac actgtgtgtg gcaatctctg | 6180 |
| ccgtcttatt aaccgcttgt ggtggcagtg gtggttcaaa tccacctgct cctacgccca | 6240 |
| ttccaaatgc tagcggttca ggtaatactg gcaacactgg taatgctggc ggtactgata | 6300 |
| atacagccaa tgcaggtaat acaggcggta caaactctgg tacaggcagt gccaacacac | 6360 |
| cagagccaaa atatcaagat gtaccaactg agaaaaatga aaaagataaa gtttcatcca | 6420 |
| ttcaagaacc tgccatgggt tatgcatgg ctttgagtaa aattaatcta cacaaccgac | 6480 |
| aagacacgcc attagatgaa aaaaatatca ttaccttaga cggtaaaaaa caagttgcag | 6540 |
| aaggtaaaaa atcgccattg ccattttcgt tagatgtaga aaataaattg cttgatggct | 6600 |
| atatagcaaa aatgaatgta gcggataaaa atgccattgg tgacagaatt aagaaaggta | 6660 |
| ataaagaaat ctccgatgaa gaacttgcca aacaaatcaa agaagctgtg cgtaaaagcc | 6720 |
| atgagtttca gcaagtatta tcatcactgg aaaacaaaat ttttcattca aatgacggaa | 6780 |
| caaccaaagc aaccacacga gatttaaaat atgttgatta tggttactac ttggcgaatg | 6840 |
| atggcaatta tctaaccgtc aaaacagaca aactttggaa tttaggccct gtgggtggtg | 6900 |
| tgttttataa tggcacaacg accgccaaag agttgcccac acaagatgcg gtcaaatata | 6960 |
| aaggacattg ggactttatg accgatgttg ccaacgaag aaaccgattt agcgaagtga | 7020 |
| aagaaaactc tcaagcaggc tggtattatg gagcatcttc aaaagatgaa tacaaccgct | 7080 |
| tattaactaa agaagactct gcccctgatg gtcatagcgg tgaatatggc catagcagtg | 7140 |
| agtttactgt taatttaag gaaaaaaaat taacaggtaa gctgtttagt aacctacaag | 7200 |
| accgccataa gggcaatgtt acaaaaaccg aacgctatga catcgatgcc aatatccacg | 7260 |
| gcaaccgctt ccgtggcagt gccaccgcaa gcaataaaaa tgacacaagc aaacacccct | 7320 |
| ttaccagtga tgccaacaat aggctagaag gtggttttta tgggcaaaaa ggcgaggagc | 7380 |
| tggcaggtaa attcttaacc aatgacaaca aactctttgg cgtctttggt gctaaacgag | 7440 |

-continued

```
agagtaaagc tgaggaaaaa accgaagcca tcttagatgc ctatgcactt gggacattta   7500
atacaagtaa cgcaaccaca ttcaccccat ttaccgaaaa acaactggat aactttggca   7560
atgccaaaaa attggtctta ggttctaccg tcattgattt ggtgcctact gatgccacca   7620
aaaatgaatt caccaaagac aagccagagt ctgccacaaa cgaagcgggc gagactttga   7680
tggtgaatga tgaagttagc gtcaaaacct atggcaaaaa cttttgaatac ctaaaatttg   7740 gtgagcttag tatcggtggt agccatagcg tcttttttaca aggcgaacgc accgctacca   7800
caggcgagaa agccgtacca accacaggca cagccaaata tttggggaac tgggtaggat   7860
acatcacagg aaaggacaca ggaacgggca caggaaaaag ctttaccgat gcccaagatg   7920
ttgctgattt tgacattgat tttggaaata aatcagtcag cggtaaactt atcaccaaag   7980
gccgccaaga ccctgtattt agcatcacag gtcaaatcgc aggcaatggc tggacaggga   8040
cagccagcac caccaaagcg gacgcaggag gctacaagat agattctagc agtacaggca   8100
aatccatcgc catcaaagat gccaatgtta caggggctt ttatggtcca aatgcaaacg   8160
agatgggcgg gtcatttaca cacaacgccg atgacagcaa agcctctgtg gtctttggca   8220
caaaaagaca acaagaagtt aagtagtaat ttaaacacaa tgtttg                 8266
```

<210> SEQ ID NO 11
<211> LENGTH: 2288
<212> TYPE: PRT
<213> ORGANISM: Moraxella catarrhalis

<400> SEQUENCE: 11

```
Met Asn Gln Ser Lys Gln Asn Lys Ser Lys Lys Ser Lys Gln Val
  1               5                  10                  15

Leu Lys Leu Ser Ala Leu Ser Leu Gly Leu Leu Asn Ile Thr Gln Val
                 20                  25                  30

Ala Leu Ala Asn Thr Thr Ala Asp Lys Ala Glu Ala Thr Asp Lys Thr
             35                  40                  45

Asn Leu Val Val Leu Asp Glu Thr Val Val Thr Ala Lys Lys Asn
         50                  55                  60

Ala Arg Lys Ala Asn Glu Val Thr Gly Leu Gly Lys Val Val Lys Thr
 65                  70                  75                  80

Ala Glu Thr Ile Asn Lys Glu Gln Val Leu Asn Ile Arg Asp Leu Thr
                 85                  90                  95

Arg Tyr Asp Pro Gly Ile Ala Val Val Glu Gln Gly Arg Gly Ala Ser
                100                 105                 110

Ser Gly Tyr Ser Ile Arg Gly Met Asp Lys Asn Arg Val Ala Val Leu
            115                 120                 125

Val Asp Gly Ile Asn Gln Ala Gln His Tyr Ala Leu Gln Gly Pro Val
        130                 135                 140

Ala Gly Lys Asn Tyr Ala Ala Gly Gly Ala Ile Asn Glu Ile Glu Tyr
145                 150                 155                 160

Glu Asn Val Arg Ser Val Glu Ile Ser Lys Gly Ala Asn Ser Glu
                165                 170                 175

Tyr Gly Ser Gly Ala Leu Ser Gly Ser Val Ala Phe Val Thr Lys Thr
            180                 185                 190

Ala Asp Asp Ile Ile Lys Asp Gly Lys Asp Trp Gly Val Gln Thr Lys
        195                 200                 205

Thr Ala Tyr Ala Ser Lys Asn Asn Ala Trp Val Asn Ser Val Ala Ala
    210                 215                 220
```

```
Ala Gly Lys Ala Gly Ser Phe Ser Gly Leu Ile Ile Tyr Thr Asp Arg
225                 230                 235                 240

Arg Gly Gln Glu Tyr Lys Ala His Asp Asp Ala Tyr Gln Gly Ser Gln
                245                 250                 255

Ser Phe Asp Arg Ala Val Ala Thr Thr Asp Pro Asn Asn Arg Thr Phe
            260                 265                 270

Leu Ile Ala Asn Glu Cys Ala Asn Gly Asn Tyr Glu Ala Cys Ala Ala
        275                 280                 285

Gly Gly Gln Thr Lys Leu Gln Ala Lys Pro Thr Asn Val Arg Asp Lys
    290                 295                 300

Val Asn Val Lys Asp Tyr Thr Gly Pro Asn Arg Leu Ile Pro Asn Pro
305                 310                 315                 320

Leu Thr Gln Asp Ser Lys Ser Leu Leu Leu Arg Pro Gly Tyr Gln Leu
                325                 330                 335

Asn Asp Lys His Tyr Val Gly Gly Val Tyr Glu Ile Thr Lys Gln Asn
            340                 345                 350

Tyr Ala Met Gln Asp Lys Thr Val Pro Ala Tyr Leu Ala Val His Asp
        355                 360                 365

Ile Glu Lys Ser Arg Leu Ser Asn His Ala Gln Ala Asn Gly Tyr Tyr
370                 375                 380

Gln Gly Asn Asn Leu Gly Glu Arg Ile Arg Asp Thr Ile Gly Pro Asp
385                 390                 395                 400

Ser Gly Tyr Gly Ile Asn Tyr Ala His Gly Val Phe Tyr Asp Glu Lys
                405                 410                 415

His Gln Lys Asp Arg Leu Gly Leu Glu Tyr Val Tyr Asp Ser Lys Gly
            420                 425                 430

Glu Asn Lys Trp Phe Asp Asp Val Arg Val Ser Tyr Asp Lys Gln Asp
        435                 440                 445

Ile Thr Leu Arg Ser Gln Leu Thr Asn Thr His Cys Ser Thr Tyr Pro
    450                 455                 460

His Ile Asp Lys Asn Cys Thr Pro Asp Val Asn Lys Pro Phe Ser Val
465                 470                 475                 480

Lys Glu Val Asp Asn Asn Ala Tyr Lys Glu Gln His Asn Leu Ile Lys
                485                 490                 495

Ala Val Phe Asn Lys Lys Met Ala Leu Gly Ser Thr His His Ile
            500                 505                 510

Asn Leu Gln Val Gly Tyr Asp Lys Phe Asn Ser Ser Leu Ser Arg Val
        515                 520                 525

Glu Tyr Arg Leu Ala Thr His Gln Ser Tyr Gln Lys Leu Asp Tyr Thr
    530                 535                 540

Pro Pro Ser Asn Pro Leu Pro Asp Lys Phe Lys Pro Ile Leu Gly Ser
545                 550                 555                 560

Asn Asn Lys Pro Ile Cys Leu Asp Ala Tyr Gly Tyr Gly His Asp His
                565                 570                 575

Pro Gln Ala Cys Asn Ala Lys Asn Ser Thr Tyr Gln Asn Phe Ala Ile
            580                 585                 590

Lys Lys Gly Ile Glu Gln Tyr Asn Gln Lys Thr Asn Thr Asp Lys Ile
        595                 600                 605

Asp Tyr Gln Ala Ile Ile Asp Gln Tyr Asp Lys Gln Asn Pro Asn Ser
    610                 615                 620

Thr Leu Lys Pro Phe Glu Lys Ile Lys Gln Ser Leu Gly Gln Glu Lys
625                 630                 635                 640

Tyr Asn Lys Ile Asp Glu Leu Gly Phe Lys Ala Tyr Lys Asp Leu Arg
```

-continued

```
                645                 650                 655
Asn Glu Trp Ala Gly Trp Thr Asn Asp Asn Ser Gln Gln Asn Ala Asn
            660                 665                 670
Lys Gly Thr Asp Asn Ile Tyr Gln Pro Asn Gln Ala Thr Val Val Lys
        675                 680                 685
Asp Asp Lys Cys Lys Tyr Ser Glu Thr Asn Ser Tyr Ala Asp Cys Ser
    690                 695                 700
Thr Thr Arg His Ile Ser Gly Asp Asn Tyr Phe Ile Ala Leu Lys Asp
705                 710                 715                 720
Asn Met Thr Ile Asn Lys Tyr Val Asp Leu Gly Leu Gly Ala Arg Tyr
            725                 730                 735
Asp Arg Ile Lys His Lys Ser Asp Val Pro Leu Val Asp Asn Ser Ala
        740                 745                 750
Ser Asn Gln Leu Ser Trp Asn Phe Gly Val Val Lys Pro Thr Asn
    755                 760                 765
Trp Leu Asp Ile Ala Tyr Arg Ser Ser Gln Gly Phe Arg Met Pro Ser
770                 775                 780
Phe Ser Glu Met Tyr Gly Glu Arg Phe Gly Val Thr Ile Gly Lys Gly
785             790                 795                 800
Thr Gln His Gly Cys Lys Gly Leu Tyr Tyr Ile Cys Gln Gln Thr Val
                805                 810                 815
His Gln Thr Lys Leu Lys Pro Glu Lys Ser Phe Asn Gln Glu Ile Gly
            820                 825                 830
Ala Thr Leu His Asn His Leu Gly Ser Leu Glu Val Ser Tyr Phe Lys
        835                 840                 845
Asn Arg Tyr Thr Asp Leu Ile Val Gly Lys Ser Glu Glu Ile Arg Thr
    850                 855                 860
Leu Thr Gln Gly Asp Asn Ala Gly Lys Gln Arg Gly Lys Gly Asp Leu
865                 870                 875                 880
Gly Phe His Asn Gly Gln Asp Ala Asp Leu Thr Gly Ile Asn Ile Leu
            885                 890                 895
Gly Arg Leu Asp Leu Asn Ala Ala Asn Ser Arg Leu Pro Tyr Gly Leu
        900                 905                 910
Tyr Ser Thr Leu Ala Tyr Asn Lys Val Asp Val Lys Gly Lys Thr Leu
    915                 920                 925
Asn Pro Thr Leu Ala Gly Thr Asn Ile Leu Phe Asp Ala Ile Gln Pro
930                 935                 940
Ser Arg Tyr Val Val Gly Leu Gly Tyr Asp Ala Pro Ser Gln Lys Trp
945                 950                 955                 960
Gly Ala Asn Ala Ile Phe Thr His Ser Asp Ala Lys Asn Pro Ser Glu
            965                 970                 975
Leu Leu Ala Asp Lys Asn Leu Gly Asn Gly Asn Ile Gln Thr Lys Gln
        980                 985                 990
Ala Thr Lys Ala Lys Ser Thr Pro Trp Gln Thr Leu Asp Leu Ser Gly
    995                 1000                1005
Tyr Val Asn Ile Lys Asp Asn Phe Thr Leu Arg Ala Gly Val Tyr Asn
    1010                1015                1020
Val Phe Asn Thr Tyr Tyr Thr Thr Trp Glu Ala Leu Arg Gln Thr Ala
1025                1030                1035                1040
Lys Gly Ala Val Asn Gln His Thr Gly Leu Ser Gln Asp Lys His Tyr
            1045                1050                1055
Gly Arg Tyr Ala Ala Pro Gly Arg Asn Tyr Gln Leu Ala Leu Glu Met
        1060                1065                1070
```

-continued

```
Lys Phe Met Leu Ala Phe Leu Ile Gly Ala Val Met Thr Ile Thr Pro
    1075                1080                1085

Val Tyr Thr Thr Phe Thr Pro Thr Lys Thr Pro Ile Lys Phe Phe Met
    1090                1095                1100

Ala Gly Leu Thr Phe Leu Ile Ala His Ile Ser His Ala Asp Asp Gly
1105                1110                1115                1120

Arg Thr Asp Asn Gln Glu Leu Ile Asn Gln Glu Ile Ala Thr Leu Glu
            1125                1130                1135

Pro Ile Ile Asn His Ala Gln Pro Glu Leu Leu Ser His Asp Ala Leu
        1140                1145                1150

Thr Pro Lys Ile Glu Pro Ile Leu Ala Gln Thr Pro Asn Pro Ala Glu
    1155                1160                1165

Asp Thr Leu Ile Ala Asp Glu Ala Leu Leu Asp Asn Pro Asp Leu
    1170                1175                1180

Leu Asn His Ala Leu Asn Ser Ala Val Met Thr Asn His Met Ala Gly
1185                1190                1195                1200

Val His Ala Leu Leu Pro Ile Tyr Gln Lys Leu Pro Lys Asp His Gln
            1205                1210                1215

Asn Gly Ile Leu Leu Gly Tyr Ala Asn Ala Leu Ala Ala Leu Asp Lys
        1220                1225                1230

Gly Asn Ala Lys Lys Ala Ile Asp Glu Leu Arg Arg Ile Ile Ala Ile
    1235                1240                1245

Met Pro Glu Tyr Asn Val Val Arg Phe His Leu Ala Arg Ala Leu Phe
    1250                1255                1260

Met Asp Lys Gln Asn Glu Ala Ala Leu Asp Gln Phe Asn Lys Leu His
1265                1270                1275                1280

Ala Asp Asn Leu Pro Glu Glu Val Arg Gln Val Val Gly Gln Tyr Arg
            1285                1290                1295

Gln Ala Leu Lys Gln Arg Asp Ser Trp Thr Trp Gln Val Gly Met Asn
        1300                1305                1310

Leu Ala Lys Glu Asp Asn Ile Asn Gln Thr Pro Lys Asn Thr Thr Gln
    1315                1320                1325

Gly Gln Trp Thr Phe Asp Lys Pro Ile Asp Ala Ile Thr Leu Ser Tyr
    1330                1335                1340

Gln Leu Gly Ala Asp Lys Lys Trp Ser Leu Pro Lys Gly Ala Tyr Val
1345                1350                1355                1360

Gly Ala Asn Ala Gln Ile Tyr Gly Lys His His Gln Asn His Lys Lys
            1365                1370                1375

Tyr Asn Asp His Trp Gly Arg Leu Gly Ala Asn Leu Gly Phe Ala Asp
        1380                1385                1390

Ala Lys Lys Asp Leu Ser Ile Glu Thr Tyr Gly Glu Lys Arg Phe Tyr
    1395                1400                1405

Gly His Glu Arg Tyr Thr Asp Thr Ile Gly Ile Arg Met Ser Val Asp
    1410                1415                1420

Tyr Arg Ile Asn Pro Lys Phe Gln Ser Leu Asn Ala Ile Asp Ile Ser
1425                1430                1435                1440

Arg Leu Thr Asn His Arg Thr Pro Arg Ala Asp Ser Asn Asn Thr Leu
            1445                1450                1455

Tyr Ser Thr Ser Leu Ile Tyr Tyr Pro Asn Ala Thr Arg Tyr Tyr Leu
        1460                1465                1470

Leu Gly Ala Asp Phe Tyr Asp Glu Lys Val Pro Gln Asp Pro Ser Asp
    1475                1480                1485
```

-continued

```
Ser Tyr Gln Arg Arg Gly Ile Arg Thr Ala Trp Gly Gln Glu Trp Ala
    1490                1495                1500
Gly Gly Leu Ser Ser Arg Ala Gln Ile Ser Ile Asn Lys Arg His Tyr
1505                1510                1515                1520
Gln Gly Ala Asn Leu Thr Ser Gly Gly Gln Ile Arg His Asp Lys Gln
        1525                1530                1535
Met Gln Ala Ser Leu Ser Leu Trp His Arg Asp Ile His Lys Trp Gly
        1540                1545                1550
Ile Thr Pro Arg Leu Thr Ile Ser Thr Asn Ile Asn Lys Ser Asn Asp
    1555                1560                1565
Ile Lys Ala Asn Tyr His Lys Asn Gln Met Phe Val Glu Phe Ser Arg
1570                1575                1580
Ile Phe Met Lys His Ile Pro Leu Thr Thr Leu Cys Val Ala Ile Ser
1585                1590                1595                1600
Ala Val Leu Leu Thr Ala Cys Gly Gly Ser Gly Gly Ser Asn Pro Pro
        1605                1610                1615
Ala Pro Thr Pro Ile Pro Asn Ala Ser Gly Ser Gly Asn Thr Gly Asn
        1620                1625                1630
Thr Gly Asn Ala Gly Gly Thr Asp Asn Thr Ala Asn Ala Gly Asn Thr
    1635                1640                1645
Gly Gly Thr Asn Ser Gly Thr Gly Ser Ala Asn Thr Pro Glu Pro Lys
1650                1655                1660
Tyr Gln Asp Val Pro Thr Glu Lys Asn Glu Lys Asp Lys Val Ser Ser
1665                1670                1675                1680
Ile Gln Glu Pro Ala Met Gly Tyr Gly Met Ala Leu Ser Lys Ile Asn
        1685                1690                1695
Leu His Asn Arg Gln Asp Thr Pro Leu Asp Glu Lys Asn Ile Ile Thr
    1700                1705                1710
Leu Asp Gly Lys Lys Gln Val Ala Glu Gly Lys Lys Ser Pro Leu Pro
    1715                1720                1725
Phe Ser Leu Asp Val Glu Asn Lys Leu Leu Asp Gly Tyr Ile Ala Lys
    1730                1735                1740
Met Asn Val Ala Asp Lys Asn Ala Ile Gly Asp Arg Ile Lys Lys Gly
1745                1750                1755                1760
Asn Lys Glu Ile Ser Asp Glu Glu Leu Ala Lys Gln Ile Lys Glu Ala
        1765                1770                1775
Val Arg Lys Ser His Glu Phe Gln Gln Val Leu Ser Ser Leu Glu Asn
    1780                1785                1790
Lys Ile Phe His Ser Asn Asp Gly Thr Thr Lys Ala Thr Thr Arg Asp
    1795                1800                1805
Leu Lys Tyr Val Asp Tyr Gly Tyr Tyr Leu Ala Asn Asp Gly Asn Tyr
    1810                1815                1820
Leu Thr Val Lys Thr Asp Lys Leu Trp Asn Leu Gly Pro Val Gly Gly
1825                1830                1835                1840
Val Phe Tyr Asn Gly Thr Thr Thr Ala Lys Glu Leu Pro Thr Gln Asp
        1845                1850                1855
Ala Val Lys Tyr Lys Gly His Trp Asp Phe Met Thr Asp Val Ala Asn
        1860                1865                1870
Arg Arg Asn Arg Phe Ser Glu Val Lys Glu Asn Ser Gln Ala Gly Trp
    1875                1880                1885
Tyr Tyr Gly Ala Ser Ser Lys Asp Glu Tyr Asn Arg Leu Leu Thr Lys
    1890                1895                1900
Glu Asp Ser Ala Pro Asp Gly His Ser Gly Glu Tyr Gly His Ser Ser
```

-continued

```
1905                1910                1915                1920

Glu Phe Thr Val Asn Phe Lys Glu Lys Lys Leu Thr Gly Lys Leu Phe
               1925                1930                1935

Ser Asn Leu Gln Asp Arg His Lys Gly Asn Val Thr Lys Thr Glu Arg
           1940                1945                1950

Tyr Asp Ile Asp Ala Asn Ile His Gly Asn Arg Phe Arg Gly Ser Ala
       1955                1960                1965

Thr Ala Ser Asn Lys Asn Asp Thr Ser Lys His Pro Phe Thr Ser Asp
   1970                1975                1980

Ala Asn Asn Arg Leu Glu Gly Gly Phe Tyr Gly Pro Lys Gly Glu Glu
1985                1990                1995                2000

Leu Ala Gly Lys Phe Leu Thr Asn Asp Asn Lys Leu Phe Gly Val Phe
               2005                2010                2015

Gly Ala Lys Arg Glu Ser Lys Ala Glu Glu Lys Thr Glu Ala Ile Leu
           2020                2025                2030

Asp Ala Tyr Ala Leu Gly Thr Phe Asn Thr Ser Asn Ala Thr Thr Phe
       2035                2040                2045

Thr Pro Phe Thr Glu Lys Gln Leu Asp Asn Phe Gly Asn Ala Lys Lys
   2050                2055                2060

Leu Val Leu Gly Ser Thr Val Ile Asp Leu Val Pro Thr Asp Ala Thr
2065                2070                2075                2080

Lys Asn Glu Phe Thr Lys Asp Lys Pro Glu Ser Ala Thr Asn Glu Ala
               2085                2090                2095

Gly Glu Thr Leu Met Val Asn Asp Glu Val Ser Val Lys Thr Tyr Gly
           2100                2105                2110

Lys Asn Phe Glu Tyr Leu Lys Phe Gly Glu Leu Ser Ile Gly Gly Ser
       2115                2120                2125

His Ser Val Phe Leu Gln Gly Glu Arg Thr Ala Thr Thr Gly Glu Lys
   2130                2135                2140

Ala Val Pro Thr Thr Gly Thr Ala Lys Tyr Leu Gly Asn Trp Val Gly
2145                2150                2155                2160

Tyr Ile Thr Gly Lys Asp Thr Gly Thr Gly Thr Gly Lys Ser Phe Thr
               2165                2170                2175

Asp Ala Gln Asp Val Ala Asp Phe Asp Ile Asp Phe Gly Asn Lys Ser
           2180                2185                2190

Val Ser Gly Lys Leu Ile Thr Lys Gly Arg Gln Asp Pro Val Phe Ser
       2195                2200                2205

Ile Thr Gly Gln Ile Ala Gly Asn Gly Trp Thr Gly Thr Ala Ser Thr
   2210                2215                2220

Thr Lys Ala Asp Ala Gly Gly Tyr Lys Ile Asp Ser Ser Ser Thr Gly
2225                2230                2235                2240

Lys Ser Ile Ala Ile Lys Asp Ala Asn Val Thr Gly Gly Phe Tyr Gly
               2245                2250                2255

Pro Asn Ala Asn Glu Met Gly Gly Ser Phe Thr His Asn Ala Asp Asp
           2260                2265                2270

Ser Lys Ala Ser Val Val Phe Gly Thr Lys Arg Gln Gln Glu Val Lys
       2275                2280                2285
```

<210> SEQ ID NO 12
<211> LENGTH: 1074
<212> TYPE: PRT
<213> ORGANISM: Moraxella catarrhalis

<400> SEQUENCE: 12

-continued

```
Met Asn Gln Ser Lys Gln Asn Asn Lys Ser Lys Lys Ser Lys Gln Val
1               5                   10                  15

Leu Lys Leu Ser Ala Leu Ser Leu Gly Leu Leu Asn Ile Thr Gln Val
                20                  25                  30

Ala Leu Ala Asn Thr Thr Ala Asp Lys Ala Glu Ala Thr Asp Lys Thr
            35                  40                  45

Asn Leu Val Val Val Leu Asp Glu Thr Val Val Thr Ala Lys Lys Asn
        50                  55                  60

Ala Arg Lys Ala Asn Glu Val Thr Gly Leu Gly Lys Val Lys Lys Thr
65                  70                  75                  80

Ala Glu Thr Ile Asn Lys Glu Gln Val Leu Asn Ile Arg Asp Leu Thr
                85                  90                  95

Arg Tyr Asp Pro Gly Ile Ala Val Val Glu Gln Gly Arg Gly Ala Ser
            100                 105                 110

Ser Gly Tyr Ser Ile Arg Gly Met Asp Lys Asn Arg Val Ala Val Leu
        115                 120                 125

Val Asp Gly Ile Asn Gln Ala Gln His Tyr Ala Leu Gln Gly Pro Val
    130                 135                 140

Ala Gly Lys Asn Tyr Ala Ala Gly Gly Ala Ile Asn Glu Ile Glu Tyr
145                 150                 155                 160

Glu Asn Val Arg Ser Val Glu Ile Ser Lys Gly Ala Asn Ser Ser Glu
                165                 170                 175

Tyr Gly Ser Gly Ala Leu Ser Gly Ser Val Ala Phe Val Thr Lys Thr
            180                 185                 190

Ala Asp Asp Ile Ile Lys Asp Gly Lys Asp Trp Gly Val Gln Thr Lys
        195                 200                 205

Thr Ala Tyr Ala Ser Lys Asn Asn Ala Trp Val Asn Ser Val Ala Ala
    210                 215                 220

Ala Gly Lys Ala Gly Ser Phe Ser Gly Leu Ile Ile Tyr Thr Asp Arg
225                 230                 235                 240

Arg Gly Gln Glu Tyr Lys Ala His Asp Asp Ala Tyr Gln Gly Ser Gln
                245                 250                 255

Ser Phe Asp Arg Ala Val Ala Thr Thr Asp Pro Asn Asn Arg Thr Phe
            260                 265                 270

Leu Ile Ala Asn Glu Cys Ala Asn Gly Asn Tyr Glu Ala Cys Ala Ala
        275                 280                 285

Gly Gly Gln Thr Lys Leu Gln Ala Lys Pro Thr Asn Val Arg Asp Lys
    290                 295                 300

Val Asn Val Lys Asp Tyr Thr Gly Pro Asn Arg Leu Ile Pro Asn Pro
305                 310                 315                 320

Leu Thr Gln Asp Ser Lys Ser Leu Leu Leu Arg Pro Gly Tyr Gln Leu
                325                 330                 335

Asn Asp Lys His Tyr Val Gly Val Tyr Glu Ile Thr Lys Gln Asn
            340                 345                 350

Tyr Ala Met Gln Asp Lys Thr Val Pro Ala Tyr Leu Ala Val His Asp
        355                 360                 365

Ile Glu Lys Ser Arg Leu Ser Asn His Ala Gln Ala Asn Gly Tyr Tyr
    370                 375                 380

Gln Gly Asn Asn Leu Gly Glu Arg Ile Arg Asp Thr Ile Gly Pro Asp
385                 390                 395                 400

Ser Gly Tyr Gly Ile Asn Tyr Ala His Gly Val Phe Tyr Asp Glu Lys
                405                 410                 415

His Gln Lys Asp Arg Leu Gly Leu Glu Tyr Val Tyr Asp Ser Lys Gly
```

```
                    420             425             430
Glu Asn Lys Trp Phe Asp Asp Val Arg Val Ser Tyr Asp Lys Gln Asp
            435             440             445
Ile Thr Leu Arg Ser Gln Leu Thr Asn Thr His Cys Ser Thr Tyr Pro
450             455             460
His Ile Asp Lys Asn Cys Thr Pro Asp Val Asn Lys Pro Phe Ser Val
465             470             475             480
Lys Glu Val Asp Asn Asn Ala Tyr Lys Glu Gln His Asn Leu Ile Lys
                485             490             495
Ala Val Phe Asn Lys Lys Met Ala Leu Gly Ser Thr His His Ile
                500             505             510
Asn Leu Gln Val Gly Tyr Asp Lys Phe Asn Ser Ser Leu Ser Arg Val
            515             520             525
Glu Tyr Arg Leu Ala Thr His Gln Ser Tyr Gln Lys Leu Asp Tyr Thr
        530             535             540
Pro Pro Ser Asn Pro Leu Pro Asp Lys Phe Lys Pro Ile Leu Gly Ser
545             550             555             560
Asn Asn Lys Pro Ile Cys Leu Asp Ala Tyr Gly Tyr Gly His Asp His
                565             570             575
Pro Gln Ala Cys Asn Ala Lys Asn Ser Thr Tyr Gln Asn Phe Ala Ile
            580             585             590
Lys Lys Gly Ile Glu Gln Tyr Asn Gln Lys Thr Asn Thr Asp Lys Ile
        595             600             605
Asp Tyr Gln Ala Ile Ile Asp Gln Tyr Asp Lys Gln Asn Pro Asn Ser
610             615             620
Thr Leu Lys Pro Phe Glu Lys Ile Lys Gln Ser Leu Gly Gln Glu Lys
625             630             635             640
Tyr Asn Lys Ile Asp Glu Leu Gly Phe Lys Ala Tyr Lys Asp Leu Arg
                645             650             655
Asn Glu Trp Ala Gly Trp Thr Asn Asp Asn Ser Gln Gln Asn Ala Asn
            660             665             670
Lys Gly Thr Asp Asn Ile Tyr Gln Pro Asn Gln Ala Thr Val Val Lys
        675             680             685
Asp Asp Lys Cys Lys Tyr Ser Glu Thr Asn Ser Tyr Ala Asp Cys Ser
690             695             700
Thr Thr Arg His Ile Ser Gly Asp Asn Tyr Phe Ile Ala Leu Lys Asp
705             710             715             720
Asn Met Thr Ile Asn Lys Tyr Val Asp Leu Gly Leu Gly Ala Arg Tyr
                725             730             735
Asp Arg Ile Lys His Lys Ser Asp Val Pro Leu Val Asp Asn Ser Ala
            740             745             750
Ser Asn Gln Leu Ser Trp Asn Phe Gly Val Val Lys Pro Thr Asn
        755             760             765
Trp Leu Asp Ile Ala Tyr Arg Ser Ser Gln Gly Phe Arg Met Pro Ser
770             775             780
Phe Ser Glu Met Tyr Gly Glu Arg Phe Gly Val Thr Ile Gly Lys Gly
785             790             795             800
Thr Gln His Gly Cys Lys Gly Leu Tyr Tyr Ile Cys Gln Gln Thr Val
                805             810             815
His Gln Thr Lys Leu Lys Pro Glu Lys Ser Phe Asn Gln Glu Ile Gly
            820             825             830
Ala Thr Leu His Asn His Leu Gly Ser Leu Glu Val Ser Tyr Phe Lys
        835             840             845
```

-continued

```
Asn Arg Tyr Thr Asp Leu Ile Val Gly Lys Ser Glu Glu Ile Arg Thr
    850                 855                 860
Leu Thr Gln Gly Asp Asn Ala Gly Lys Gln Arg Gly Lys Gly Asp Leu
865                 870                 875                 880
Gly Phe His Asn Gly Gln Asp Ala Asp Leu Thr Gly Ile Asn Ile Leu
                885                 890                 895
Gly Arg Leu Asp Leu Asn Ala Ala Asn Ser Arg Leu Pro Tyr Gly Leu
            900                 905                 910
Tyr Ser Thr Leu Ala Tyr Asn Lys Val Asp Val Lys Gly Lys Thr Leu
        915                 920                 925
Asn Pro Thr Leu Ala Gly Thr Asn Ile Leu Phe Asp Ala Ile Gln Pro
    930                 935                 940
Ser Arg Tyr Val Val Gly Leu Gly Tyr Asp Ala Pro Ser Gln Lys Trp
945                 950                 955                 960
Gly Ala Asn Ala Ile Phe Thr His Ser Asp Ala Lys Asn Pro Ser Glu
                965                 970                 975
Leu Leu Ala Asp Lys Asn Leu Gly Asn Gly Asn Ile Gln Thr Lys Gln
            980                 985                 990
Ala Thr Lys Ala Lys Ser Thr Pro Trp Gln Thr Leu Asp Leu Ser Gly
        995                 1000                1005
Tyr Val Asn Ile Lys Asp Asn Phe Thr Leu Arg Ala Gly Val Tyr Asn
    1010                1015                1020
Val Phe Asn Thr Tyr Tyr Thr Thr Trp Glu Ala Leu Arg Gln Thr Ala
1025                1030                1035                1040
Lys Gly Ala Val Asn Gln His Thr Gly Leu Ser Gln Asp Lys His Tyr
                1045                1050                1055
Gly Arg Tyr Ala Ala Pro Gly Arg Asn Tyr Gln Leu Ala Leu Glu Met
            1060                1065                1070
Lys Phe
```

<210> SEQ ID NO 13
<211> LENGTH: 1539
<212> TYPE: DNA
<213> ORGANISM: Moraxella catarrhalis

<400> SEQUENCE: 13

```
atgctcgctt ttttgatagg agctgtcatg acaatcacgc tgtttatac  cacattcacc    60
cccaccaaaa cacccataaa attttttatg gctggcttga cttttctaat cgctcatatc   120
agccatgccg atgatggtcg caccgacaat caagagctaa tcaatcaaga aatagccacc   180
cttgaaccca tcattaacca tgctcagcct gagttattgt cccatgatgc attaacacca   240
aaaatagaac caatactggc acaaacacca atcctgccg aagatacgct catcgccgat   300
gaggcgttac tgcttgataa ccctgatttg ctcaatcacg ccctaaattc tgctgtcatg   360
accaatcata tggcaggcgt tcacgcatta ttgcccattt atcaaaaact gcccaaagac   420
catcaaaatg gcattttact tgggtatgcc aatgccttgg ctgctttgga taagggcaac   480
gccaaaaaag ccattgatga gctacgtcgc atcatcgcca tcatgcctga atataatgtg   540
gtgcgttttc atctggcaag ggcattattt atggacaaac aaaatgaagc cgccccttgac   600
cagtttaata aattacatgc tgacaacttg ccagaggagg tgcggcaggt tgttgggcag   660
tacagacaag cgctaaaaca acgagattca tggacatggc aagtaggcat gaatctggcc   720
aaagaagaca acatcaatca accccccaaa aacaccacgc aaggtcaatg gacttttgac   780
```

-continued

```
aaacccattg acgccatcac cctaagctac caattggggg cggataaaaa gtggtctttg     840
cccaaagggg catatgtggg agcgaacgcc caaatctatg gcaaacatca tcaaaatcac     900
aaaaaataca acgaccattg gggcagactg ggggcaaatt tgggctttgc tgatgccaaa     960 aaagaccta gcattgagac ctatggtgaa aaagatttt atgggcatga gcgttatacc      1020
gacaccattg gcatacgcat gtcggttgat tatagaatca acccaaaatt tcaaagccta    1080
aacgccatag acatatcacg cctaaccaac catcggacgc ctagggctga cagtaataac    1140
actttataca gtacctcatt gatttattac ccaaatgcca cacgctatta tcttttgggg    1200
gcagactttt atgatgaaaa agtgccacaa gacccatctg acagttatca acgccgtggc    1260
atacgcacag cgtgggggca agaatgggcg ggtggtcttt caagccgtgc ccaaatcagc    1320
atcaacaaac gccattacca aggggcaaac ctaaccagcg gtggacaaat tcgccatgat    1380
aaacagatgc aagcgtcttt atcgctttgg cacagagaca ttcacaaatg gggcatcacg    1440
ccacggctga ccatcagcac aaacatcaat aaaagcaatg acatcaaggc aaattatcac    1500
aaaaatcaaa tgtttgttga gtttagtcgc attttttga                           1539
```

<210> SEQ ID NO 14
<211> LENGTH: 512
<212> TYPE: PRT
<213> ORGANISM: Moraxella catarrhalis

<400> SEQUENCE: 14

```
Met Leu Ala Phe Leu Ile Gly Ala Val Met Thr Ile Thr Pro Val Tyr
  1               5                  10                  15

Thr Thr Phe Thr Pro Thr Lys Thr Pro Ile Lys Phe Phe Met Ala Gly
                 20                  25                  30

Leu Thr Phe Leu Ile Ala His Ile Ser His Ala Asp Asp Gly Arg Thr
             35                  40                  45

Asp Asn Gln Glu Leu Ile Asn Gln Glu Ile Ala Thr Leu Glu Pro Ile
         50                  55                  60

Ile Asn His Ala Gln Pro Glu Leu Leu Ser His Asp Ala Leu Thr Pro
 65                  70                  75                  80

Lys Ile Glu Pro Ile Leu Ala Gln Thr Pro Asn Pro Ala Glu Asp Thr
                 85                  90                  95

Leu Ile Ala Asp Glu Ala Leu Leu Leu Asp Asn Pro Asp Leu Leu Asn
            100                 105                 110

His Ala Leu Asn Ser Ala Val Met Thr Asn His Met Ala Gly Val His
        115                 120                 125

Ala Leu Leu Pro Ile Tyr Gln Lys Leu Pro Lys Asp His Gln Asn Gly
    130                 135                 140

Ile Leu Leu Gly Tyr Ala Asn Ala Leu Ala Ala Leu Asp Lys Gly Asn
145                 150                 155                 160

Ala Lys Lys Ala Ile Asp Glu Leu Arg Arg Ile Ile Ala Ile Met Pro
                165                 170                 175

Glu Tyr Asn Val Val Arg Phe His Leu Ala Arg Ala Leu Phe Met Asp
            180                 185                 190

Lys Gln Asn Glu Ala Ala Leu Asp Gln Phe Asn Lys Leu His Ala Asp
        195                 200                 205

Asn Leu Pro Glu Glu Val Arg Gln Val Val Gly Gln Tyr Arg Gln Ala
    210                 215                 220

Leu Lys Gln Arg Asp Ser Trp Thr Trp Gln Val Gly Met Asn Leu Ala
225                 230                 235                 240
```

-continued

```
Lys Glu Asp Asn Ile Asn Gln Thr Pro Lys Asn Thr Thr Gln Gly Gln
                245                 250                 255
Trp Thr Phe Asp Lys Pro Ile Asp Ala Ile Thr Leu Ser Tyr Gln Leu
            260                 265                 270
Gly Ala Asp Lys Lys Trp Ser Leu Pro Lys Gly Ala Tyr Val Gly Ala
        275                 280                 285
Asn Ala Gln Ile Tyr Gly Lys His His Gln Asn His Lys Lys Tyr Asn
    290                 295                 300
Asp His Trp Gly Arg Leu Gly Ala Asn Leu Gly Phe Ala Asp Ala Lys
305                 310                 315                 320
Lys Asp Leu Ser Ile Glu Thr Tyr Gly Glu Lys Arg Phe Tyr Gly His
                325                 330                 335
Glu Arg Tyr Thr Asp Thr Ile Gly Ile Arg Met Ser Val Asp Tyr Arg
            340                 345                 350
Ile Asn Pro Lys Phe Gln Ser Leu Asn Ala Ile Asp Ile Ser Arg Leu
        355                 360                 365
Thr Asn His Arg Thr Pro Arg Ala Asp Ser Asn Asn Thr Leu Tyr Ser
    370                 375                 380
Thr Ser Leu Ile Tyr Tyr Pro Asn Ala Thr Arg Tyr Tyr Leu Leu Gly
385                 390                 395                 400
Ala Asp Phe Tyr Asp Glu Lys Val Pro Gln Asp Pro Ser Asp Ser Tyr
                405                 410                 415
Gln Arg Arg Gly Ile Arg Thr Ala Trp Gly Gln Glu Trp Ala Gly Gly
            420                 425                 430
Leu Ser Ser Arg Ala Gln Ile Ser Ile Asn Lys Arg His Tyr Gln Gly
        435                 440                 445
Ala Asn Leu Thr Ser Gly Gly Gln Ile Arg His Asp Lys Gln Met Gln
    450                 455                 460
Ala Ser Leu Ser Leu Trp His Arg Asp Ile His Lys Trp Gly Ile Thr
465                 470                 475                 480
Pro Arg Leu Thr Ile Ser Thr Asn Ile Asn Lys Ser Asn Asp Ile Lys
                485                 490                 495
Ala Asn Tyr His Lys Asn Gln Met Phe Val Glu Phe Ser Arg Ile Phe
            500                 505                 510
```

<210> SEQ ID NO 15
<211> LENGTH: 2109
<212> TYPE: DNA
<213> ORGANISM: Moraxella catarrhalis

<400> SEQUENCE: 15

```
atgaaacaca ttcctttaac cacactgtgt gtggcaatct ctgccgtctt attaaccgct    60
tgtggtggca gtggtggttc aaatccacct gctcctacgc ccattccaaa tgctagcggt   120
tcaggtaata ctggcaacac tggtaatgct ggcggtactg ataatacagc caatgcaggt   180
aatacaggcg gtacaaactc tggtacaggc agtgccaaca caccagagcc aaaatatcaa   240
gatgtaccaa ctgagaaaaa tgaaaaagat aaagtttcat ccattcaaga acctgccatg   300
ggttatggca tggctttgag taaaattaat ctacacaacc gacaagacac gccattagat   360
gaaaaaaata tcattacctt agacggtaaa aaacaagttg cagaaggtaa aaaatcgcca   420
ttgccatttt cgttagatgt agaaaataaa ttgcttgatg gctatatagc aaaaatgaat   480
gtagcggata aaaatgccat tggtgacaga attaagaaag gtaataaaga aatctccgat   540
gaagaacttg ccaaacaaat caagaagct gtgcgtaaaa gccatgagtt tcagcaagta   600
```

-continued

```
ttatcatcac tggaaaacaa aattttttcat tcaaatgacg gaacaaccaa agcaaccaca    660
cgagatttaa aatatgttga ttatggttac tacttggcga atgatggcaa ttatctaacc    720
gtcaaaacag acaaactttg gaatttaggc cctgtgggtg gtgtgtttta taatggcaca    780
acgaccgcca aagagttgcc cacacaagat gcggtcaaat ataaaggaca ttgggacttt    840
atgaccgatg ttgccaacag aagaaaccga tttagcgaag tgaaagaaaa ctctcaagca    900
ggctggtatt atggagcatc ttcaaaagat gaatacaacc gcttattaac taaagaagac    960
tctgccctg atggtcatag cggtgaatat ggccatagca gtgagtttac tgttaatttt   1020
aaggaaaaaa aattaacagg taagctgttt agtaacctac aagaccgcca taagggcaat   1080
gttacaaaaa ccgaacgcta tgacatcgat gccaatatcc acggcaaccg cttccgtggc   1140
agtgccaccg caagcaataa aaatgacaca agcaaacacc cctttaccag tgatgccaac   1200
aataggctag aaggtggttt ttatgggcca aaaggcgagg agctggcagg taaattctta   1260
accaatgaca caaactctt tggcgtcttt ggtgctaaac gagagagtaa agctgaggaa   1320
aaaaccgaag ccatcttaga tgcctatgca cttgggacat ttaatacaag taacgcaacc   1380
acattcaccc catttaccga aaaacaactg gataactttg gcaatgccaa aaaattggtc   1440
ttaggttcta ccgtcattga tttggtgcct actgatgcca ccaaaaatga attcaccaaa   1500
gacaagccag agtctgccac aaacgaagcg ggcgagactt tgatggtgaa tgatgaagtt   1560
agcgtcaaaa cctatggcaa aaactttgaa tacctaaaat ttggtgagct tagtatcggt   1620
ggtagccata gcgtcttttt acaaggcgaa cgcaccgcta ccacaggcga aaagccgta   1680
ccaaccacag gcacagccaa atatttgggg aactgggtag gatacatcac aggaaaggac   1740
acaggaacgg gcacaggaaa aagctttacc gatgcccaag atgttgctga ttttgacatt   1800
gattttggaa ataaatcagt cagcggtaaa cttatcacca aaggccgcca agaccctgta   1860
tttagcatca caggtcaaat cgcaggcaat ggctggacag ggacagccag caccaccaaa   1920
gcggacgcag gaggctacaa gatagattct agcagtacag gcaaatccat cgccatcaaa   1980
gatgccaatg ttacaggggg ctttttatggt ccaaatgcaa acgagatggg cgggtcattt   2040
acacacaacg ccgatgacag caaagcctct gtggtctttg gcacaaaaag acaacaagaa   2100
gttaagtag                                                           2109
```

<210> SEQ ID NO 16
<211> LENGTH: 512
<212> TYPE: PRT
<213> ORGANISM: Moraxella catarrhalis

<400> SEQUENCE: 16

Met Leu Ala Phe Leu Ile Gly Ala Val Met Thr Ile Thr Pro Val Tyr
1               5                   10                  15

Thr Thr Phe Thr Pro Thr Lys Thr Pro Ile Lys Phe Phe Met Ala Gly
            20                  25                  30

Leu Thr Phe Leu Ile Ala His Ile Ser His Ala Asp Asp Gly Arg Thr
        35                  40                  45

Asp Asn Gln Glu Leu Ile Asn Gln Glu Ile Ala Thr Leu Glu Pro Ile
    50                  55                  60

Ile Asn His Ala Gln Pro Glu Leu Leu Ser His Asp Ala Leu Thr Pro
65                  70                  75                  80

Lys Ile Glu Pro Ile Leu Ala Gln Thr Pro Asn Pro Ala Glu Asp Thr
                85                  90                  95

Leu Ile Ala Asp Glu Ala Leu Leu Leu Asp Asn Pro Asp Leu Leu Asn

```
                100             105             110
His Ala Leu Asn Ser Ala Val Met Thr Asn Asn Met Ala Gly Val His
            115             120             125
Ala Leu Leu Pro Ile Tyr Gln Lys Leu Pro Lys Asp His Gln Asn Gly
130             135             140
Ile Leu Leu Gly Tyr Ala Asn Ala Leu Val Ala Leu Asp Lys Gly Asn
145             150             155             160
Ala Lys Ala Ala Ile Gly Glu Leu Arg Arg Ile Ala Ile Met Pro
            165             170             175
Glu Tyr Asn Val Val Arg Phe His Leu Ala Arg Ala Leu Phe Met Asp
            180             185             190
Lys Gln Asn Glu Ala Ala Leu Asp Gln Phe Asn Lys Leu His Ala Asp
            195             200             205
Asn Leu Pro Glu Glu Val Arg Arg Val Val Gly Gln Tyr Arg Gln Ala
210             215             220
Leu Lys Gln Arg Asp Ser Trp Thr Trp Gln Val Gly Met Asn Leu Ala
225             230             235             240
Lys Glu Asp Asn Ile Asn Gln Thr Pro Lys Asn Thr Thr Gln Gly Gln
            245             250             255
Trp Thr Phe Asp Lys Pro Ile Asp Ala Ile Thr Leu Ser Tyr Gln Leu
            260             265             270
Gly Ala Asp Lys Lys Trp Ser Leu Pro Lys Gly Ala Tyr Val Gly Ala
            275             280             285
Asn Ala Gln Ile Tyr Gly Lys His His Gln Asn His Lys Lys Tyr Asn
            290             295             300
Asp His Trp Gly Arg Leu Gly Ala Asn Leu Gly Phe Ala Asp Ala Lys
305             310             315             320
Lys Asp Leu Ser Ile Glu Thr Tyr Gly Glu Lys Arg Phe Tyr Gly His
                325             330             335
Glu Arg Tyr Thr Asp Thr Ile Gly Ile Arg Met Ser Ala Asp Tyr Arg
            340             345             350
Ile Asn Pro Lys Phe Gln Ser Leu Asn Ala Ile Asp Ile Ser Arg Leu
            355             360             365
Thr Asn His Arg Thr Pro Arg Ala Asp Ser Asn Asn Thr Leu Tyr Ser
370             375             380
Thr Ser Leu Ile Tyr Tyr Pro Asn Ala Thr Arg Tyr Tyr Leu Leu Gly
385             390             395             400
Ala Asp Phe Tyr Asp Glu Lys Val Pro Gln Asp Pro Ser Asp Ser Tyr
            405             410             415
Glu Arg Arg Gly Ile Arg Thr Ala Trp Gly Gln Glu Trp Ala Gly Gly
            420             425             430
Leu Ser Ser Arg Ala Gln Ile Ser Ile Asn Lys Arg His Tyr Gln Gly
            435             440             445
Ala Asn Leu Thr Ser Gly Gly Gln Ile Arg Gln Asp Lys Gln Met Gln
            450             455             460
Ala Ser Leu Ser Leu Trp His Arg Asp Ile His Lys Trp Gly Ile Thr
465             470             475             480
Pro Arg Leu Thr Ile Ser Thr Asn Ile Asn Lys Ser Asn Asp Ile Lys
                485             490             495
Ala Asn Tyr His Lys Asn Gln Met Phe Val Glu Phe Ser Arg Ile Phe
            500             505             510
```

<210> SEQ ID NO 17

-continued

```
<211> LENGTH: 10
<212> TYPE: PRT
<213> ORGANISM: Moraxella catarrhalis

<400> SEQUENCE: 17

Ile Arg Asp Leu Thr Arg Tyr Asp Pro Gly
 1               5                   10

<210> SEQ ID NO 18
<211> LENGTH: 30
<212> TYPE: DNA
<213> ORGANISM: Moraxella catarrhalis

<400> SEQUENCE: 18
attcgagact taacacgcta tgaccctggc                                           30

<210> SEQ ID NO 19
<211> LENGTH: 30
<212> TYPE: DNA
<213> ORGANISM: Moraxella catarrhalis

<400> SEQUENCE: 19
attcgtgatt taactcgcta tgaccctggt                                           30

<210> SEQ ID NO 20
<211> LENGTH: 23
<212> TYPE: DNA
<213> ORGANISM: Moraxella catarrhalis

<400> SEQUENCE: 20
gatgggataa gcacgcccta ctt                                                  23

<210> SEQ ID NO 21
<211> LENGTH: 25
<212> TYPE: DNA
<213> ORGANISM: Moraxella catarrhalis

<400> SEQUENCE: 21
cccatcagcc aaacaaacat tgtgt                                                25

<210> SEQ ID NO 22
<211> LENGTH: 7
<212> TYPE: PRT
<213> ORGANISM: Moraxella catarrhalis

<400> SEQUENCE: 22

Leu Glu Gly Gly Phe Tyr Gly
 1               5
```